United States Patent
Tsuchimura et al.

(10) Patent No.: US 9,223,208 B2
(45) Date of Patent: Dec. 29, 2015

(54) ACTINIC-RAY- OR RADIATION-SENSITIVE RESIN COMPOSITION AND METHOD OF FORMING PATTERN USING THE COMPOSITION

(75) Inventors: Tomotaka Tsuchimura, Shizuoka (JP); Takayuki Ito, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 303 days.

(21) Appl. No.: 13/340,305

(22) Filed: Dec. 29, 2011

(65) Prior Publication Data

US 2013/0171562 A1   Jul. 4, 2013

(51) Int. Cl.

| | |
|---|---|
| *G03F 7/004* | (2006.01) |
| *G03F 7/38* | (2006.01) |
| *C07C 317/14* | (2006.01) |
| *C07C 317/44* | (2006.01) |
| *C07C 309/71* | (2006.01) |
| *C07C 309/73* | (2006.01) |
| *C07C 309/77* | (2006.01) |
| *C07D 405/12* | (2006.01) |
| *G03F 7/038* | (2006.01) |
| *G03F 7/039* | (2006.01) |
| *G03F 7/20* | (2006.01) |

(52) U.S. Cl.
CPC ............ *G03F 7/0045* (2013.01); *C07C 309/71* (2013.01); *C07C 309/73* (2013.01); *C07C 309/77* (2013.01); *C07C 317/14* (2013.01); *C07C 317/44* (2013.01); *C07D 405/12* (2013.01); *G03F 7/0046* (2013.01); *G03F 7/0382* (2013.01); *G03F 7/0397* (2013.01); *G03F 7/2041* (2013.01); *G03F 7/38* (2013.01)

(58) Field of Classification Search
CPC ........... G03F 7/0045; G03F 7/30; G03F 7/38; G03F 7/40; G03F 7/0382; G03F 7/0397; G03F 7/2041; C07C 317/14; C07C 317/44; C07C 309/71; C07C 309/73; C07C 309/77; C07D 405/12

USPC .............. 430/270.1, 921, 922, 325, 326, 910; 546/207; 560/11, 117, 149; 568/28, 34
See application file for complete search history.

(56) References Cited

U.S. PATENT DOCUMENTS

| | | | |
|---|---|---|---|
| 6,548,221 B2 | 4/2003 | Uetani et al. | |
| 6,576,392 B1 * | 6/2003 | Sato et al. .................. | 430/270.1 |
| 6,680,157 B1 | 1/2004 | Fedynyshyn | |
| 6,794,108 B1 * | 9/2004 | Sato et al. .................. | 430/270.1 |
| 6,849,374 B2 * | 2/2005 | Cameron et al. ........... | 430/270.1 |
| 2003/0027061 A1 * | 2/2003 | Cameron et al. ................ | 430/14 |
| 2006/0035165 A1 | 2/2006 | Sasaki | |
| 2009/0023096 A1 | 1/2009 | Tarutani et al. | |
| 2012/0003583 A1 * | 1/2012 | Tsuchimura et al. ...... | 430/283.1 |

FOREIGN PATENT DOCUMENTS

| | | |
|---|---|---|
| EP | 1 480 078 A1 | 11/2000 |
| JP | 10-1508 A | 1/1998 |
| JP | 2001-81138 A | 3/2001 |
| JP | 2004-109834 A | 4/2004 |
| JP | 2004-279471 A | 10/2004 |
| JP | 2005-17730 A | 1/2005 |
| JP | 2005-25150 A | 1/2005 |
| JP | 3912761 B2 | 5/2007 |
| JP | 2009-48182 A | 3/2009 |
| JP | 2009-75425 A | 4/2009 |
| WO | 2009-022681 A1 | 2/2009 |

OTHER PUBLICATIONS

Japanese Office Action issued in application No. 2009-178277 dated Jul. 2, 2013.

\* cited by examiner

*Primary Examiner* — John S Chu
(74) *Attorney, Agent, or Firm* — Sughrue Mion, PLLC

(57) ABSTRACT

An actinic ray- or radiation-sensitive resin composition according to the present invention comprises a sulfonic acid-generating compound that is decomposed by an action of an acid to generate a sulfonic acid having a volume of 240 Å$^3$ or more and a compound that generates the acid when exposed to actinic rays or radiation.

15 Claims, No Drawings

ACTINIC-RAY- OR RADIATION-SENSITIVE RESIN COMPOSITION AND METHOD OF FORMING PATTERN USING THE COMPOSITION

FIELD

The present invention relates to an actinic ray- or radiation-sensitive resin composition whose property is changed when exposed to actinic rays or radiation and a method of forming a pattern using the same. More specifically, the present invention relates to an actinic-ray- or radiation-sensitive resin composition that is suitable for use in a process for producing a semiconductor for an IC or the like, a process for producing a circuit board for a liquid crystal, a thermal head or the like, other photofabrication processes, a process for producing a mold used in an imprint technology, a process for producing a planographic printing plate and as a composition that is hardened by acid, and also relates to a method of forming a pattern using thereof.

In the present invention, the terms "actinic rays" and "radiation" mean, for example, a mercury lamp bright line spectrum, far ultraviolet rays represented by an excimer laser, extreme ultraviolet rays, X-rays, electron beams and the like. In the present invention, the term "light" means actinic rays or radiation.

BACKGROUND

A chemical amplification resist composition is a pattern forming material that is capable of, upon exposure to far ultraviolet or other radiation, generating an acid at the exposed area and, by a reaction catalyzed by the acid, changing the solubility in a developer between the area having been exposed to actinic radiation and the nonexposed area to thereby attain pattern formation on a substrate.

In the use of a KrF excimer laser as an exposure light source, a resin whose fundamental skeleton consists of a poly(hydroxystyrene) exhibiting a low absorption mainly in the region of 248 nm is employed as a major component. Accordingly, there can be attained a high sensitivity, high resolving power and favorable pattern formation. Thus, a system superior to the conventional naphthoquinone diazide/novolak resin system is realized.

On the other hand, in the use of a light source of a further shorter wavelength, for example, an ArF excimer laser (193 nm) as an exposure light source, as the compounds having an aromatic group inherently exhibit a sharp absorption in the region of 193 nm, the above-mentioned chemical amplification system has not been satisfactory.

Therefore, resists for an ArF excimer laser containing a resin with an alicyclic hydrocarbon structure have been developed.

As for a photoacid generator which is a main component of a chemical amplification resist, triphenylsulfonium salt is generally known (see, for example, U.S. Pat. No. 6,548,221).

However, the acid generators above are unsatisfactory in many respects. Thus, there is a demand in the art for the development of a photosensitive composition that is enhanced in the sensitivity, resolution, pattern configuration, roughness characteristic, etc. through the improvement of such acid generators.

In particular, the roughness characteristic and resolution become serious in accordance with the reduction of pattern dimension. Therefore, in the field of, for example, the lithography using X-rays, electron beams or EUV, as the formation of a fine pattern of several tens of nanometers is targeted, the demand for especially high resolution and roughness characteristic is strong.

When use is made of a, light source emitting electron beams, X-rays, EUV or the like, the exposure is carried out in vacuum. This tends to cause low-boiling-point compounds, such as solvents, and resist materials decomposed by high energy to evaporate to thereby dirty the exposure apparatus. This outgas problem is becoming serious. In recent years, various researches have been made on the reduction of the outgas. Various proposals have been made, which include a proposal to inhibit the evaporation of low-molecular compounds by providing a top coat layer (see, for example, European Patent No. 1480078) and a proposal to add a radical trapping agent for the inhibition of polymer decomposition (see, for example, U.S. Pat. No. 6,680,157). For acid generators as well, an ingenuity for outgas reduction is demanded.

Furthermore, Japanese. Patent No. 3912761 proposes a positive photoresist composition for far-ultraviolet exposure which comprises a specified acid-decomposable resin and compound that is decomposed by an action of an acid to generate a sulfonic acid (hereinafter, referred to as sulfonic acid-generating compound) for the purpose of solving the problems of development defect, scumming, etc.

In Japanese. Patent No. 3912761, Paragraph 0016, there is a description that as the acid generated by the sulfonic acid-generating compound, one of high acid strength is preferred. Further, there is a description that a sulfonic acid containing an alkyl group, a cycloalkyl group, an aryl group or an aralkyl group is preferred as the generated acid. In Paragraphs 0017 and 0018 of the reference, as preferred examples of the generated acids, there are mentioned the compounds of general formulae (1) to (5).

DETAILED DESCRIPTION

The present invention will be described below.

Note that, with respect to the expression of a group (or an atomic group) used in this specification, the expression without explicitly referring to whether the group is substituted or unsubstituted encompasses not only groups with no substituents but also groups having one or more substituents. For example, the expression "alkyl group" encompasses not only alkyl groups having no substituents (viz. unsubstituted alkyl groups) but also alkyl groups having one or more substituents (viz. substituted alkyl groups).

The composition according to the present invention comprises a sulfonic acid-generating compound that is decomposed by an action of an acid to generate a sulfonic acid whose volume is 240 Å$^3$ or more [1]; and a compound that generates the acid when exposed to actinic rays or radiation [2] (hereinafter also referred to as a photoacid generator).

In the present invention, the term "volume of an acid" means the volume of a region occupied by a van der Waals sphere based on the van der Waals radii of atoms constituting the acid. In particular, the term "volume of an acid" means the volume calculated in the following manner. Namely, first, the most stable conformation of the acid is determined by a molecular force field calculation using an MM3 method. Thereafter, a van der Waals volume is calculated by a molecular orbital calculation using a PM3 method with respect to this most stable conformation. This van der Waals volume is denoted as the "volume of an acid."

The composition according to the present invention may be used as a positive composition or a negative composition.

In the former instance, the composition of the present invention may further comprise a resin that is decomposed by an action of the acid to increase its solubility in an alkaline developer [3]. Still further, in this instance, the composition of the present invention may further comprise a compound having 3000 or less molecular weight that is decomposed by an action of the acid to increase its solubility in an alkaline developer (the compound hereinafter also referred to as a dissolution inhibiting compound) [5].

In the latter instance, the composition of the present invention may further comprise a resin soluble in an alkaline developer (hereinafter also referred to as an "alkali-soluble resin") [4] and an acid crosslinking agent capable of crosslinking with the alkali-soluble resin under the action of an acid [6].

Moreover, the composition of the present invention may further comprise a basic compound [7], a fluorochemical and/or silicon surfactant [8], an organic solvent [9] and/or other additives [10]. The composition of the present invention may be used for forming a pattern formation performed according to, for example, an embodiment described in the section "method of forming a pattern" [11].

These features [1] to [11] will be described in sequence below.

[1] Sulfonic Acid-Generating Compound

The sulfonic acid-generating compound according to the present invention is decomposed to thereby generate a sulfonic acid whose volume is 240 Å$^3$ or greater when acted on by an acid, or when acted on by an acid and heated.

As aforementioned, the composition of the present invention comprises a sulfonic acid-generating compound and a photoacid generator. Therefore, when the composition of the present invention is exposed to actinic rays or radiation, the photoacid generator generates an acid. At least portion of the sulfonic acid-generating compound contained in the composition is decomposed under the action of the acid generated by the photoacid generator, thereby generating the above sulfonic acid. Further, other portion of the sulfonic acid-generating compound contained in the composition is decomposed under the action of the thus generated sulfonic acid. As a result, the other portion of the sulfonic acid-generating compound further generates the above sulfonic acid.

Accordingly, the sulfonic acid-generating compound according to the present invention functions as an acid amplifier capable of chain acid generation. Therefore, the sensitivity of the actinic ray- or radiation-sensitive resin composition can be enhanced by causing the same to contain the sulfonic acid-generating compound.

The volume of the sulfonic acid generated by the sulfonic acid-generating compound according to the present invention is 240 Å$^3$ or greater. Namely, a bulky group is bonded to the sulfur atom of the sulfonic acid.

By virtue of this feature, any excess diffusion of the sulfonic acid generated by the sulfonic acid-generating compound in the composition can be suppressed. Namely, the use of the sulfonic acid-generating compound suppresses the diffusion of the acid in the composition and facilitates the generation of the acid in desired areas only. Therefore, the resolution and roughness characteristic of the actinic ray- or radiation-sensitive resin composition can be enhanced by containing the sulfonic acid-generating compound. In addition, the sulfo group of the sulfonic acid-generating compound is not susceptible to any attack from nucleophilic species. Therefore, the aging stability of the composition can be enhanced by using this sulfonic acid-generating compound.

As the sulfonic acid whose volume is 240 Å$^3$ or greater generated by the sulfonic acid-generating compound, there can be mentioned, for example, the following. Hereinafter, this sulfonic acid is expressed by the formula A-SO$_3$H. Namely, the residue of the sulfonic acid is represented by the character A below.

The residue A is an alkyl group, a cycloalkyl group or an aromatic group. A substituent, may be introduced in each of the alkyl group, cycloalkyl group and aromatic group.

This alkyl group preferably has 1 to 30 carbon atoms. As such an alkyl group, there can be mentioned, for example, a methyl group, an ethyl group, a propyl group, a butyl group, a pentyl group, a hexyl group, a heptyl group, an octyl group, a nonyl group, a decyl group, a dodecyl group, a tetradecyl group, an octadecyl group, an isopropyl group, an isobutyl group, a sec-butyl group, a t-butyl group, a 1-ethylpentyl group or a 2-ethylhexyl group.

The cycloalkyl group may be a monocycloalkyl group or a polycycloalkyl group. As the monocycloalkyl group, there can be mentioned, for example, a cyclopropyl group, a cyclobutyl group, a cyclopentyl group, a cyclohexyl group, a cycloheptyl group or a cyclooctyl group. As the polycycloalkyl group, there can be mentioned, for example, an adamantyl group, a norbornyl group, a bornyl group, a camphenyl group, a decahydronaphthyl group, a tricyclodecanyl group, a tetracyclodecanyl group, a camphoroyl group, a dicyclohexyl group or a pinenyl group.

The aromatic group is, for example, a benzene ring, a naphthalene ring, a pentalene ring, an indene ring, an azulene ring, a heptalene ring, an indecene ring, a perylene ring, a pentacene ring, an acenaphthalene ring, a phenanthrene ring, an anthracene ring, a naphthacene ring, a chrysene ring, a triphenylene ring, a fluorene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring or a phenazine ring. Of these, a benzene ring, a naphthalene ring and an anthracene ring are preferred from the viewpoint of the simultaneous attainment of roughness and sensitivity enhancements. A benzene ring is more preferred.

As examples of the substituents that can be introduced in the alkyl group, cycloalkyl group and aromatic group, there can be mentioned a halogen atom such as a fluorine atom, a chlorine atom, a bromine atom or an iodine atom; an alkoxy group such as a methoxy group, an ethoxy group or a tert-butoxy group; an aryloxy group such as a phenoxy group or a p-tolyloxy group; an alkoxy- or aryloxycarbonyl group such as a methoxycarbonyl group, a butoxycarbonyl group or a phenoxycarbonyl group; an acyloxy group such as an acetoxy group, a propionyloxy group or a benzoyloxy group; an acyl group such as an acetyl group, a benzoyl group, a isobutyryl group, an acryloyl group, a methacryloyl group or a methoxalyl group; an alkylsulfanyl group such as a methylsulfanyl group or a tert-butylsulfanyl group; an arylsulfanyl group such as a phenylsulfanyl group or a p-tolylsulfanyl group; an alkyl group such as a methyl group, an ethyl group, a tert-butyl group or a dodecyl group; an aryl group such as a phenyl group, a p-tolyl group, a xylyl group, a cumenyl group, a naphthyl group, an anthryl group or a phenanthryl group; a hydroxyl group; a carboxyl group; a formyl group; a sulfonyl group; a cyano group; an alkylaminocarbonyl group; an arylaminocarbonyl group; a sulfonamido group; a silyl group; an amino group; a thioxy group; and combinations of these.

The residue A preferably has a cyclic structure. More preferably, the sulfonic acid A-SO₃H is any of the compounds of general formulae (6) and (7) below. Further more preferably, the sulfonic acid A-SO₃H is any of the compounds of general formula (6) below.

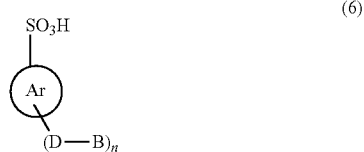

(6)

In formula (6),

Ar represents an aryl group, in which a substituent other than the -(D-B) group may further be introduced; and n is an integer of 1 or greater, preferably 1 to 4, more preferably 2 or 3, and most preferably 3.

D represents a single bond or a bivalent connecting group. This bivalent connecting group is an ether group, a thioether group, a carbonyl group, a sulfoxide group, a sulfon group, a sulfonic ester group or an ester group.

B represents a hydrocarbon group.

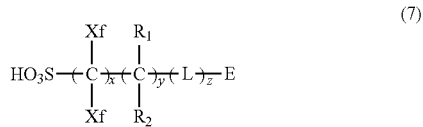

(7)

In formula (7), each of Xf's independently represents a fluorine atom or an alkyl group substituted with at least one fluorine atom.

Each of $R_1$ and $R_2$ independently represents a group selected from the group consisting of a hydrogen atom, a fluorine atom, an alkyl group and an alkyl group substituted with at least one fluorine atom, provided that a plurality of $R_1$s or $R_2$s may be identical to or different from each other.

L represents a single bond or a bivalent connecting group, provided that a plurality of L's may be identical to or different from each other.

E represents a group with a cyclic structure; and x is an integer of 1 to 20, preferably 1 to 4; y is an integer of 0 to 10, preferably 0 to 3; and z is an integer of 0 to 10, preferably 0 to 3.

First, the sulfonic acids of formula (6) will be described in detail below.

In formula (6), Ar is preferably an aromatic ring having 6 to 30 carbon atoms. In particular, Ar is, for example, a benzene ring, a naphthalene ring, a pentalene ring, an indene ring, an azulene ring, a heptalene ring, an indecene ring, a perylene ring, a pentacene ring, an acenaphthalene ring, a phenanthrene ring, an anthracene ring, a naphthacene ring, a chrysene ring, a triphenylene ring, a fluorene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring or a phenazine ring. Of these, a benzene ring, a naphthalene ring and an anthracene ring are preferred from the viewpoint of the simultaneous attainment of roughness and sensitivity enhancements. A benzene ring is more preferred.

When a substituent other than the -(D-B) group is further introduced in Ar, the substituent is, for example, as follows. Namely, as the substituent, there can be mentioned a halogen atom such as a fluorine atom, a chlorine atom, a bromine atom or an iodine atom; an alkoxy group such as a methoxy group, an ethoxy group or a tert-butoxy group; an aryloxy group such as a phenoxy group or a p-tolyloxy group; an alkylthioxy group such as a methylthioxy group, an ethylthioxy group or a tert-butylthioxy group; an arylthioxy group such as a phenylthioxy group or a p-tolylthioxy group; an alkoxy- or aryloxycarbonyl group such as a methoxycarbonyl group, a butoxycarbonyl group or a phenoxycarbonyl group; an acetoxy group; a linear or branched alkyl group such as a methyl group, an ethyl group, a propyl group, a butyl group, a heptyl group, hexyl group, a dodecyl group or a 2-ethylhexyl group; an alkenyl group such as a vinyl group, a propenyl group or a hexenyl group; an alkynyl group such as an acetylene group, a propynyl group or a hexynyl group; an aryl group such as a phenyl group or a tolyl group; a hydroxyl group; a carboxyl group; or a sulfonic acid group. Of these, a linear or branched alkyl group is preferred from the viewpoint of roughness improvement.

In formula (6), D is preferably a single bond or an ether or ester group. More preferably, D is a single bond.

In formula (6), B is, for example, an alkyl group, an alkenyl group, an alkynyl group, an aryl group or a cycloalkyl group. B is preferably an alkyl group or a cycloalkyl group. A substituent may be introduced in each of the alkyl group, alkenyl group, alkynyl group, aryl group and cycloalkyl group represented by B.

The alkyl group represented by B is preferably a branched alkyl group. As the branched alkyl group, there can be mentioned, for example, an isopropyl group, a tert-butyl group, a tert-pentyl group, a neopentyl group, a sec-butyl group, an isobutyl group, an isohexyl group, a 3,3-dimethylpentyl group or a 2-ethylhexyl group.

The cycloalkyl group represented by B may be a monocycloalkyl group or a polycycloalkyl group. As the monocycloalkyl group, there can be mentioned, for example, a cyclopropyl group, a cyclobutyl group, a cyclopentyl group, a cyclohexyl group, a cycloheptyl group or a cyclooctyl group. As the polycycloalkyl group, there can be mentioned, for example, an adamantyl group, a norbornyl group, a bornyl group, a camphenyl group, a decahydronaphthyl group, a tricyclodecanyl group, a tetracyclodecanyl group, a camphoroyl group, a dicyclohexyl group or a pinenyl group.

When a substituent is introduced in each of the alkyl group, alkenyl group, alkynyl group, aryl group and cycloalkyl group represented by B, the substituent is, for example, as follows. Namely, as the substituent, there can be mentioned a halogen atom such as a fluorine atom, a chlorine atom, a bromine atom or an iodine atom; an alkoxy group such as a methoxy group, an ethoxy group or a tert-butoxy group; an aryloxy group such as a phenoxy group or a p-tolyloxy group; an alkylthioxy group such as a methylthioxy group, an ethylthioxy group or a tert-butylthioxy group; an arylthioxy group such as a phenylthioxy group or a p-tolylthioxy group; an alkoxy- or aryloxycarbonyl group such as a methoxycarbonyl group, a butoxycarbonyl group or a phenoxycarbonyl group; an acetoxy group; a linear or branched alkyl group such as a methyl group, an ethyl group, a propyl group, a butyl group, a heptyl group, a hexyl group, a dodecyl group or a 2-ethylhexyl group; a cycloalkyl group such as a cyclohexyl group; an alkenyl group such as a vinyl group, a propenyl group or a hexenyl group; an alkynyl group such as an acetylene group, a propynyl group or a hexynyl group; an aryl group such as a phenyl group or a tolyl group; a hydroxyl group; a carboxyl group; a sulfonic acid group; a carbonyl group; or the like. Of these, a linear or branched alkyl group is preferred from the viewpoint of the simultaneous attainment of roughness and sensitivity enhancements.

Now, the sulfonic acids of formula (7) will be described in detail below.

In formula (7), Xf represents a fluorine atom or an alkyl group substituted with at least one fluorine atom. This alkyl group preferably has 1 to 10 carbon atoms, more preferably 1 to 4 carbon atoms. The alkyl group substituted with a fluorine atom is preferably a perfluoroalkyl group.

Xf is preferably a fluorine atom or a perfluoroalkyl group having 1 to 4 carbon atoms. In particular, Xf is preferably a fluorine atom, $CF_3$, $C_2F_5$, $C_3F_7$, $C_4F_9$, $C_5F_{11}$, $C_6F_{13}$, $C_7F_{15}$, $C_3F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ or $CH_2CH_2C_4F_9$. Of these, a fluorine atom and $CF_3$ are preferred. A fluorine atom is most preferred.

In formula (7), each of $R_1$ and $R_2$ represents a group selected from the group consisting of a hydrogen atom, a fluorine atom, an alkyl group and an alkyl group substituted with at least one fluorine atom. The alkyl group optionally substituted with a fluorine atom preferably has 1 to 4 carbon atoms. The alkyl group substituted with a fluorine atom is most preferably a perfluoroalkyl group having 1 to 4 carbon atoms. In particular, there can be mentioned $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ or $CH_2CH_2C_4F_9$. Of these, $CF_3$ is preferred.

In formula (7), x is preferably 1 to 8, more preferably 1 to 4; y is preferably 0 to 4, more preferably 0; and z is preferably 0 to 8, more preferably 0 to 4.

In formula (7), L represents a single bond or a bivalent connecting group. As the bivalent connecting group, there can be mentioned, for example, —COO—, —COO—, —CO—, —O—, —S—, —SO—, —SO$_2$—, an alkylene group, a cycloalkylene group or an alkenylene group. Of these, —COO—, —COO—, —CO—, —O—, —S—, —SO— and —SO$_2$— are preferred. —COO—, —COO— and —SO$_2$— are more preferred.

In formula (7), E represents a group with a cyclic structure. E is, for example, a cycloaliphatic group, an aryl group, a group with a heterocyclic structure or the like.

The cycloaliphatic group represented by E may have a monocyclic structure or a polycyclic structure. The cycloaliphatic group with a monocyclic structure is preferably a monocycloalkyl group, such as a cyclopentyl group, a cyclohexyl group or a cyclooctyl group. The cycloaliphatic group with a polycyclic structure is preferably a polycycloalkyl group, such as a norbornyl group, a tricyclodecanyl group, a tetracyclodecanyl group, a tetracyclododecanyl group or an adamantyl group. In particular, when a cycloaliphatic group with a bulky structure of 6 or more-membered ring is employed as E, any in-film diffusion in the PEB (post-exposure bake) operation can be suppressed, and the resolution and EL (exposure latitude) can be enhanced.

The aryl group represented by E is, for example, a benzene ring, a naphthalene ring, a phenanthrene ring or an anthracene ring.

It is optional for the group with a heterocyclic structure represented by E to have aromaticity. The heteroatom contained in this group is preferably a nitrogen atom or an oxygen atom. As particular examples of the heterocyclic structures, there can be mentioned a furan ring, a thiophene ring, a benzofuran ring, a benzothiophene ring, a dibenzofuran ring, a dibenzothiophene ring, a pyridine ring, a piperidine ring, a morpholine ring and the like. Of these, a furan ring, a thiophene ring, a pyridine ring, a piperidine ring and a morpholine ring are preferred.

A substituent may be introduced in E. As the substituent, there can be mentioned, for example, an alkyl group (may be any of linear, branched and cyclic forms, preferably having 1 to 12 carbon atoms), an aryl group (preferably having 6 to 14 carbon atoms), a hydroxyl group, an alkoxy group, an ester group, an amido group, a urethane group, a ureido group, a thioether group, a sulfonamido group or a sulfonic ester group.

Examples of the sulfonic acids $ASO_3H$ each having a volume of 240 Å$^3$ or greater will be shown below.

For each of the examples, the calculated volume is indicated thereby.

The value of each of the volumes was determined by means of the software "WinMOPAC" compiled by Fujitsu Limited in the following manner. First, the chemical structure of the acid according to each of the examples was inputted. Subsequently, while regarding this structure as an initial structure, the most stable conformation of the acid was determined by a molecular force field calculation using an MM3 method. Thereafter, a molecular orbital calculation using a PM3 method was carried out with respect to the most stable conformation. Thus, the "accessible volume" of each of the acids was determined.

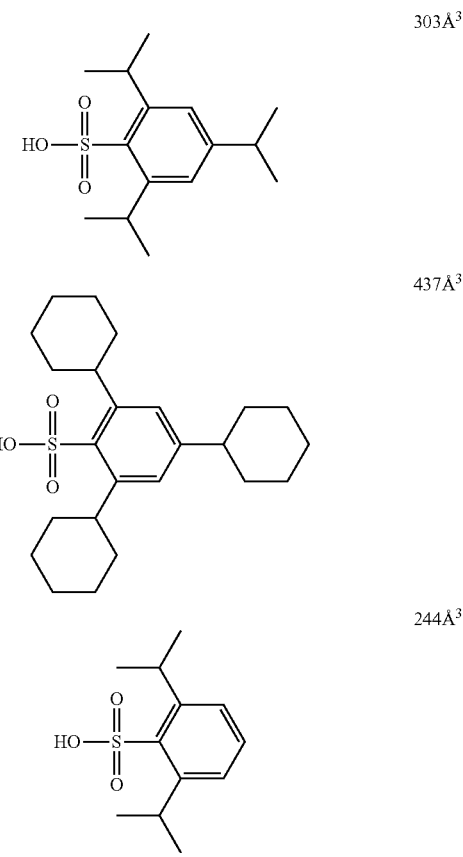

529Å³
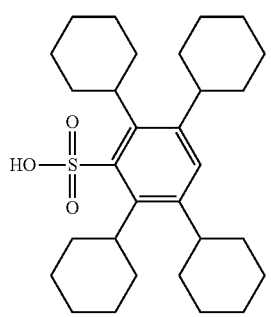
357Å³
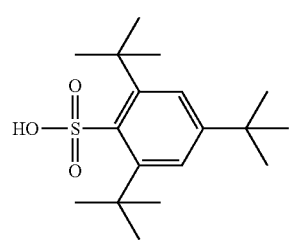
280Å³
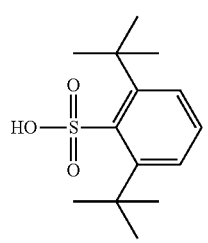
336Å³
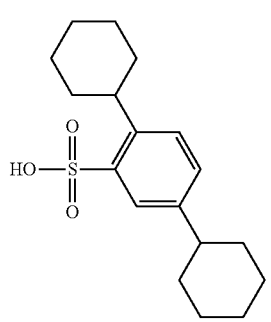
244Å³
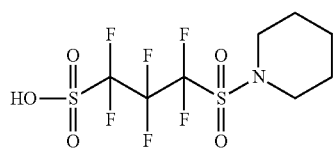
271Å³
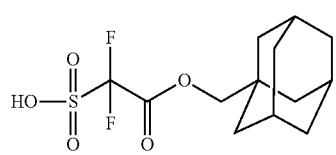
380Å³
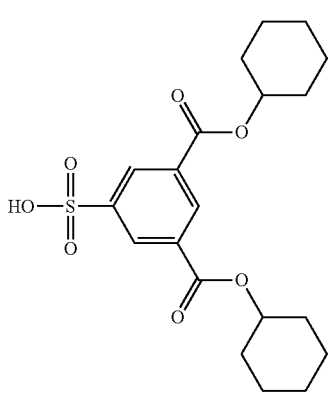
277Å³
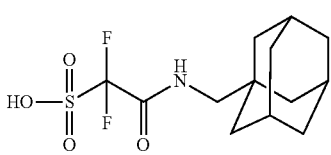
347Å³
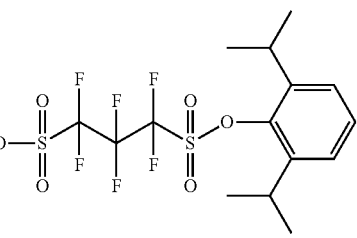
457Å³
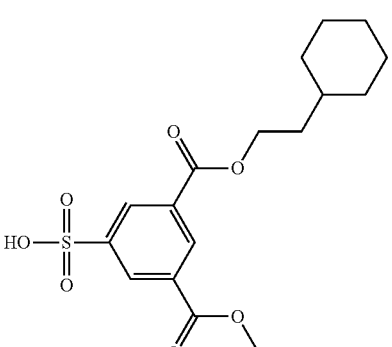

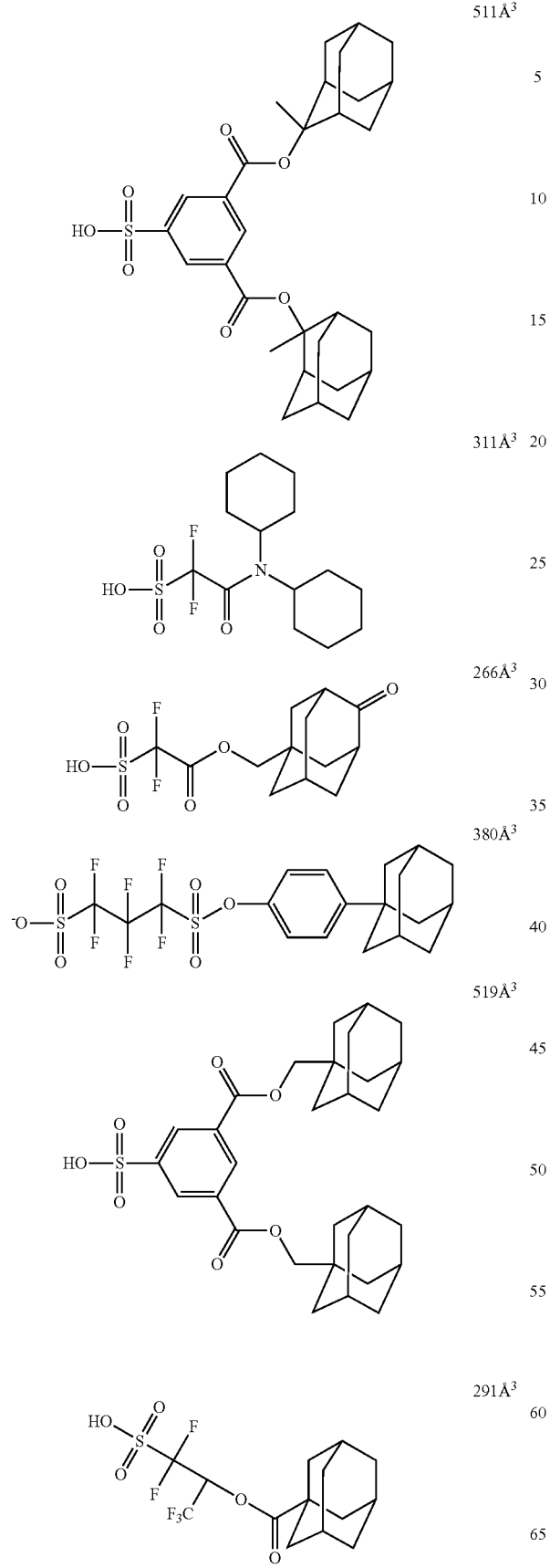

The volume of the sulfonic acid $ASO_3H$ is preferably 300 Å$^3$ or greater, more preferably 400 Å$^3$ or greater. Further, the volume is preferably up to 2000 Å$^3$, more preferably up to 1500 Å$^3$. An excess increase of the volume may lead to a deterioration of the sensitivity and/or coating solvent solubility.

The sulfonic acid-generating compound capable of generating the above sulfonic acid $ASO_3H$ is a compound containing at least one group expressed by $ASO_3$—.

As the sulfonic acid-generating compound, use is made of, for example, any of the compounds of general formulae (1) to (5) below. Preferably, the compounds of general formula (1) below are used as the sulfonic acid-generating compounds.

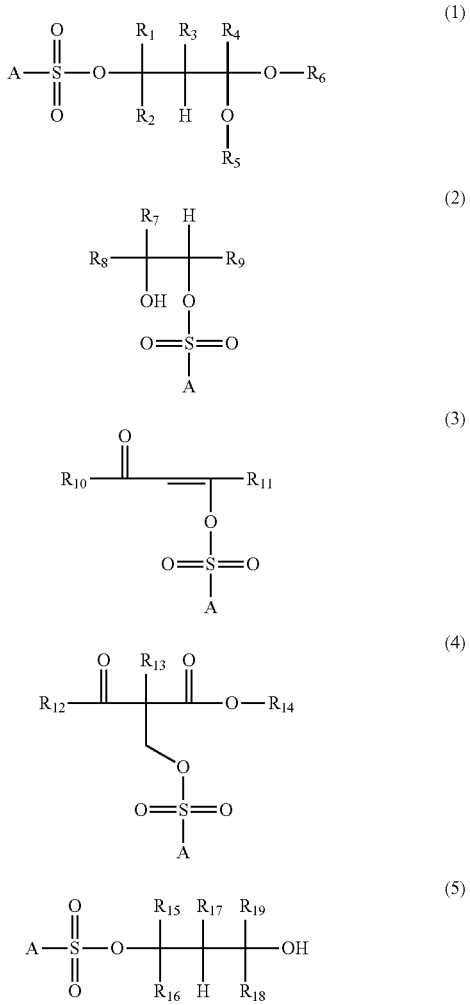

In the formulae, each of $R_1$ to $R_4$, $R_7$ to $R_{13}$ and $R_{15}$ to $R_{19}$ represents a hydrogen atom or a monovalent substituent. Each of $R_5$, $R_6$ and $R_{14}$ represents a monovalent substituent. A represents a residue of the sulfonic acid expressed by the formula $A$-$SO_3H$.

A plurality of groups expressed by $ASO_3$— may be introduced in each of the compounds of general formulae (1) to (5). Namely, a plurality of structures capable of generating the sulfonic acid $A$-$SO_3H$ may be introduced in each molecule of each of the compounds of general formulae (1) to (5).

The compounds of general formula (1) will be described in detail below.

First, $R_1$ to $R_4$ will be described.

In formula (1), each of $R_1$ to $R_4$ represents a hydrogen atom or a monovalent substituent.

As the monovalent substituent, there can be mentioned, for example, an alkyl group, a cycloalkyl group, an alkenyl group, an alkynyl group, an aryl group, a halogen atom, an alkoxy group, an aryloxy group, an alkanoyl group, an alkoxycarbonyl group, an aryloxycarbonyl group, an alkylsulfonyloxy group, an arylsulfonyloxy group, an alkylsulfonyl group, an arylsulfonyl group, a cyano group, an alkylthioxy group, an arylthioxy group or a heterocyclic group. Substituents may be introduced in, among them, an alkyl group, a cycloalkyl group, an alkenyl group, an alkynyl group, an aryl group, an alkoxy group, an aryloxy group, an alkanoyl group, an alkoxycarbonyl group, an aryloxycarbonyl group, an alkylsulfonyloxy group, an arylsulfonyloxy group, an alkylsulfonyl group, an arylsulfonyl group, a cyano group, an alkylthioxy group, an arylthioxy group and a heterocyclic group.

The alkyl group is preferably an alkyl group having 1 to 30 carbon atoms. As such, there can be mentioned, for example, a methyl group, an ethyl group, a propyl group, a butyl group, a hexyl group, an octyl group, a decyl group, a dodecyl group, an octadecyl group, an isopropyl group, an isobutyl group, a sec-butyl group, a t-butyl group, a 1-ethylpentyl group, a trifluoromethyl group, a 2-ethylhexyl group, a phenacyl group, a 1-naphthoylmethyl group, a 2-naphthoylmethyl group, a 4-methylsulfanylphenacyl group, a 4-phenylsulfanylphenacyl group, a 4-dimethylaminophenacyl group, a 4-cyanophenacyl group, a 4-methylphenacyl group, a 2-methylphenacyl group, a 3-fluorophenacyl group, a 3-trifluoromethylphenacyl group or a 3-nitrophenacyl group.

The cycloalkyl group may have a monocyclic structure or polycyclic structure. The cycloalkyl group with a monocyclic structure is preferably a cyclopentyl group, a cyclohexyl group, a cyclooctyl group or the like. The cycloalkyl group with a polycyclic structure is preferably a norbornyl group, a tricyclodecanyl group, a tetracyclodecanyl group, a tetracyclododecanyl group, an adamantyl group or the like. Cycloalkyl groups each having 3 to 8 carbon atoms are preferred. For example, a cyclopentyl group and a cyclohexyl group are more preferred.

The alkenyl group is preferably one having 2 to 10 carbon atoms. As such, there can be mentioned, for example, a vinyl group, an allyl group, a styryl group or the like.

The alkynyl group is preferably one having 2 to 10 carbon atoms. As such, there can be mentioned, for example, an ethynyl group, a propynyl group, a propargyl group or the like.

The aryl group is preferably one having 6 to 30 carbon atoms. As such, there can be mentioned, for example, a phenyl group, a biphenyl group, a 1-naphthyl group, a 2-naphthyl group, a 9-anthryl group, a 9-phenanthryl group, a 1-pyrenyl group, a 5-naphthacenyl group, a 1-indenyl group, a 2-azulenyl group, a 9-fluorenyl group, a terphenyl group, a quaterphenyl group, an o-, m- or p-tolyl group, a xylyl group, an o-, m- or p-cumenyl group, a mesityl group, a pentalenyl group, a binaphthalenyl group, a ternaphthalenyl group, a quaternaphthalenyl group, a heptalenyl group, a biphenylenyl group, an indacenyl group, a fluoranthenyl group, an acenaphthylenyl group, an aceanthrylenyl group, a phenalenyl group, a fluorenyl group, an anthryl group, a bianthracenyl group, a teranthracenyl group, a quateranthracenyl group, an anthraquinolyl group, a phenanthryl group, a triphenylenyl group, a pyrenyl group, a chrysenyl group, a naphthacenyl group, a pleiadenyl group, a picenyl group, a perylenyl group, a pentaphenyl group, a pentacenyl group, a tetraphenylenyl group, a hexaphenyl group, a hexacenyl group, a rubicenyl group; a coronenyl group, a trinaphthylenyl group, a heptaphenyl group, heptacenyl group, a pyranthrenyl group or an ovalenyl group.

As the halogen atom, there can be mentioned a fluorine atom, a chlorine atom, a bromine atom or an iodine atom.

As the alkoxy group, there can be mentioned, for example, a methoxy group, an ethoxy group, a propoxy group, an n-butoxy group, a trifluoromethoxy group, a hexyloxy group, a t-butoxy group, a 2-ethylhexyloxy group, a cyclohexyloxy group, a decyloxy group or a dodecyloxy group.

As the aryloxy group, there can be mentioned, for example, a phenyloxy group, a 1-naphthyloxy group, a 2-naphthyloxy group, a tolyloxy group, a methoxyphenyloxy group, a naphthyloxy group, a chlorophenyloxy group, a trifluoromethylphenyloxy group, a cyanophenyloxy group or a nitrophenyloxy group.

The alkanoyl group is preferably one having 2 to 20 carbon atoms. As such, there can be mentioned, for example, an acetyl group, a propanoyl group, a butanoyl group, a trifluoromethylcarbonyl group, a pentanoyl group, a benzoyl group, a 1-naphthoyl group, a 2-naphthoyl group, a 4-methylsulfanylbenzoyl group, a 4-phenylsulfanylbenzoyl group, a 4-dimethylaminobenzoyl group, a 4-diethylaminobenzoyl group, a 2-chlorobenzoyl group, a 2-methylbenzoyl group, a 2-methoxybenzoyl group, a 2-butoxybenzoyl group, a 3-chlorobenzoyl group, a 3-trifluoromethylbenzoyl group a 3-cyanobenzoyl group, a 3-nitrobenzoyl group, a 4-fluorobenzoyl group, a 4-cyanobenzoyl group or a 4-methoxybenzoyl group.

The alkoxycarbonyl group is preferably one having 2 to 20 carbon atoms. As such, there can be mentioned, for example, a methoxycarbonyl group, an ethoxycarbonyl group, a propoxycarbonyl group, a butoxycarbonyl group, a hexyloxycarbonyl group, an octyloxycarbonyl group, a decyloxycarbonyl group, an octadecyloxycarbonyl group or a trifluoromethyloxycarbonyl group.

As the aryloxycarbonyl group, there can be mentioned, for example, a phenoxycarbonyl group, a 1-naphthyloxycarbonyl group, a 2-naphthyloxycarbonyl group, a 4-methylsulfanylphenyloxycarbonyl group, a 4-phenylsulfanylphenyloxycarbonyl group, a 4-dimethylaminophenyloxycarbonyl group, a 4-diethylaminophenyloxycarbonyl group, a 2-chlorophenyloxycarbonyl group, a 2-methylphenyloxycarbonyl group, a 2-methoxyphenyloxycarbonyl group, a 2-butoxyphenyloxycarbonyl group, a 3-chlorophenyloxycarbonyl group, a 3-trifluoromethylphenyloxycarbonyl group, a 3-cyanophenyloxycarbonyl group, a 3-nitrophenyloxycarbonyl group, a 4-fluorophenyloxycarbonyl group, a 4-cyanophenyloxycarbonyl group or a 4-methoxyphenyloxycarbonyl group.

The alkylsulfonyloxy group is preferably one having 1 to 20 carbon atoms. As such, there can be mentioned, for example, a methylsulfonyloxy group, an ethylsulfonyloxy group, a propylsulfonyloxy group, an isopropylsulfonyloxy group, a butylsulfonyloxy group, a hexylsulfonyloxy group, a cyclohexylsulfonyloxy group, an octylsulfonyloxy group, a 2-ethylhexylsulfonyloxy group, a decanoylsulfonyloxy group, a dodecanoylsulfonyloxy group, an octadecanoylsulfonyloxy group, a cyanomethylsulfonyloxy group, a methoxymethylsulfonyloxy group or a perfluoroalkylsulfonyloxy group.

The arylsulfonyloxy group is preferably one having 6 to 30 carbon atoms. As such, there can be mentioned, for example, a phenylsulfonyloxy group, a 1-naphthylsulfonyloxy group, a 2-naphthylsulfonyloxy group, a 2-chlorophenylsulfonyloxy group, a 2-methylphenylsulfonyloxy group, a 2-methoxyphenylsulfonyloxy group, a 2-butoxyphenylsulfonyloxy group, a 3-chlorophenylsulfonyloxy group, a 3-trifluoromethylphenylsulfonyloxy group, a 3-cyanophenylsulfonyloxy group, a 3-nitrophenylsulfonyloxy group, a 4-fluorophenylsulfonyloxy group, a 4-cyanophenylsulfonyloxy group, a 4-methoxyphenylsulfonyloxy group, a 4-methylsulfanylphenylsulfonyloxy group, a 4-phenylsulfanylphenylsulfonyloxy group or a 4-dimethylaminophenylsulfonyloxy group.

The alkylsulfonyl group is preferably one having 1 to 20 carbon atoms. As such, there can be mentioned, for example, a methylsulfonyl group, an ethylsulfonyl group, a propylsulfonyl group, an isopropylsulfonyl group, a butylsulfonyl group, a hexylsulfonyl group, a cyclohexylsulfonyl group, an octylsulfonyl group, a 2-ethylhexylsulfonyl group, a decanoylsulfonyl group, a dodecanoylsulfonyl group, an octadecanoylsulfonyl group, a cyanomethylsulfonyl group, a methoxymethylsulfonyl group or a perfluoroalkylsulfonyl group.

The arylsulfonyl group is preferably one having 6 to 30 carbon atoms. As such, there can be mentioned, for example, a phenylsulfonyl group, a 1-naphthylsulfonyl group, a 2-naphthylsulfonyl group, a 2-chlorophenylsulfonyl group, a 2-methylphenylsulfonyl group, a 2-methoxyphenylsulfonyl group, a 2-butoxyphenylsulfonyl group, a 3-chlorophenylsulfonyl group, a 3-trifluoromethylphenylsulfonyl group, a 3-cyanophenylsulfonyl group, a 3-nitrophenylsulfonyl group, a 4-fluorophenylsulfonyl group, a 4-cyanophenylsulfonyl group, a 4-methoxyphenylsulfonyl group, a 4-methylsulfanylphenylsulfonyl group, a 4-phenylsulfanylphenylsulfonyl group or a 4-dimethylaminophenylsulfonyl group.

As the alkylthioxy group, there can be mentioned, for example, a methylthioxy group, an ethylthioxy group, a propylthioxy group, an n-butylthioxy group, a trifluoromethylthioxy group, a hexylthioxy group, a t-butylthioxy group, a 2-ethylhexylthioxy group, a cyclohexylthioxy group, a decylthioxy group or a dodecylthioxy group.

As the arylthioxy group, there can be mentioned, for example, a phenylthioxy group, a 1-naphthylthioxy group, a 2-naphthylthioxy group, a tolylthioxy group, a methoxyphenylthioxy group, a naphthylthioxy group, a chlorophenylthioxy group, a trifluoromethylphenylthioxy group, a cyanophenylthioxy group or a nitrophenylthioxy group.

The heterocyclic group is preferably an aromatic or aliphatic heterocycle containing a nitrogen atom, an oxygen atom, a sulfur atom or a phosphorus atom. As the heterocyclic group, there can be mentioned, for example, a thienyl group, a benzo[b]thienyl group, a naphtho[2,3-b]thienyl group, a thianthrenyl group, a furyl group, a pyranyl group, an isobenzofuranyl group, a chromenyl group, a xanthenyl group, a phenoxathiyl group, a 2H-pyrrolyl group, a pyrrolyl group, an imidazolyl group, a pyrazolyl group, a pyridyl group, a pyrazinyl group, a pyrimidinyl group, a pyridazinyl group, an indolizinyl group, an isoindolyl group, a 3H-indolyl group, an indolyl group, a 1H-indazolyl group, a purinyl group, a 4H-quinolizinyl group, an isoquinolyl group, a quinolyl group, a phthalazinyl group, a naphthyridinyl group, a quinoxalinyl group, a quinazolinyl group, a cinnolinyl group, a puteridinyl group, a 4aH-carbazolyl group, a carbazolyl group, a β-carbolinyl group, a phenanthridinyl group, an acridinyl group, a perimidinyl group, a phenanthrolinyl group, a phenazinyl group, a phenarsazinyl group, an isothiazolyl group, a phenothiazinyl group, an isoxazolyl group, a furazanyl group, a phenoxadinyl group, an isochromanyl group, a chromanyl group, a pyrrolidinyl group, a pyrrolinyl group, an imidazolidinyl group, an imidazolinyl group, a pyrazolidinyl group, a pyrazolinyl group, a piperidyl group, a piperazinyl group, an indolinyl group, an isoindolinyl group, a quinucridinyl group, a morpholinyl or a thioxanthryl group.

As the substituents that can be introduced in any of $R_1$ to $R_4$, there can be mentioned, for example, a halogen atom such as a fluorine atom, a chlorine atom, a bromine atom or an iodine atom; an alkoxy group such as a methoxy group, an ethoxy group or a tert-butoxy group; an aryloxy group such as a phenoxy group or a p-tolyloxy group; an alkoxy- or aryloxycarbonyl group such as a methoxycarbonyl group, a butoxycarbonyl group or a phenoxycarbonyl group; an acyloxy group such as an acetoxy group, a propionyloxy group or a benzoyloxy group; an acyl group such as an acetyl group, a benzoyl group, a isobutyryl group, an acryloyl group, a methacryloyl group or a methoxalyl group; an alkylsulfanyl group such as a methylsulfanyl group or a tert-butylsulfanyl group; an arylsulfanyl group such as a phenylsulfanyl group or a p-tolylsulfanyl group; an alkylamino group such as a methylamino group or a cyclohexylamino group; a dialkylamino group such as a dimethylamino group, a diethylamino group, a morpholino group or a piperidino group; an arylamino group such as a phenylamino group or a p-tolylamino group; an alkyl group such as a methyl group, an ethyl group, a tert-butyl group or a dodecyl group; an aryl group such as a phenyl group, a p-tolyl group, a xylyl group, a cumenyl group, a naphthyl group, an anthryl group or a phenanthryl group; a hydroxyl group; a carboxyl group; a formyl group; a mercapto group; a sulfo group; a mesyl group; a p-toluenesulfonyl group; an amino group; a nitro group; a cyano group; a trifluoromethyl group; a trichloromethyl group; a trimethylsilyl group; a phosphinico group; a phosphono group; a trimethylammoniumyl group; a dimethylsulfoniumyl group; and a triphenylphenancylphosphoniumyl group.

Two or more of $R_1$ to $R_4$ may be bonded to each other to thereby form a cyclic structure. This cyclic structure may be an aliphatic or aromatic hydrocarbon ring, or a heterocycle containing a heteroatom. These $R_1$ to $R_4$ may also form a polycondensed ring.

As the aliphatic or aromatic hydrocarbon ring, there can be mentioned, for example, one with a 6-membered, 5-membered or 7-membered ring structure. As the hydrocarbon ring, one with a 6-membered or 5-membered ring structure is preferred. One with a 5-membered ring structure is most preferred.

As the heterocycle, there can be mentioned, for example, one containing a sulfur atom, an oxygen atom or a nitrogen atom as a heteroatom. It is preferred for the heterocycle to be one containing a sulfur atom as a heteroatom.

As the polycondensed ring, there can be mentioned, for example, a condensed ring composed only of hydrocarbon rings. As such a polycondensed ring, there can be mentioned, for example, one resulting from the condensation of 2 to 4 benzene rings or one resulting from the condensation of a benzene ring with a 5-membered unsaturated ring.

The polycondensed ring may be a condensed ring containing at least one heterocycle. As such a polycondensed ring, there can be mentioned, for example, one resulting from the condensation of a benzene ring with a 5-membered heterocycle or one resulting from the condensation of a benzene ring with a 6-membered heterocycle.

As the cyclic structure that can be formed by $R_1$ to $R_4$, there can be mentioned, for example, a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, a dithiorane ring, an oxirane ring, a dioxirane ring, a thiirane ring, a pyrrolidine ring, a piperidine ring, an imidazole ring, an isooxazole ring, a benzothiazole ring, an oxazole ring, a thiazole ring, a benzothiazole ring, a benzimidazole ring, a benzoxazole ring, a pyridine ring, a pyrazine ring, a pyrimidine ring, a pyridazine ring, an indolizine ring, an indole ring, a benzofuran ring, a benzothiophene ring, a benzodithiol ring, an isobenzofuran ring, a quinolizine ring, a quinoline ring, a phthalazine ring, a naphthyridine ring, a quinoxaline ring, a quinazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring or a phenazine ring. Of these, a dithiorane ring, a benzodithiol ring, a benzothiazole ring, a benzimidazole ring and a benzoxazole ring are especially preferred.

The characters $R_1$ to $R_4$ used in general formula (1) mean, for example, those groups appearing in the following chemical formulae.

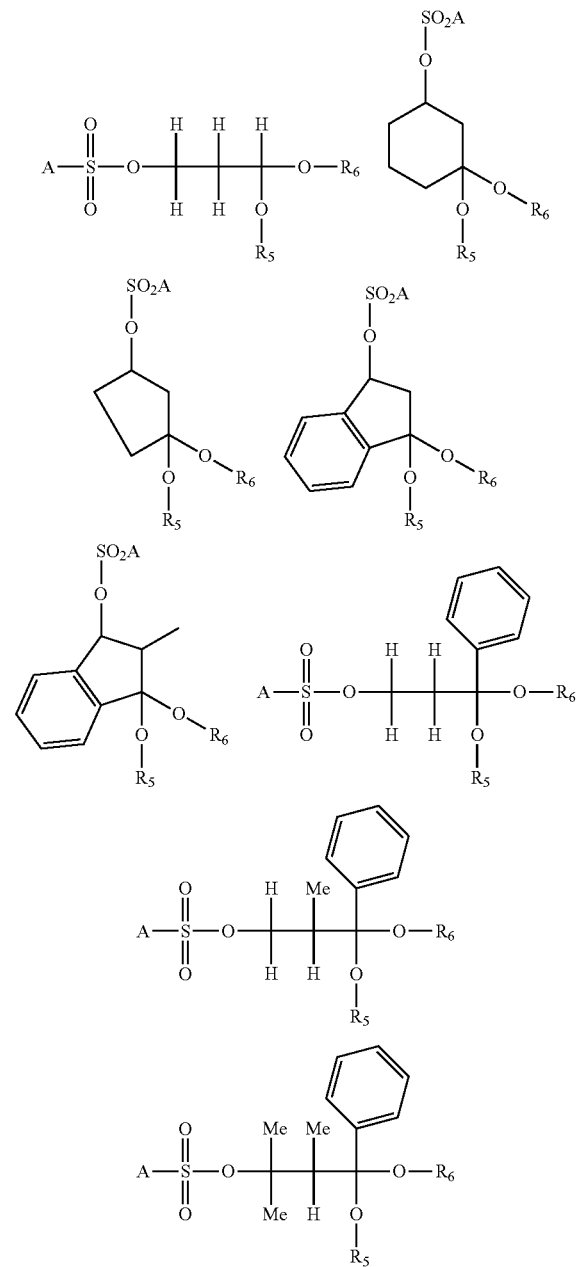

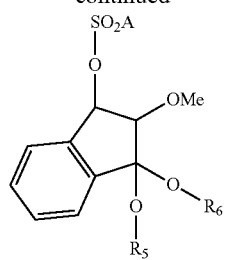
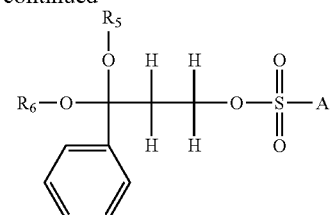
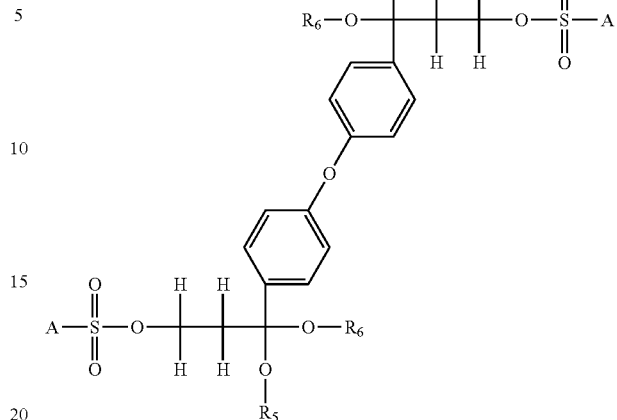
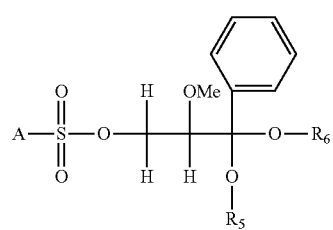
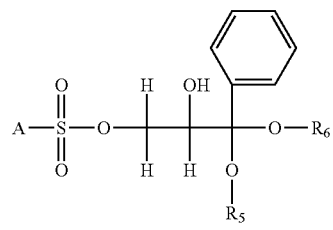
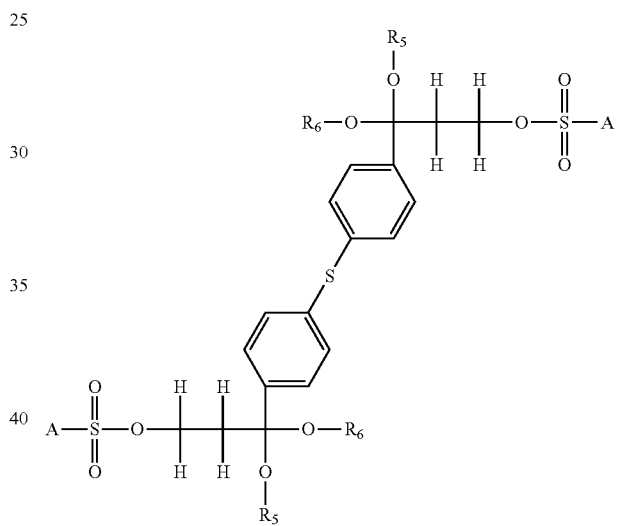
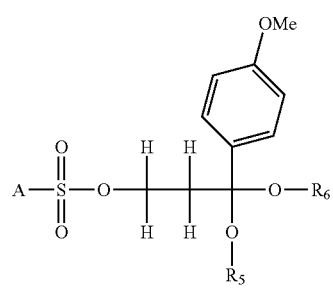
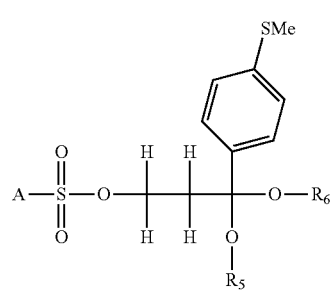
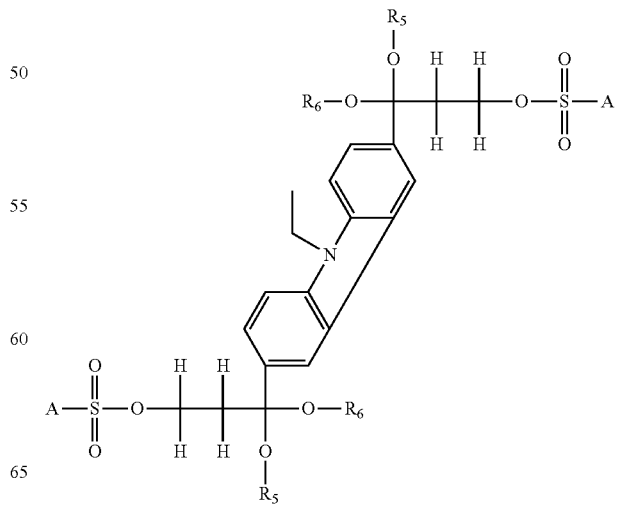

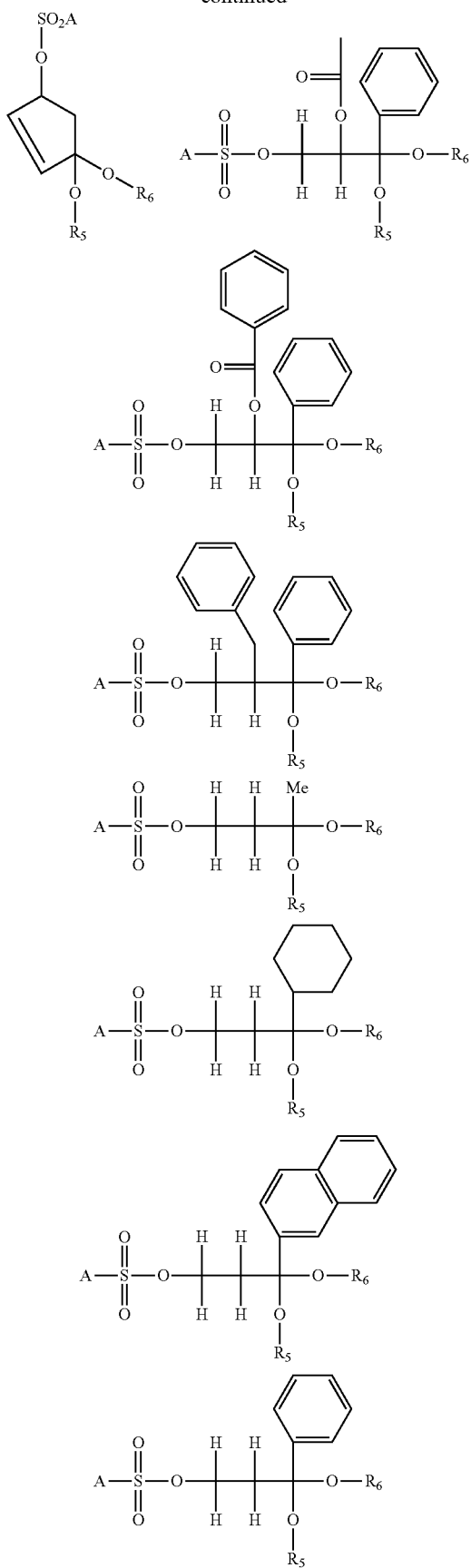

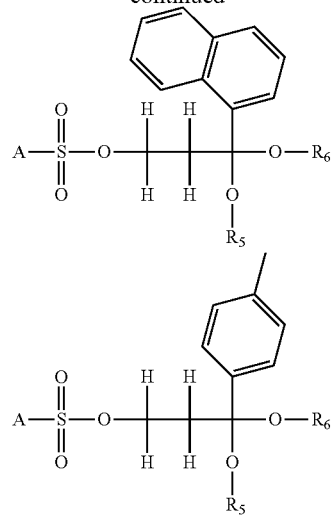

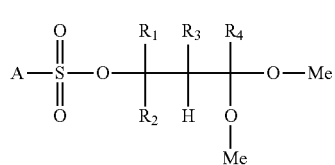

Now, $R_5$ and $R_6$ will be described.

In formula (1), each of $R_5$ and $R_6$ represents a monovalent substituent. As the monovalent substituent, there can be mentioned, for example, a monovalent organic group or a silyl group. As the monovalent organic group, there can be mentioned, for example, an alkyl group, a cycloalkyl group, an alkenyl group, an alkynyl group, an aryl group, an alkanoyl group, an alkoxycarbonyl group, an aryloxycarbonyl group, an alkylsulfonyl group, an arylsulfonyl group, an alkylthiocarbonyl group, an arylthiocarbonyl group or a dialkylaminocarbonyl group. A substituent may further be introduced in each of these monovalent organic groups.

As the alkyl group, cycloalkyl group, alkenyl group, alkynyl group, aryl group, alkanoyl group, alkoxycarbonyl group, aryloxycarbonyl group, alkylsulfonyl group, arylsulfonyl group, alkylthiocarbonyl group and arylthiocarbonyl group, there can be mentioned, for example, those set forth above in connection with $R_1$ to $R_4$.

As the optionally substituted dialkylaminocarbonyl group, there can be mentioned, for example, a dimethylaminocarbonyl group, a diethylaminocarbonyl group, a dipropylaminocarbonyl group or a dibutylaminocarbonyl group.

It is preferred for $R_5$ and $R_6$ to be bonded to each other to thereby form a cycloacetal structure. An aliphatic or aromatic hydrocarbon ring or a heterocycle containing a heteroatom may be introduced as a substituent in this cycloacetal structure. The above hydrocarbon ring and/or heterocycle may form a condensed ring in cooperation with the cycloacetal. As the hydrocarbon ring and heterocycle, there can be mentioned, for example, those set forth above in connection with $R_1$ to $R_4$.

The characters $R_5$ and $R_6$ used in general formula (1) mean, for example, those groups appearing in the following chemical formulae.

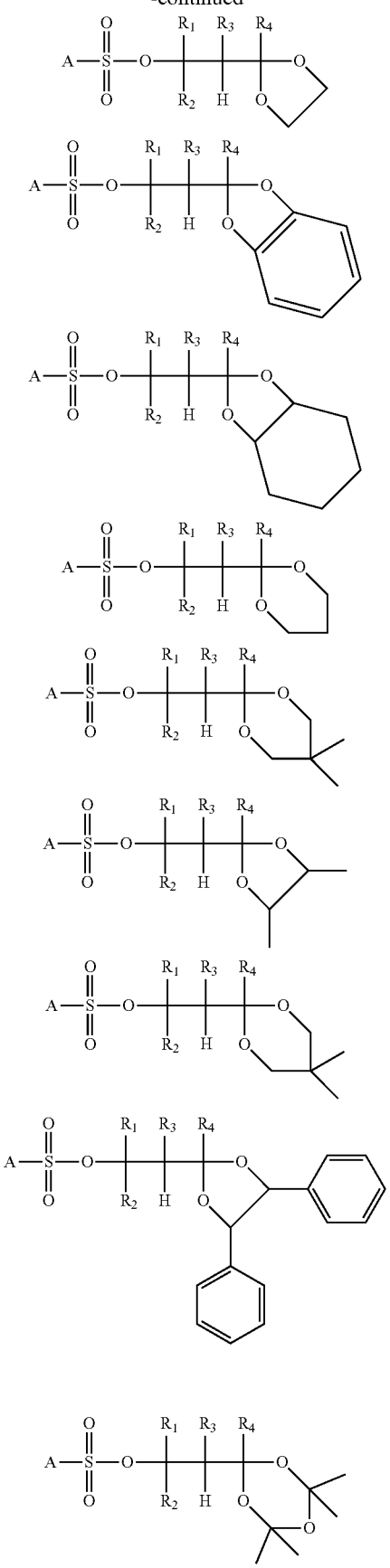
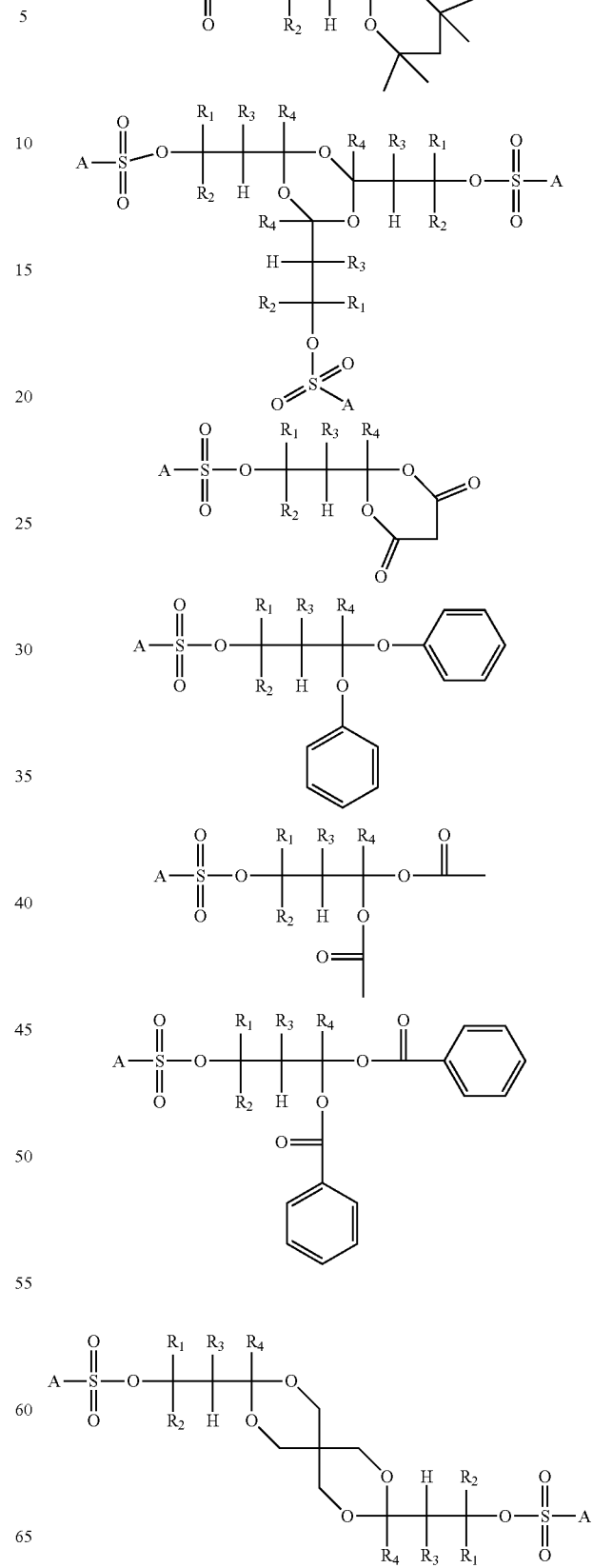

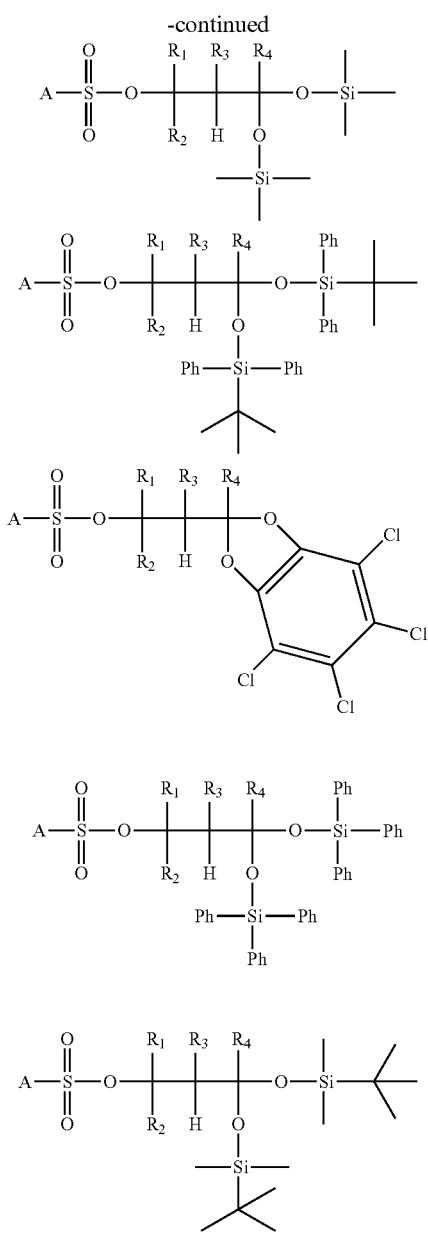
The characters $R_1$ to $R_6$ used in general formula (1) mean, for example, those groups appearing in the following chemical formulae.
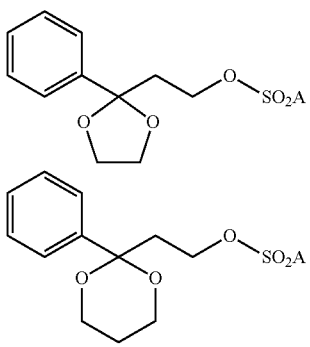
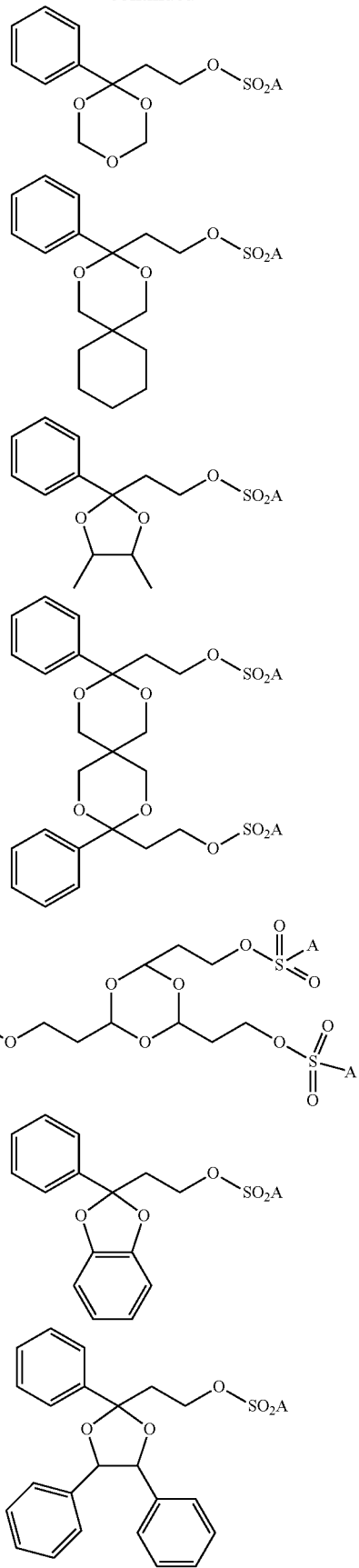

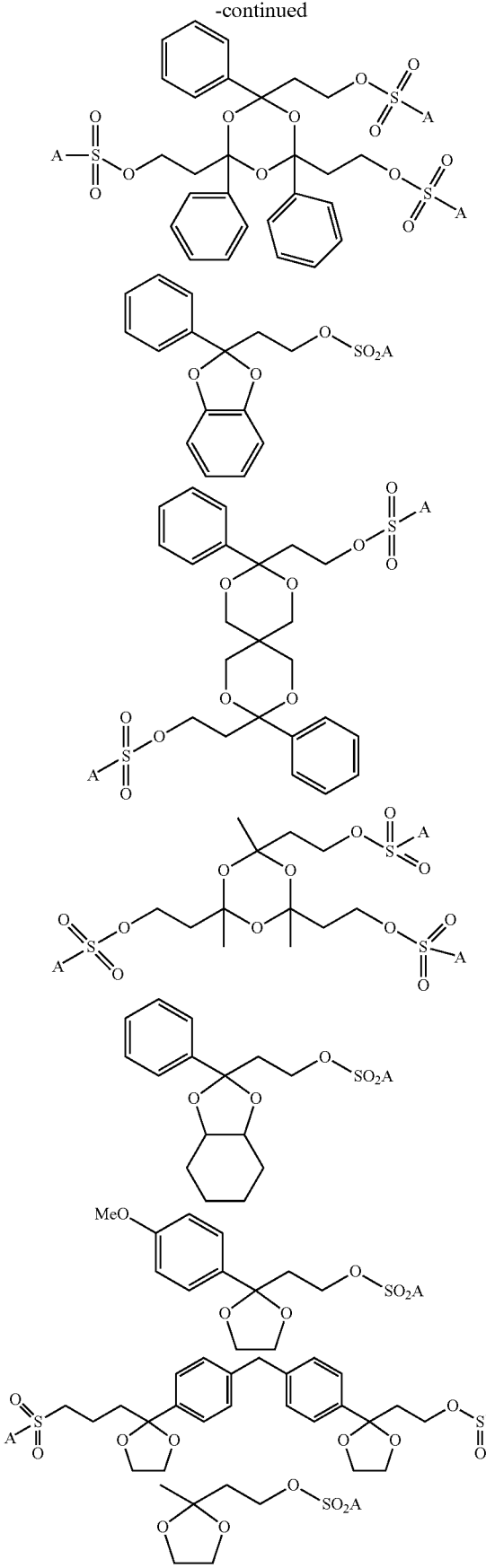

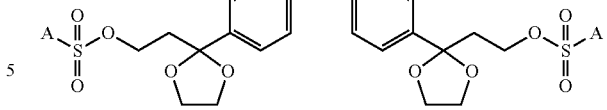

The compounds of general formulae (2) to (5) will be described in detail below.

First, $R_7$ to $R_9$ used in formula (2) will be described.

Each of $R_7$ to $R_9$ represents a hydrogen atom or a monovalent substituent. As the monovalent substituent, there can be mentioned, for example, an alkyl group, a cycloalkyl group, an aryl group or an aralkyl group.

The alkyl group is preferably an alkyl group having 1 to 8 carbon atoms. As such, there can be mentioned, for example, a methyl group, an ethyl group, a propyl group, an isopropyl group, a butyl group or an octyl group.

The cycloalkyl group is preferably one having 4 to 10 carbon atoms. As such, there can be mentioned, for example, a cyclopropyl group, a cyclopentyl group, a cyclohexyl group, a cycloheptyl group, an adamantly group, a bornyl group, an isobornyl group, a tricyclodecanyl group, a dicyclopentenyl group, a norbornaneepoxy group, a menthyl group, an isomenthyl group, a neomenthyl group and a tetracyclododecanyl group.

The aryl group is preferably one having 6 to 14 carbon atoms. As such, there can be mentioned, for example, a phenyl group, a naphthyl group or a tolyl group.

As the aralkyl group, there can be mentioned an aralkyl group having 7 to 20 carbon atoms, for example, a benzyl group, a phenethyl group, a naphthylethyl group or the like.

Substituents may be introduced in these alkyl group, cycloalkyl group, aryl group and aralkyl group. As such substituents, there can be mentioned, for example, a halogen atom such as Cl, Br or F, a —CN group, an —OH group, an alkyl group having 1 to 4 carbon atoms, a cycloalkyl group having 3 to 8 carbon atoms, an alkoxy group having 1 to 4 carbon atoms, an acylamino group such as an acetylamino group, an aralkyl group such as a benzyl group or a phenethyl group, an aryloxyalkyl group such as a phenoxyethyl group, an alkoxycarbonyl group having 2 to 5 carbon atoms and an acyloxy group having 2 to 5 carbon atoms.

$R_7$ is preferably, for example, a hydrogen atom, a methyl group, an ethyl group, a propyl group, a butyl group, a pentyl group, a cyclopropyl group, a cyclopentyl group, a cyclohexyl group, a phenyl group, a naphthyl group, a benzyl group or a phenethyl group.

$R_8$ is preferably, for example, a methyl group, an ethyl group, an isopropyl group, a t-butyl group, a neopentyl group, a cyclohexyl group, a phenyl group, a benzyl group or a hydrogen atom.

$R_9$ is preferably, for example, a hydrogen atom, a methyl group, an ethyl group, a propyl group, a butyl group, a pentyl group, a cyclopropyl group, a cyclopentyl group, a cyclohexyl group, a phenyl group, a naphthyl group, a benzyl group or a phenethyl group.

It is preferred for $R_7$ and $R_9$ to be bonded to each other to thereby form a cyclic structure. The ring structure is most preferably a cyclopentyl ring or a cyclohexyl ring.

Below, $R_{10}$ and $R_{11}$ appearing in formula (3) will be described.

Each of $R_{10}$ and $R_{11}$ represents a hydrogen atom or a monovalent substituent.

$R_{10}$ is, for example, an alkyl group, a cycloalkyl group, an aryl group, an aralkyl group, an alkoxy group, an aryloxy group, an alkenyloxy group or a hydrogen atom.

$R_{11}$ is, for example, an alkyl group, a cycloalkyl group, an aryl group, an aralkyl group, an alkoxy group, an aryloxy group, an alkenyl group or a hydrogen atom.

As the alkyl group, cycloalkyl group, aryl group and aralkyl group, there can be mentioned, for example, those set forth above in connection with general formula (2).

The alkoxy group is preferably one having 1 to 8 carbon atoms. As such, there can be mentioned, for example, a methoxy group, an ethoxy group, a propoxy group, a cyclohexyloxy group or a butoxy group.

The aryloxy group is preferably one having 6 to 14 carbon atoms. As such, there can be mentioned, for example, a phenoxy group or a naphthoxy group.

The alkenyl group is preferably one having 2 to 6 carbon atoms. For example, there can be mentioned a vinyl group, a propenyl group, an allyl group, a butenyl group, a pentenyl group, a hexenyl group or a cyclohexenyl group.

The alkenyloxy group is preferably one having 2 to 8 carbon atoms. For example, there can be mentioned a vinyloxy group or an allyloxy group.

Substituents may be introduced in these alkyl group, cycloalkyl group, aryl group, aralkyl group, alkoxy group, aryloxy group, alkenyl group and alkenyloxy group. As such substituents, there can be mentioned, for example, those set forth above in connection with general formula (2).

$R_{10}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, a naphthoxy group, a vinyloxy group or a methylvinyloxy group.

$R_{11}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, a naphthoxy group, a vinyl group or an allyl group.

It is preferred for $R_{10}$ and $R_{11}$ to be bonded to each other to thereby form a ring structure. The ring structure is most preferably a 3-oxocyclohexenyl ring or a 3-oxoindenyl ring. This 3-oxocyclohexenyl ring or 3-oxoindenyl ring may contain an oxygen atom in the ring thereof.

Further, $R_{12}$ to $R_{14}$ appearing in formula (4) will be described.

Each of $R_{12}$ and $R_{13}$ represents a hydrogen atom or a monovalent substituent. $R_{14}$ represents a monovalent substituent.

$R_{12}$ is, for example, an alkyl group, a cycloalkyl group, an aryl group, an aralkyl group, an alkoxy group, an aryloxy group or a hydrogen atom.

$R_{13}$ is, for example, an alkyl group, an alkoxy group, a halogen atom, an aralkyl group or a hydrogen atom.

$R_{14}$ is, for example, a group that when acted on by an acid, is eliminated.

As the group that is eliminated under the action of an acid, there can be mentioned, for example, any of the groups of the formulae —C(R36)(R37)(R38), —C(=O)—O—C(R36)(R37)(R38), —C(R01)(R02)(OR39), —C(R01)(R02)-C(=O)—O—C(R36)(R37)(R38) and —CH(R36)(Ar).

In the formulae, each of R36 to R39 independently represents an alkyl group, a cycloalkyl group, an aryl group, an aralkyl group or an alkenyl group. R36 and R37 may be bonded to each other to thereby form a ring.

Each of R01 and R02 independently represents a hydrogen atom, an alkyl group, a cycloalkyl group, an aryl group, an aralkyl group or an alkenyl group.

Ar represents an aryl group.

As the alkyl group, cycloalkyl group, aryl group, aralkyl group, alkoxy group and aryloxy group, there can be mentioned, for example, those set forth above in connection with general formulae (2) and (3). Substituents may be introduced in these groups. As such substituents, there can be mentioned, for example, those set forth above in connection with general formula (2).

As the halogen atom, there can be mentioned, for example, a fluorine atom, a chlorine atom, a bromine atom or an iodine atom.

$R_{12}$ is preferably, for example, a methyl group, an ethyl group, a propyl group, a cyclopropyl group, a cyclopentyl group, a cyclohexyl group, a phenyl group, a naphthyl group, a benzyl group, a phenethyl group, a naphthylmethyl group or a hydrogen atom.

$R_{13}$ is preferably, for example, a methyl group, an ethyl group, a propyl group, a butyl group, a benzyl group or a hydrogen atom.

$R_{14}$ is preferably, for example, a tertiary alkyl group such as a t-butyl group, an alkoxyalkyl group such as a methoxymethyl group, an ethoxymethyl group or a 1-ethoxyethyl group, or a tetrahydropyranyl group.

Now, $R_{15}$ to $R_{19}$ appearing in formula (5) will be described.

Each of $R_{15}$ to $R_{19}$ represents a hydrogen atom or a monovalent substituent.

$R_{15}$ is, for example, an alkyl group, a cycloalkyl group, an aryl group, an aralkyl group, an alkoxy group, an aryloxy group, an alkenyloxy group or a hydrogen atom.

$R_{16}$ is, for example, an alkyl group, a cycloalkyl group, an aryl group, an aralkyl group, an alkoxy group, an aryloxy group, an alkenyl group or a hydrogen atom.

$R_{17}$ is, for example, an alkyl group, a cycloalkyl group, an aryl group, an aralkyl group, an alkoxy group, an aryloxy group, an alkenyl group or a hydrogen atom.

$R_{18}$ is, for example, an alkyl group, a cycloalkyl group, an aryl group, an aralkyl group, an alkoxy group, an aryloxy group, an alkenyl group or a hydrogen atom.

$R_{19}$ is, for example, an alkyl group, a cycloalkyl group, an aryl group, an aralkyl group, an alkoxy group, an aryloxy group, an alkenyl group or a hydrogen atom.

As the alkyl group, cycloalkyl group, aryl group, aralkyl group, alkoxy group, aryloxy group, alkenyl group and alkenyloxy group, there can be mentioned, for example, those set forth above in connection with general formulae (2) and (3).

Substituents may be introduced in these alkyl group, cycloalkyl group, aryl group, aralkyl group, alkoxy group, aryloxy group, alkenyl group and alkenyloxy group. As such substituents, there can be mentioned, for example, those set forth above in connection with general formula (2).

$R_{15}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, naphthoxy group, a vinyloxy group or a methylvinyloxy group.

$R_{16}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, a naphthoxy group, a vinyl group or an allyl group.

$R_{17}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, a naphthoxy group, a vinyl group or an allyl group.

$R_{18}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, a naphthoxy group, a vinyl group or an allyl group.

$R_{19}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, a naphthoxy group, a vinyl group or an allyl group.

At least, two of $R_{15}$ to $R_{19}$ may be bonded to each other to thereby form a ring structure.

The characters $R_7$ to $R_{19}$ used in general formulae (2) to (5) mean, for example, those groups appearing in the following chemical formulae.

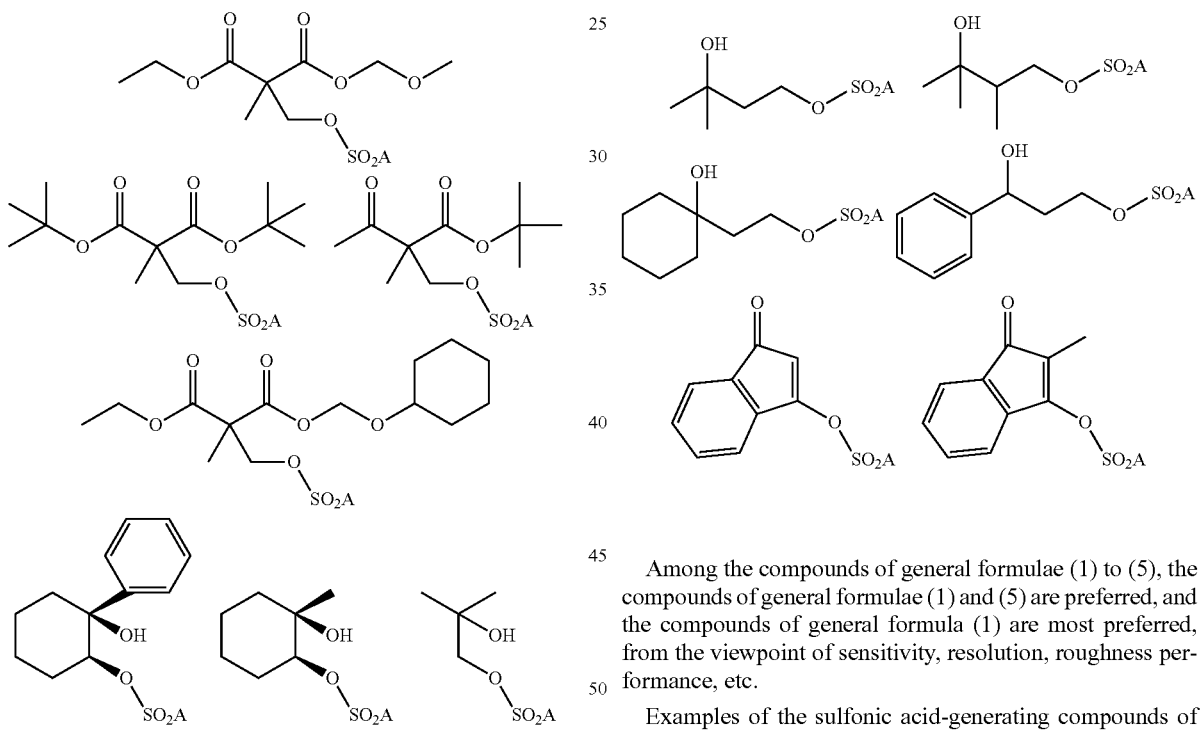

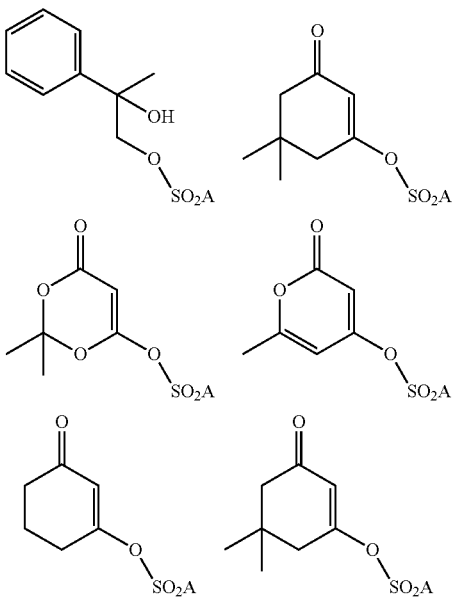

Among the compounds of general formulae (1) to (5), the compounds of general formulae (1) and (5) are preferred, and the compounds of general formula (1) are most preferred, from the viewpoint of sensitivity, resolution, roughness performance, etc.

Examples of the sulfonic acid-generating compounds of general formulae (1) to (5) are as follows.

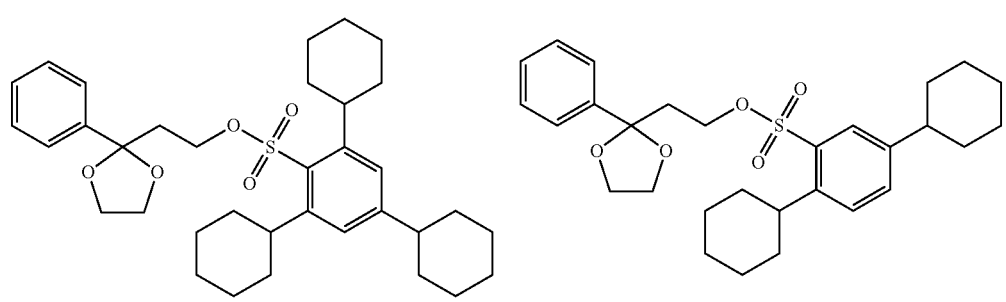

-continued
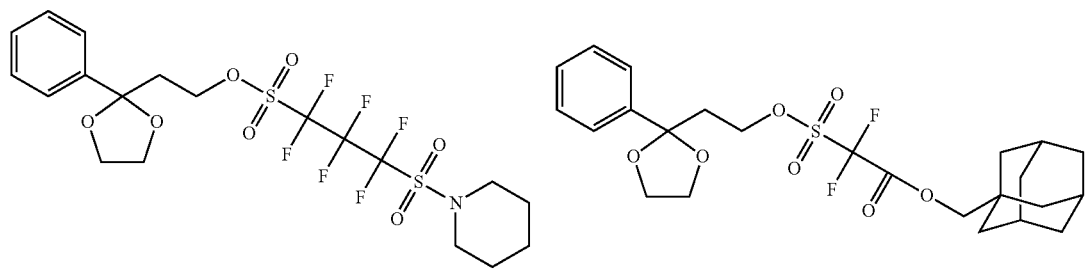
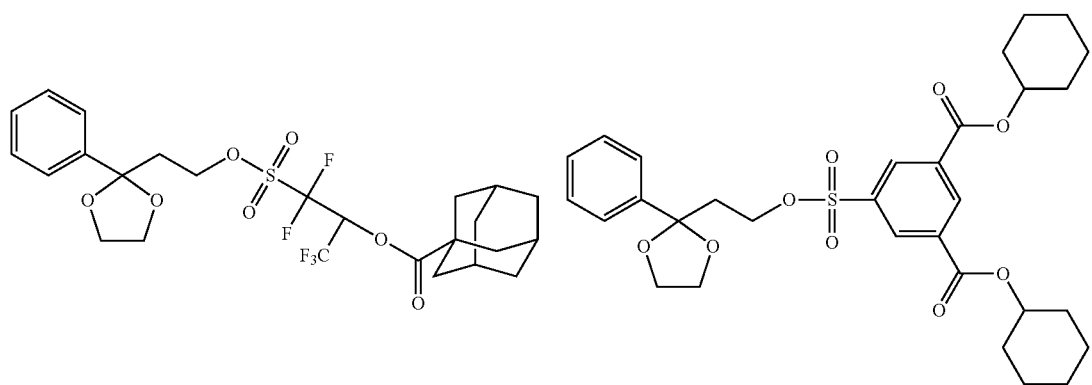
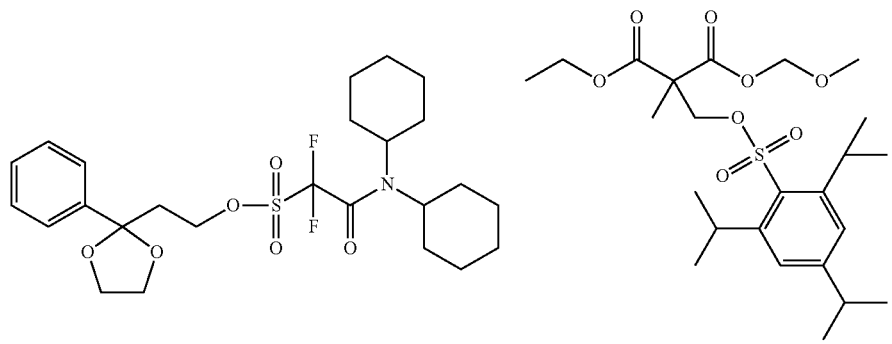
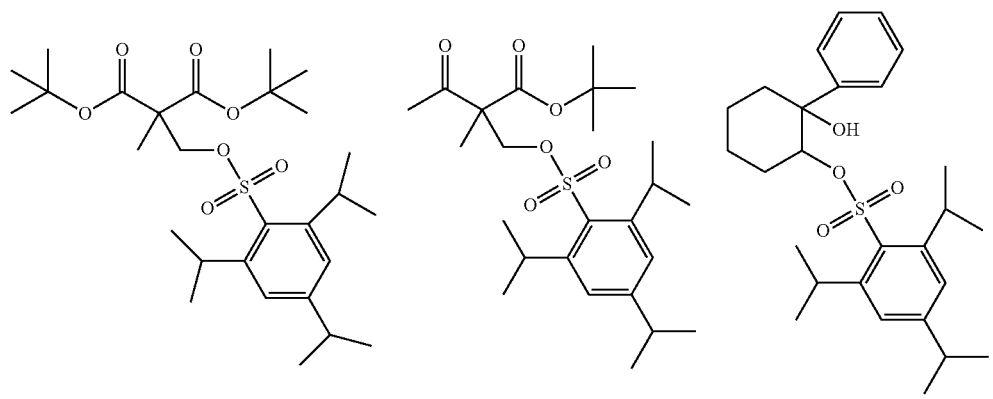

-continued
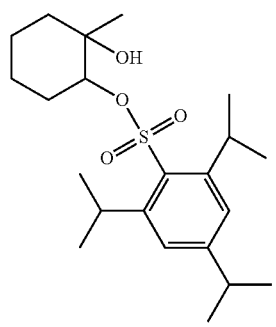
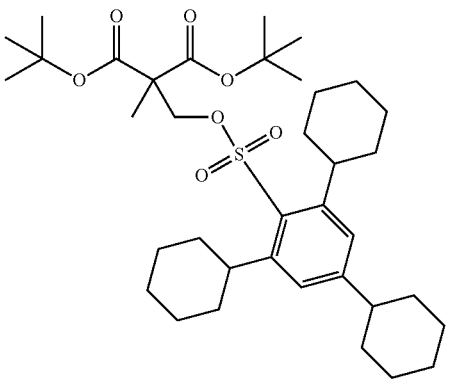
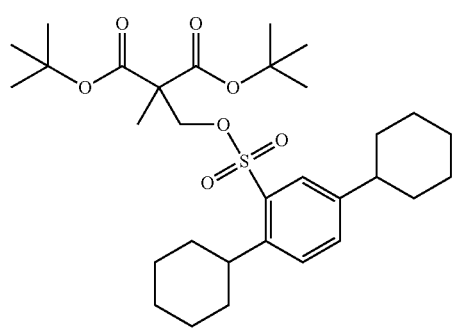
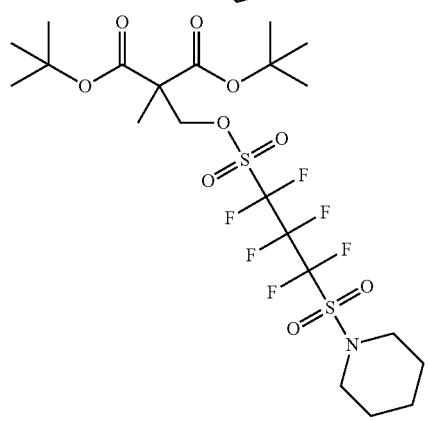
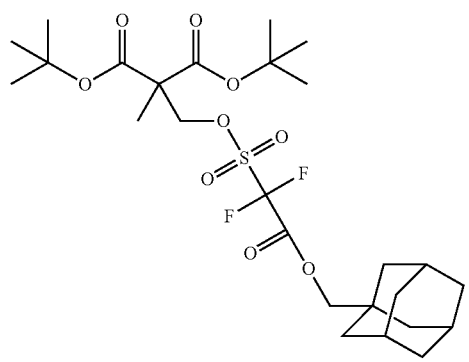
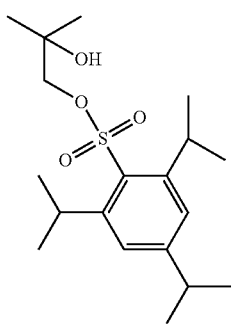
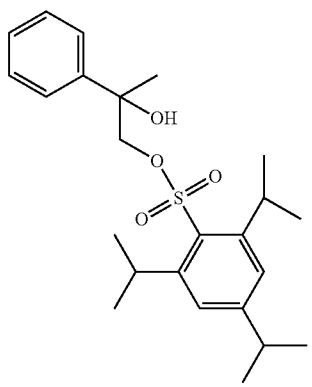
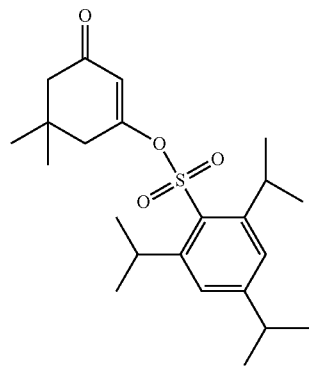
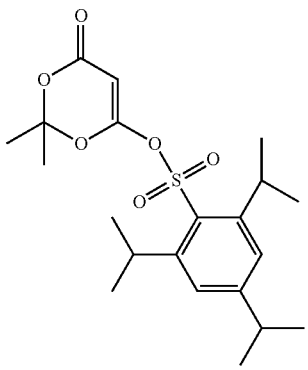
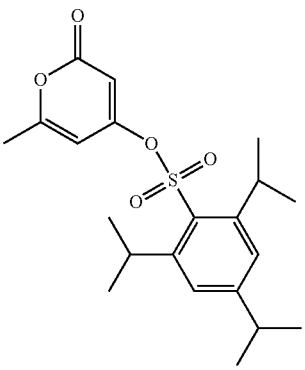

-continued
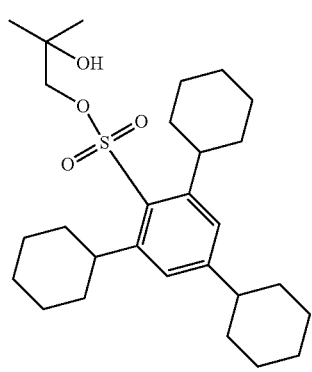 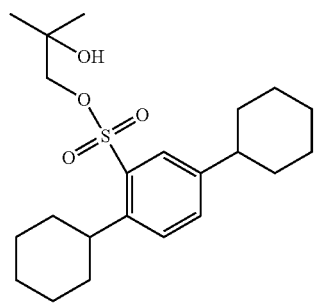 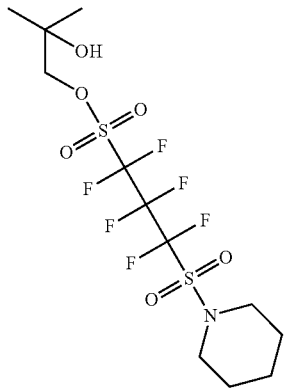
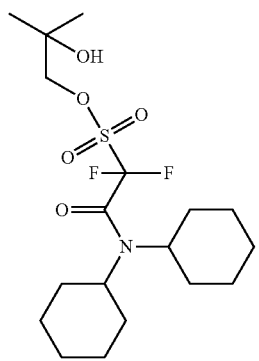 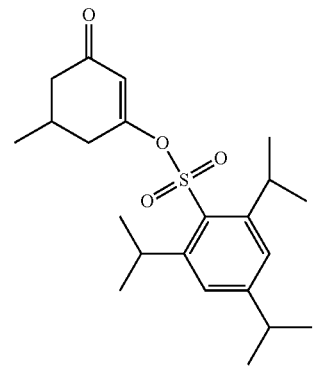 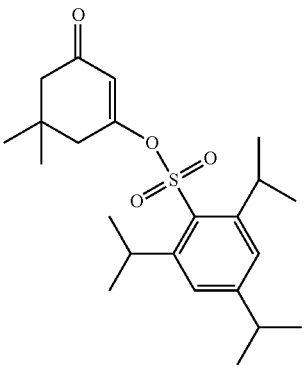
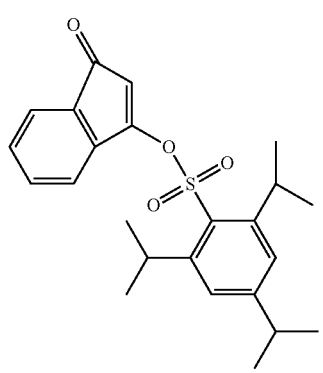 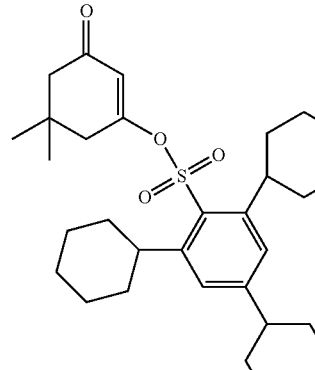 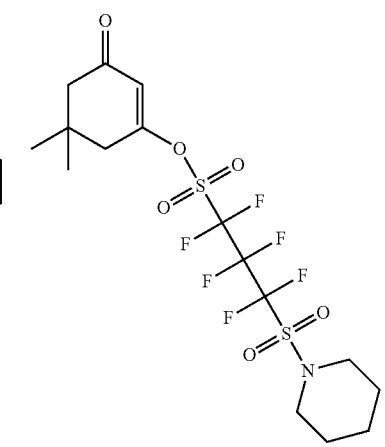
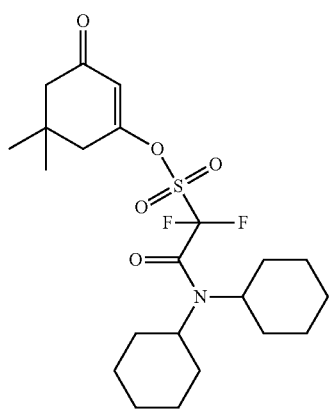 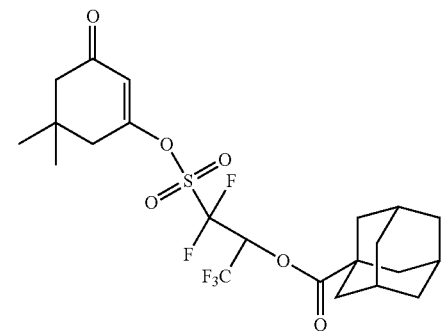 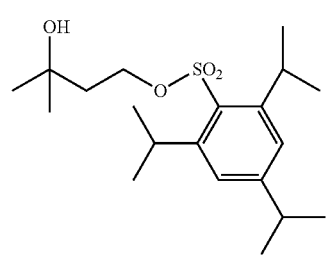

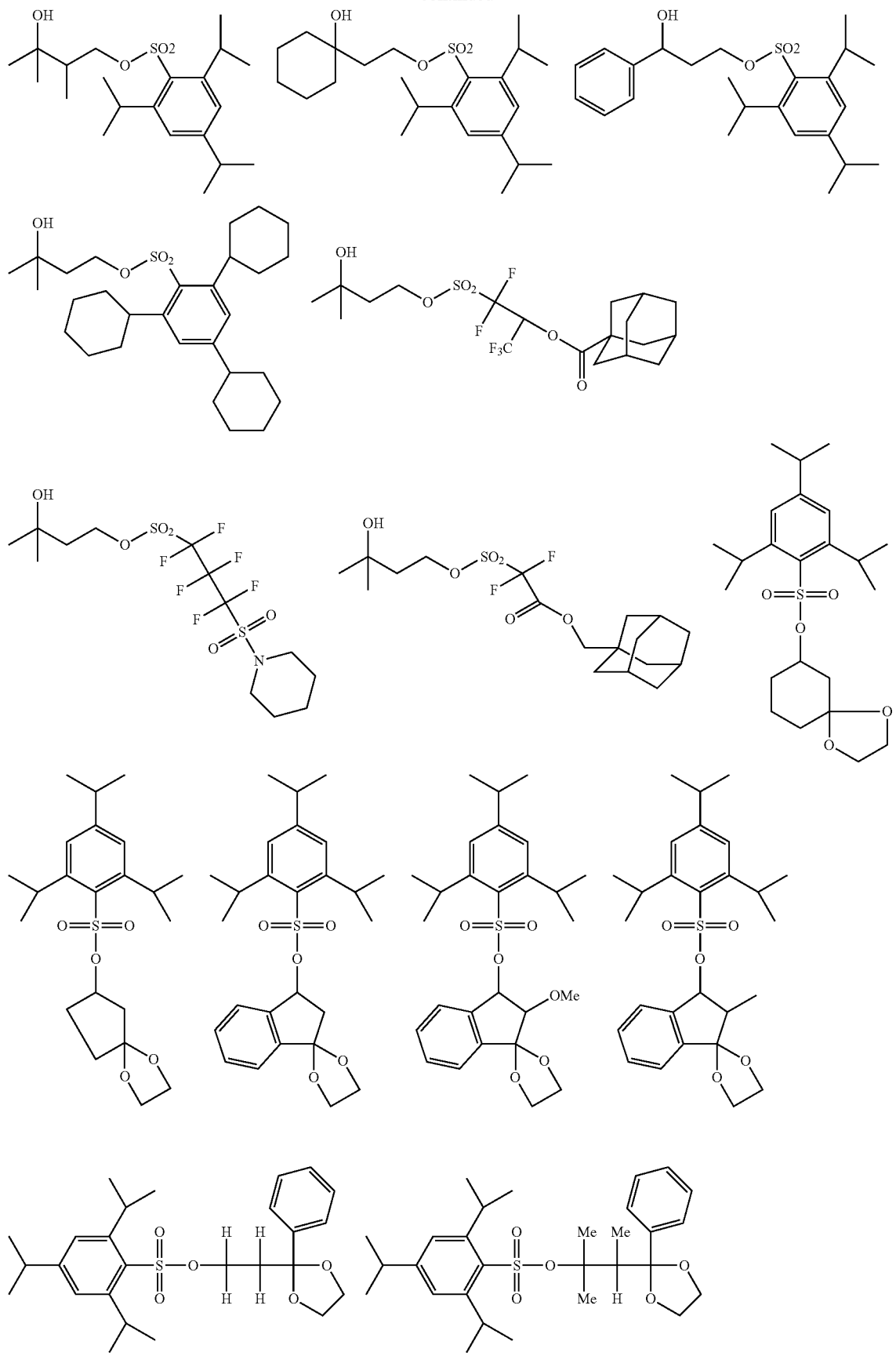

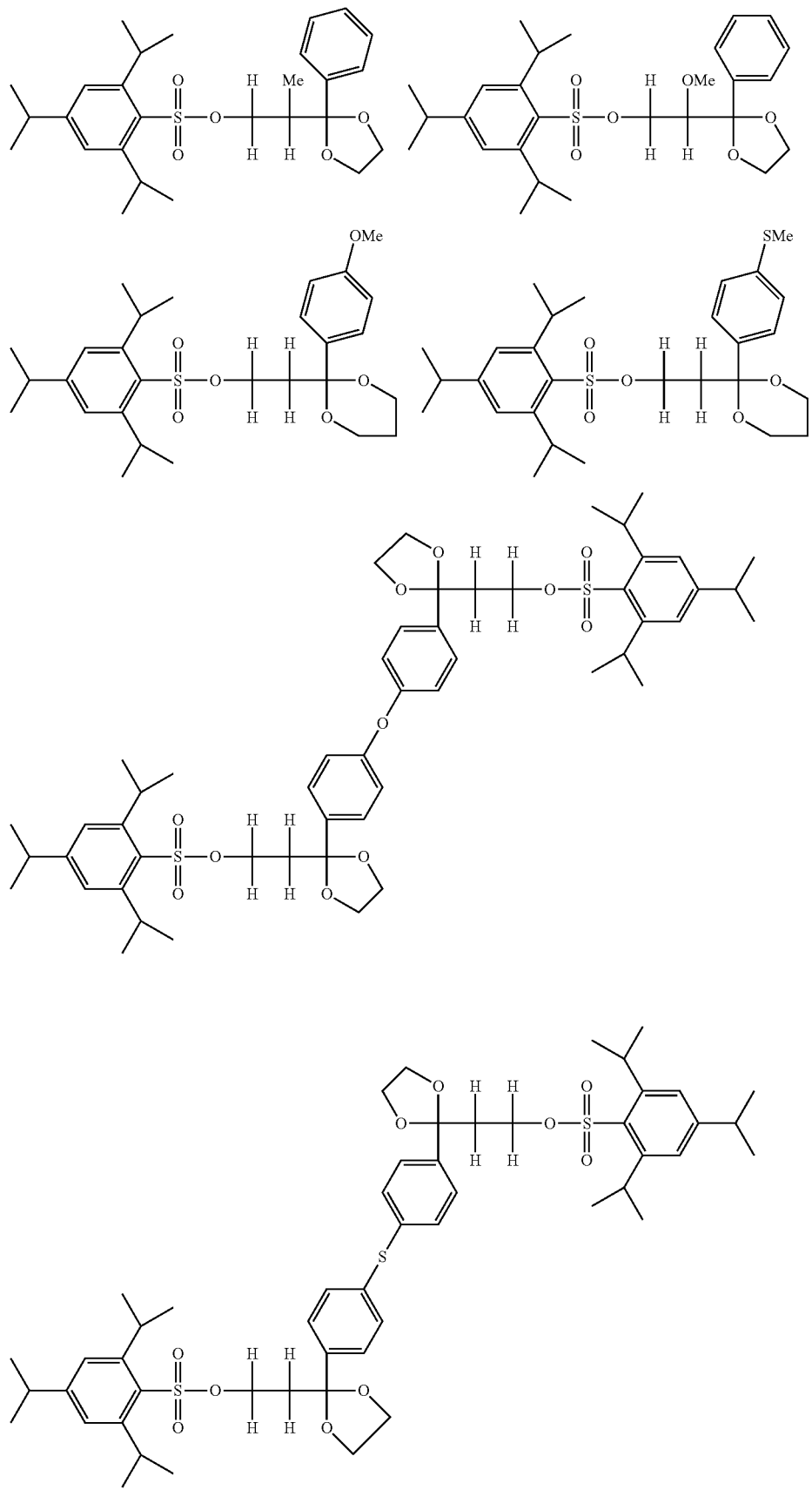

-continued
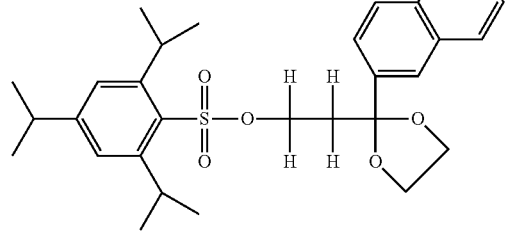 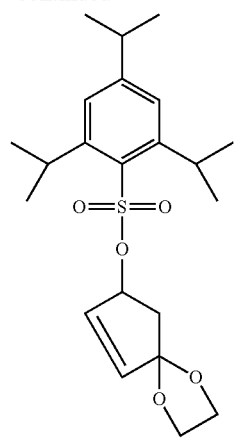
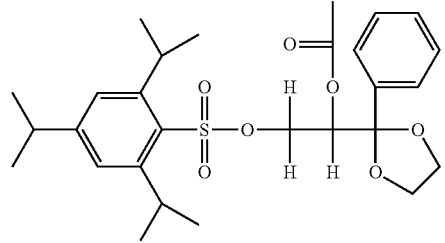 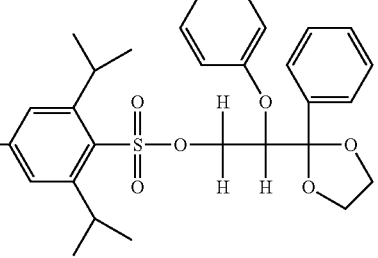
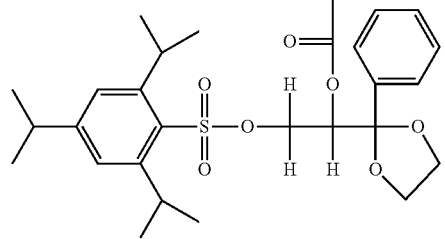 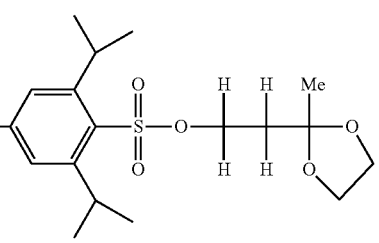
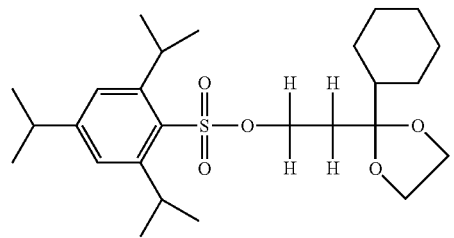 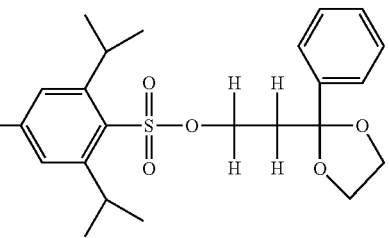
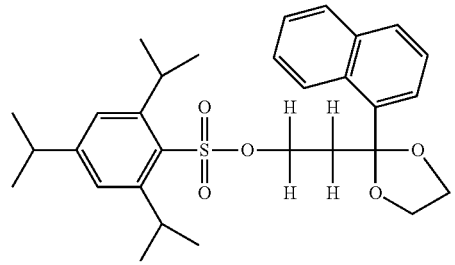 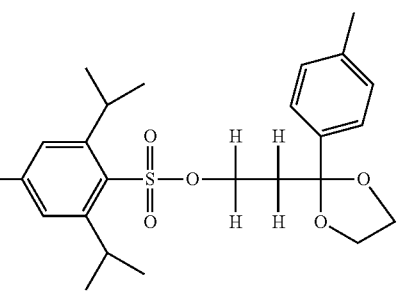

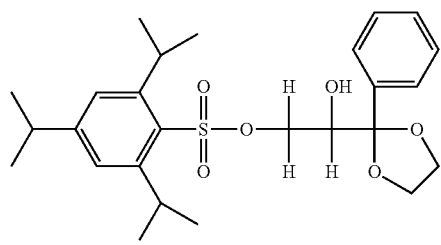

The content of sulfonic acid-generating compound based on the total solids of the composition is preferably in the range of 0.1 to 50 mass %, more preferably 0.5 to 40 mass % and further more preferably 1.0 to 30 mass %.

With respect to the process for producing the sulfonic acid-generating compound according to the present invention, the compound can be easily synthesized by reacting a corresponding alcohol compound with a sulfonyl halide or sulfonic anhydride in the presence of a base (for example, triethylamine or pyridine) in an inert solvent, such as THF, DMF or acetonitrile, or a basic solvent, such as pyridine. The temperature at which the reaction is performed is preferably in the range of −10 to 60° C.

By using an alkylsulfonyl halide, an arylsulfonyl halide or the like as the sulfonyl halide, various corresponding sulfonic acid-generating compounds can be synthesized.

[2] Photoacid Generator

As such a photoacid generator, use can be made of, for example, a member appropriately selected from among a photoinitiator for photocationic polymerization, a photoinitiator for photoradical polymerization, a photo-achromatic agent and photo-discoloring agent for dyes, any of heretofore known compounds that when exposed to actinic rays or radiation, generate an acid, employed in microresists, etc., and mixtures thereof. As examples of the photoacid generators, there can be mentioned a sulfonium salt or an iodonium salt, and bis(alkylsulfonyldiazomethane) etc.

As preferred compounds among the acid generators, those represented by the following general formulae (ZI), (ZII) and (ZIII) can be exemplified.

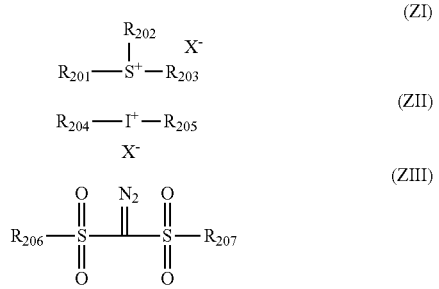

In the above general formula (ZI), each of $R_{201}$, $R_{202}$ and $R_{203}$ independently represents an organic group.

The number of carbon atoms in the organic group represented by $R_{201}$, $R_{202}$ and $R_{203}$ is generally in the range of 1 to 30, preferably 1 to 20.

Two of $R_{201}$ to $R_{203}$ may be bonded to each other through single bond or connecting group to form a ring. As the connecting group, for example, an ether bond, a thioether bond, an ester bond, an amido bond, a carbonyl group, a methylene group, and an ethylene group can be exemplified. As the group formed by bonding of two of $R_{201}$ to $R_{203}$, for example, an alkylene group such as a butylene group or a pentylene group can be exemplified.

As the specific examples of $R_{201}$, $R_{202}$, and $R_{203}$, corresponding groups in the compounds (ZI-1), (ZI-2), or (ZI-3) described below can be exemplified.

$X^-$ represents a normucleophilic anion. As $X^-$, for example, a sulfonate anion, a bis(alkylsulfonyl)imido anion, a tris(alkylsulfonyl)methyl anion, $BF_4^-$, $PF_6^-$, and $SbF_6^-$ can be exemplified. $X^-$ preferably is an organic anion containing one or more carbon atoms. As the preferred organic anions, any of those represented by the following AN1 to AN3 can be exemplified.

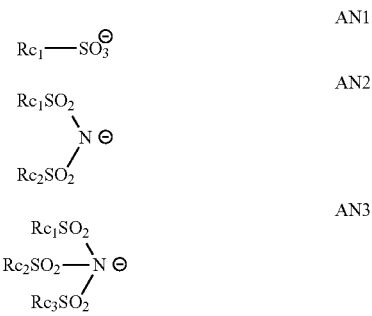

In the formulae AN1 to AN3, $Rc_1$ to $Rc_3$ each independently represents an organic group. As the organic group, those having 1 to 30 carbon atoms can be exemplified. Preferably, an alkyl group, an aryl group, or a group in which these groups are connected through a connecting group. As the connecting group, for example, a single bond, —O—, —CO$_2$—, —S—, —SO$_3$— and —SO$_2$N(Rd$_1$)- can be exemplified. Here, $Rd_1$ represents a hydrogen atom or an alkyl group, and may form a ring together with a binding alkyl or aryl group.

An organic group represented by $Rc_1$ to $Rc_3$ may be an alkyl group whose 1-position is substituted with a fluorine atom or a fluoroalkyl group; or a phenyl group substituted with a fluorine atom or a fluoroalkyl group. Presence of a fluorine atom or a fluoroalkyl group can make an acidity of the acid generated by irradiating light become higher. This can enhance the sensitivity of the composition. $Rc_1$ to $Rc_3$ may bond to other alkyl groups, aryl groups, and the like, to thereby form a ring.

As preferred $X^-$, the following general formulae can be exemplified. These $X^-$ are conjugate base of the sulfonic acid represented by general formulae (6) or (7) above.

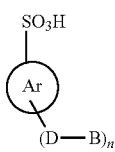 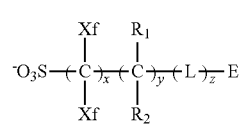

In the above formulae, each of Ar, D, B, Xf, $R_1$, $R_2$, E, x, y and z is as defined in the formulae (6) and (7) above.

Appropriate use may be made of compounds with two or more of the structures represented by the general formula (ZI). For example, use may be made of compounds having a structure wherein at least one of $R_{201}$ to $R_{203}$ of a compound represented by the general formula (ZI) is bonded to at least one of $R_{201}$ to $R_{203}$ of another compound represented by the general formula (ZI).

As preferred (ZI) components, the following compounds (ZI-1) to (ZI-4) can be exemplified.

The compounds (ZI-1) are arylsulfonium compounds of the general formula (ZI) wherein at least one of $R_{201}$ to $R_{203}$ is an aryl group, namely, compounds containing an arylsulfonium as a cation.

In the arylsulfonium compounds, all of the $R_{201}$ to $R_{203}$ may be aryl groups. It is also appropriate that the $R_{201}$ to $R_{203}$ are partially an aryl group and the remainder is an alkyl group. When the compound (ZI-1) contains two or more aryl groups, these may either be identical to or different from each other.

As the compound (ZI-1), there can be mentioned, for example, a triarylsulfonium compound, a diarylalkylsulfonium compound, and an aryldialkylsulfonium compound.

As an aryl group in the compound (ZI-1), a phenyl group, a naphthyl group, or a heteroaryl group such as an indole group and a pyrrole group. Of these, a phenyl group, a naphthyl group, or an indole group particularly preferred.

As alkyl group contained in the compound (ZI-1) according to necessity, there can be mentioned, for example, a methyl group, an ethyl group, a propyl group, an n-butyl group, a sec-butyl group, a t-butyl group, a cyclopropyl group, a cyclobutyl group, a cyclohexyl group or the like.

The aryl group or alkyl group represented by $R_{201}$ to $R_{203}$ may have one or more substituents. As the substituent, an alkyl group (for example, 1 to 15 carbon atoms), an aryl group (for example, 6 to 14 carbon atoms), an alkoxy group (for example, 1 to 15 carbon atoms), a halogen atom, a hydroxy group, and a phenylthio group can be exemplified.

Preferred substituents are a linear or branched alkyl group having 1 to 12 carbon atoms, and branched or cyclic alkoxy group having 1 to 12 carbon atoms. More preferred substituents are an alkyl group having 1 to 6 carbon atoms and an alkoxy group having 1 to 6 carbon atoms. The substituents may be contained in any one of the three $R_{201}$ to $R_{203}$, or alternatively may be contained in all three of $R_{201}$ to $R_{203}$. When $R_{201}$ to $R_{203}$ represent a phenyl group, the substituent preferably lies at the p-position of the phenyl group.

Further, an embodiment that one or two or the $R_{201}$ to $R_{203}$ is an optionally-substituted aryl group and the remainder is an alkyl group is also preferred. As the specific example of the structure, those represented in [0141] to [0153] of JP-A-2004-210670.

In this case, the aryl group is the same as the one described above, and preferably is a phenyl group or a naphthyl group. The aryl group preferably contain one or more hydroxy groups, alkoxy groups, or alkyl groups as substituent. The substituent is more preferably an alkoxy group having 1 to 12 carbon atoms, and further preferably an alkyl group having 1 to 6 carbon atoms.

The alkyl group as the remainder is preferably the one having 1 to 6 carbon atoms. These groups may contain one or more substituents. Further, when two groups are present as the remainder, these may be bonded to each other to thereby form a ring.

Now, the compounds (ZI-2) will be described.

The compounds (ZI-2) are compounds of formula (ZI) wherein each of $R_{201}$ to $R_{203}$ independently represents an organic group having no aromatic ring. The aromatic rings include an aromatic ring having a heteroatom.

The organic group having no aromatic ring represented by $R_{201}$ to $R_{203}$ generally has 1 to 30 carbon atoms, preferably 1 to 20 carbon atoms.

Preferably, each of $R_{201}$ to $R_{203}$ independently represents an alkyl group, a 2-oxoalkyl group and an alkoxycarbonylmethyl group. Especially preferred is a linear or branched 2-oxoalkyl group.

As preferred alkyl groups represented by $R_{201}$ to $R_{203}$, there can be mentioned a linear or branched alkyl group having 1 to 10 carbon atoms (for example, a methyl group, an ethyl group, a propyl group, a butyl group or a pentyl group) and a cycloalkyl group having 3 to 10 carbon atoms (a cyclopentyl group, a cyclohexyl group or a norbornyl group).

The 2-oxoalkyl group may be linear, branched or cyclic. A group having >C=O at the 2-position of the alkyl group is preferred.

As preferred alkoxy moieties in the alkoxycarbonylmethyl group, there can be mentioned alkoxy groups having 1 to 5 carbon atoms (a methoxy group, an ethoxy group, a propoxy group, a butoxy group and a pentoxy group).

The $R_{201}$ to $R_{203}$ may be further substituted with a halogen atom, an alkoxy group (for example, 1 to 5 carbon atoms), a hydroxyl group, a cyano group and/or a nitro group.

Two of $R_{201}$ to $R_{203}$ may be bonded to each other to thereby form a ring structure, and the ring within the same may contain an oxygen atom, a sulfur atom, an ester bond, an amido bond or a carbonyl group. As the group formed by the ring formation, an alkylene group such as a butylene group and a pentylene group can be exemplified.

The explanation on the compounds (ZI-3) follows.

The compounds (ZI-3) are those represented by the following general formula (ZI-3) which have a phenacylsulfonium salt structure.

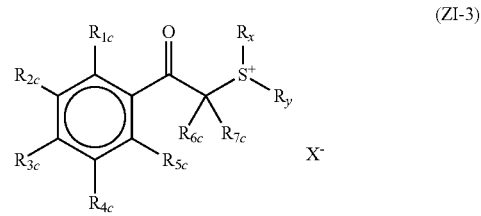

(ZI-3)

In the formula, each of $R_{1c}$ to $R_{5c}$ independently represents a hydrogen atom, an alkyl group, an alkoxy group, or a halogen atom. The alkyl group and the alkoxy group preferably have 1 to 6 carbon atoms.

Each of $R_{6c}$ and $R_{7c}$ independently represents a hydrogen atom or an alkyl group. The alkyl group preferably has 1 to 6 carbon atoms.

Each of $R_x$ and $R_y$ independently represents an alkyl group, a 2-oxoalkyl group, an alkoxycarbonylalkyl group, an allyl group, or a vinyl group. These groups preferably have 1 to 6 carbon atoms.

Any two or more of $R_{1c}$ to $R_{5c}$, and $R_{6c}$ and $R_{7c}$, and $R_x$ and $R_y$ may be bonded with each other to thereby form a ring structure. This ring structure may contain an oxygen atom, a sulfur atom, an ester bond, and/or an amido bond.

$X^-$ in compounds (ZI-3) represents the same as mentioned with respect to the $X^-$ in the general formula (ZI).

As the specific examples of the compounds (ZI-3), those described in [0047] and [0048] of JP-A-2004-233661 and in [0040]-[0046] of JP-A-2003-35948 can be exemplified.

Now the compounds (ZI-4) will be described.

The compounds (ZI-4) are those having a cation structure represented by the general formula (ZI-4) below. The compounds (ZI-4) are effective for suppressing outgas.

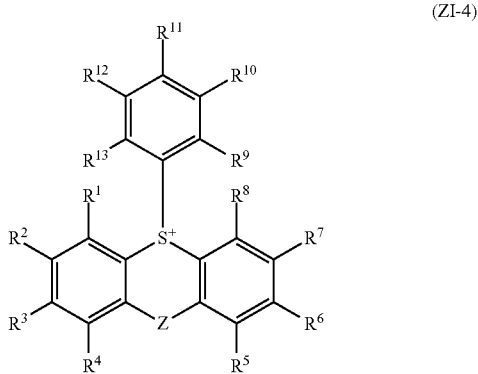

(ZI-4)

In the formula (ZI-4), $R^1$ to $R^{13}$ each independently represents a hydrogen atom or a substituent. Preferably, at least one of $R^1$ to $R^{13}$ is a substituent containing one or more alcoholic hydroxy groups. Here, the term "alcoholic hydroxy group" means a hydroxy group bonded to a carbon atom in an alkyl group.

Z is a single bond or a bivalent connecting group.

When $R^1$ to $R^{13}$ is a substituent containing one or more alcoholic hydroxy groups, $R^1$ to $R^{13}$ preferably is a group represented by —(W—Y). Here, Y represents an alkyl group substituted with one or more hydroxy group, and W represents a single bond or a bivalent connecting group.

As preferred alkyl groups represented by Y, an ethyl group, a propyl group, and an isopropyl group can be exemplified. Y preferably contains a structure represented by —CH$_2$CH$_2$OH.

As preferred bivalent connecting group represented by W, there can be mentioned a single bond and a bivalent group formed by substituting an arbitary hydrogen atom with a single bond in an alkoxy group, an acyloxy group, an acylamino group, an alkyl and aryl sulfonylamino group, an alkylthio group, an alkylsulfonyl group, an acyl group, an alkoxycarbonyl group, or a carbamoyl group. More preferably, W represents a single bond, or a bivalent group formed by substituting an arbitary hydrogen atom with a single bond in an acyloxy group, a alkylsulfonyl group, an acyl group, or an alkoxycarbonyl group.

When $R^1$ to $R^{13}$ is a substituent containing one or more alcoholic hydroxy groups, they each preferably contains 2 to 10 carbon atoms, more preferably contains 2 to 6 carbon atoms, and further preferably 2 to 4 carbon atoms.

Each of $R^1$ to $R^{13}$ may contains two or more alcoholic hydroxy group. The number of alcoholic hydroxy groups in each of $R^1$ to $R^{13}$ preferably 1 to 6, more preferably 1 to 3, and most preferably 1.

The total number of alcoholic hydroxy groups of $R^1$ to $R^{13}$ in a compound (ZI-4) is 1 to 10, preferably 1 to 6, and more preferably 1 to 3.

In a case each of $R^1$ to $R^{13}$ does not contain alcoholic hydroxy groups, the substituent represented by them is, for example, a halogen atom, an alkyl group, a cycloalkyl group, an alkenyl group, a cycloalkenyl group, an alkynyl group, an aryl group, a heterocyclic group, a cyano group, a nitro group, a carboxy group, an alkoxy group, an aryloxy group, silyloxy group, a heterocyclic-oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl and aryl sulfonylamino group, a mercapto group, an alkylthio group, an arylthio group, a heterocyclic-thio group, a sulfamoyl group, a sulfo group, an alkyl and aryl sulfynyl group, an alkyl and aryl sulfonyl group, an acyl group, an aryloxycarbonyl group, an alkoxycarbonyl group, a carbamoyl group, an aryl and heterocyclic azo group, an imido group, a phosphino group, a phosphynyl group, a phosphynyloxy group, a phosphynylamino group, an phosphono group, a silyl group, a hydrazino group, a ureido group, a boronic acid group [—B(OH)$_2$], a phosphato group [—OPO(OH)$_2$], a sulfato group [—OSO$_3$H], or other known substituents.

In a case each of $R^1$ to $R^{13}$ does not contain alcoholic hydroxy groups, each of them preferably is a hydrogen atom, a halogen atom, an alkyl group, a cycloalkyl group, an alkenyl group, a cycloalkenyl group, an alkynyl group, an aryl group, a cyano group, a carboxy group, an alkoxy group, an aryloxy group, an acyloxy group, a carbamoyloxy group, an acylamino group, an aminocarbonylamino group, an alkoxycarbonylamino group, an aryloxycarbonylamino group, a sulfamoylamino group, an alkyl and aryl sulfonylamino group, an alkylthio group, an arylthio group, a sulfamoyl group, an alkyl and aryl sulfonyl group, an aryloxycarbonyl group, an alkoxycarbonyl group, a carbamoyl group, an imido group, a silyl group, or a ureido group.

In a case each of $R^1$ to $R^{13}$ does not contain alcoholic hydroxy groups, each of them more preferably is a hydrogen atom, a halogen atom, an alkyl group, a cycloalkyl group, a cyano group, an alkoxy group, an acyloxy group, an acylamino group, an aminocarbonylamino group, an alkoxycarbonylamino group, an alkyl and aryl sulfonylamino group, an alkylthio group, a sulfamoyl group, an alkyl and aryl sulfonyl group, an alkoxycarbonyl group, or a carbamoyl group.

In a case each of $R^1$ to $R^{13}$ does not contain alcoholic hydroxy groups, each of them particularly preferably is a hydrogen atom, an alkyl group, a cycloalkyl group, a halogen atom, or an alkoxy group.

The neighboring two of $R^1$ to $R^{13}$ may bond to each other to form a ring. Examples of the ring include an aromatic and nonaromatic hydrocarbon rings, and an aromatic and nonaromatic heterocycles. There rings may be combined together to form a condensed ring.

The compounds (ZI-4) preferably have a structure in which at least one of $R^1$ to $R^{13}$ contains one or more alcoholic hydroxy group. More preferably, The compounds (ZI-4) preferably have a structure in which at least one of $R^9$ to $R^{13}$ contains one or more alcoholic hydroxy group.

As stated, Z represents a single bond or a bivalent connecting group. As the connecting group, for example, an alkylene group, an arylene group, a carbonyl group, a sulfonyl group, a carbonyloxy group, a carbonylamino group, a sulfonylamido group, an ether group, a thioether group, an amino group, a disulfide group, an acyl group, an alkylsulfonyl group, —CH=CH—, an aminocarbonylamino group and an aminosulfonylamino group.

The bivalent connecting group may contain one or more substituents. As such, those explained for $R^1$ to $R^{13}$ can be exemplified.

Z preferably is a single bond or a connecting group having no electron-withdrawing properties. As the connecting group, an alkylene group, an arylene group, an ether group, a thioether group, an amino group, —CH=CH—, an aminocarbonylamino group, and an aminosulfonylamino group can be exemplified. Z more preferably is a single bond, an ether group, or a thioether group. Of these, a single bond is especially preferred.

Explanations on general formula (ZII) and (ZIII) will follow.

In the general formulae (ZII) and (ZIII), each of $R_{204}$ to $R_{207}$ independently represents an aryl group, an alkyl group or a cycloalkyl group. These groups can contain one or more substituents.

As preferred aryl group represented by $R_{204}$ to $R_{207}$, those explained for $R_{201}$ to $R_{203}$ in the compounds (ZI-1) can be exemplified.

As preferred alkyl group and cycloalkyl group, those explained for $R_{201}$ to $R_{203}$ in the compounds (ZI-2) can be exemplified.

$X^-$ in the general formulae (ZII) and (ZIII) is the same as in the general formula (ZI).

As other examples of photoacid generator, compounds represented by the following general formula (ZIV), (ZV) or (ZVI) can be exemplified.

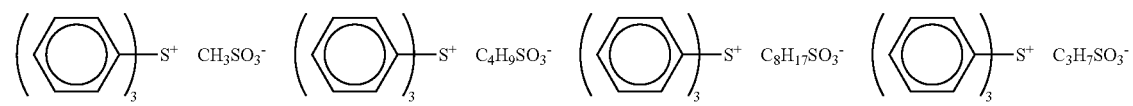

ZIV

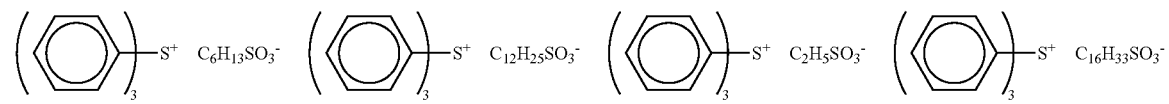

ZV

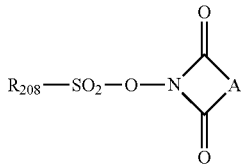

ZVI

In the general formulae (ZIV) to (ZVI), each of $Ar_3$ and $Ar_4$ independently represents an aryl group.

Each of $R_{208}$ independently represents an alkyl group, a cycloalkyl group or an aryl group. These groups may either be substituted or unsubstituted.

It is preferable for these groups to be substituted with one or more fluorine atoms. This leads to higher acidity of an acid generated by the photoacid generator.

Each of $R_{209}$ and $R_{210}$ independently represents an alkyl group, a cycloalkyl group, an aryl group, or an electron-withdrawing group. These groups may either be substituted or unsubstituted.

As preferred $R_{209}$, substituted or unsubstituted aryl groups can be exemplified.

As preferred $R_{210}$, electron-withdrawing groups can be exemplified. As such, a cyano group and a fluoroalkyl group is preferable.

A represents an alkylene group, an alkenylene group, or an arylene group. These groups may contain one or more substituents.

As a photoacid generator, compounds containing two or more structures represented by the general formula (ZVI) are also preferable. As such, compounds in which two or more structures represented by the general formula (ZVI) are combined to at the positions of $R_{209}$s or Rms.

As photoacid generators, compounds represented by the general formula (ZI) to (ZIII) is more preferable. Of these, compounds represented by the general formula (ZI) is especially preferred. Particularly, compounds (ZI-1) to (ZI-3) is most preferable.

Specific but not limited examples of the photoacid generator will be shown below.

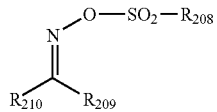

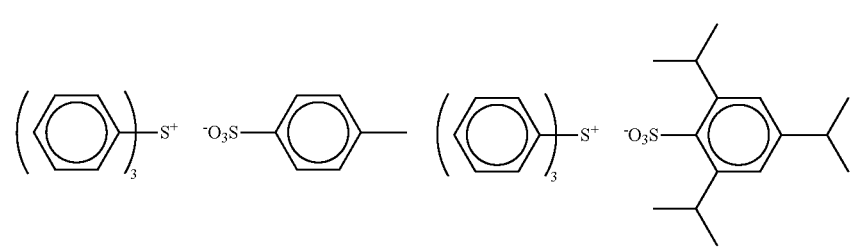

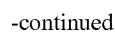
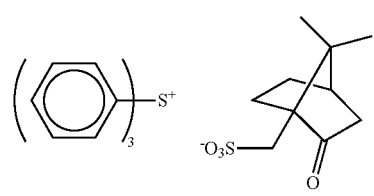
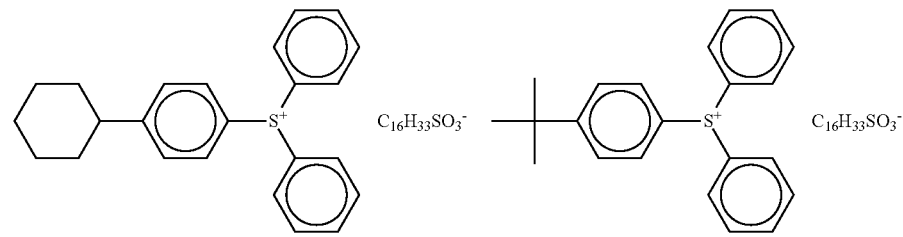
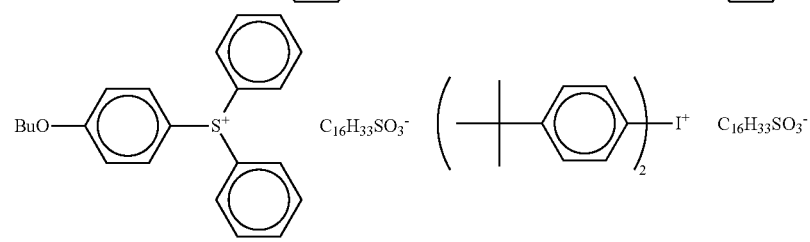
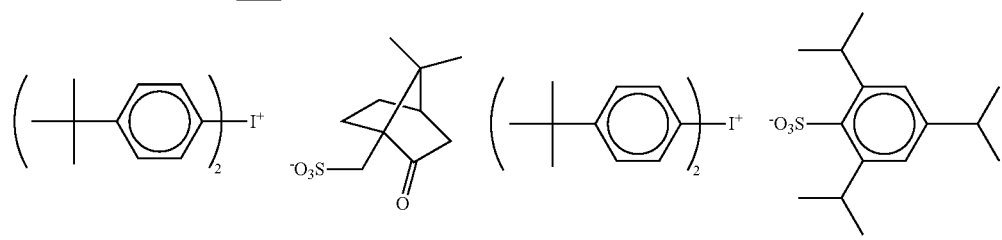
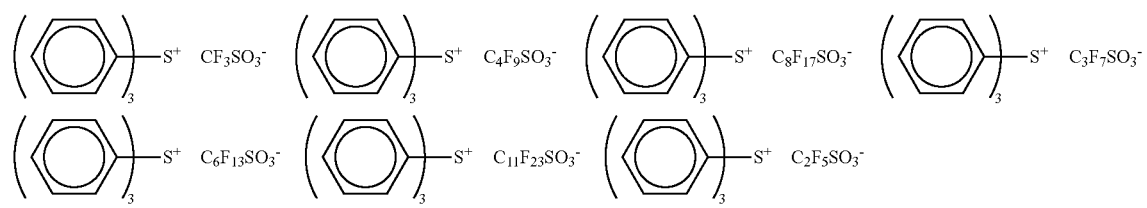
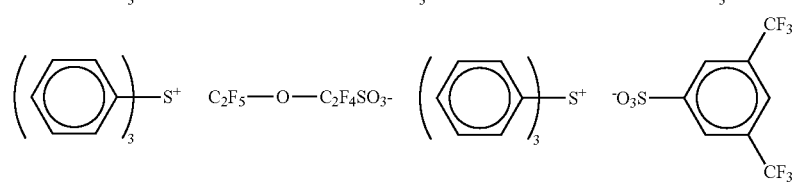
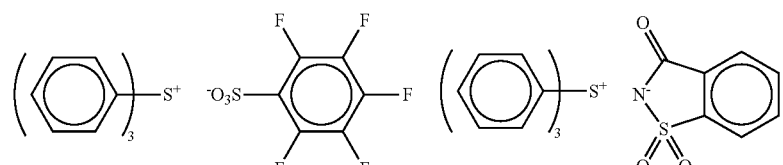
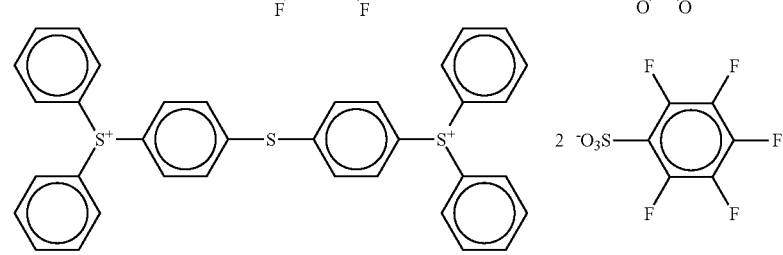

-continued
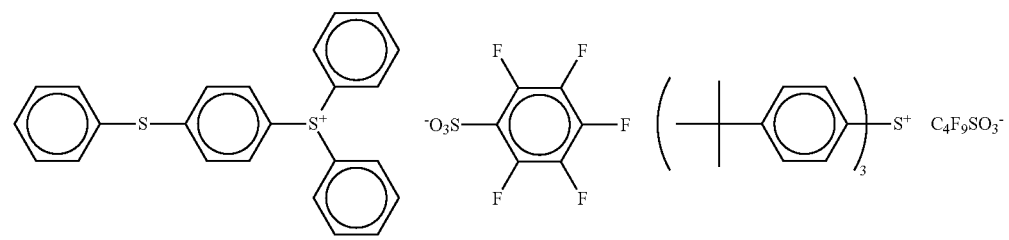
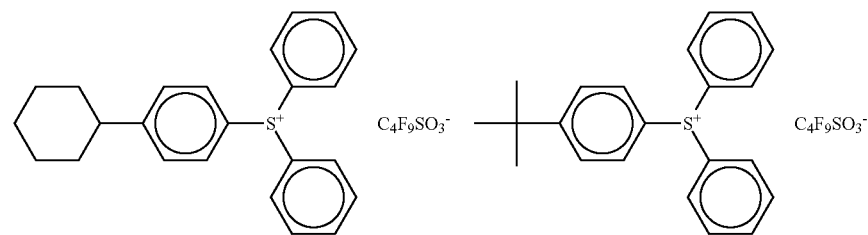
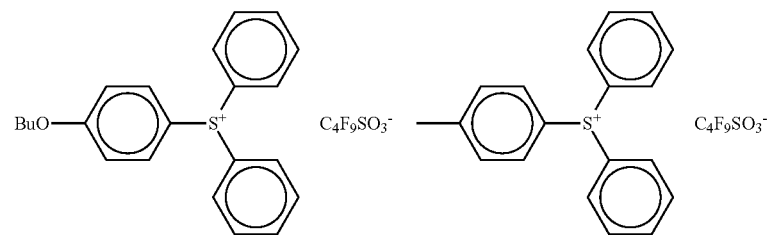
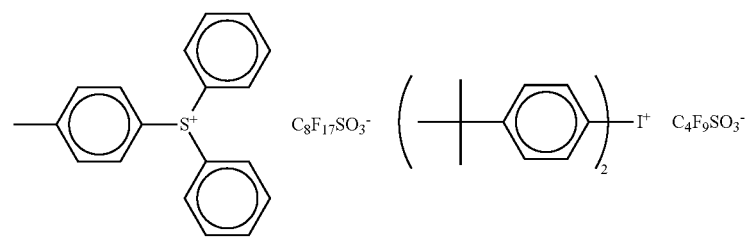
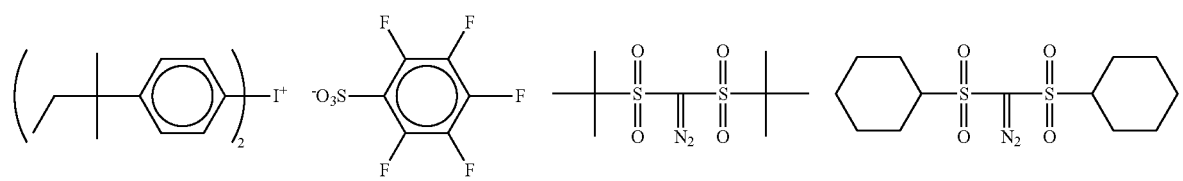
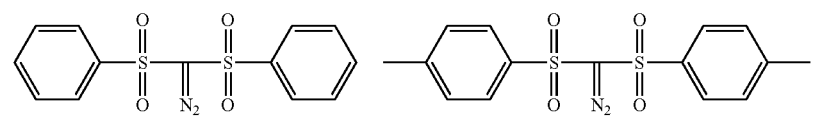
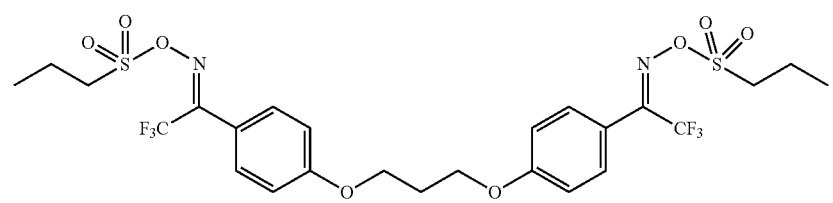
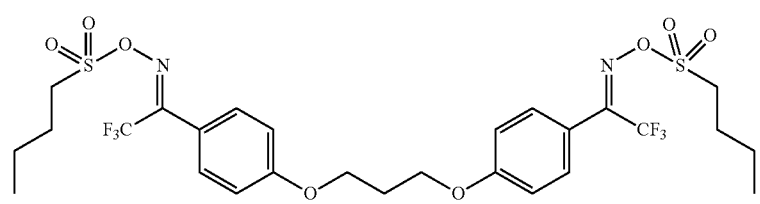

-continued
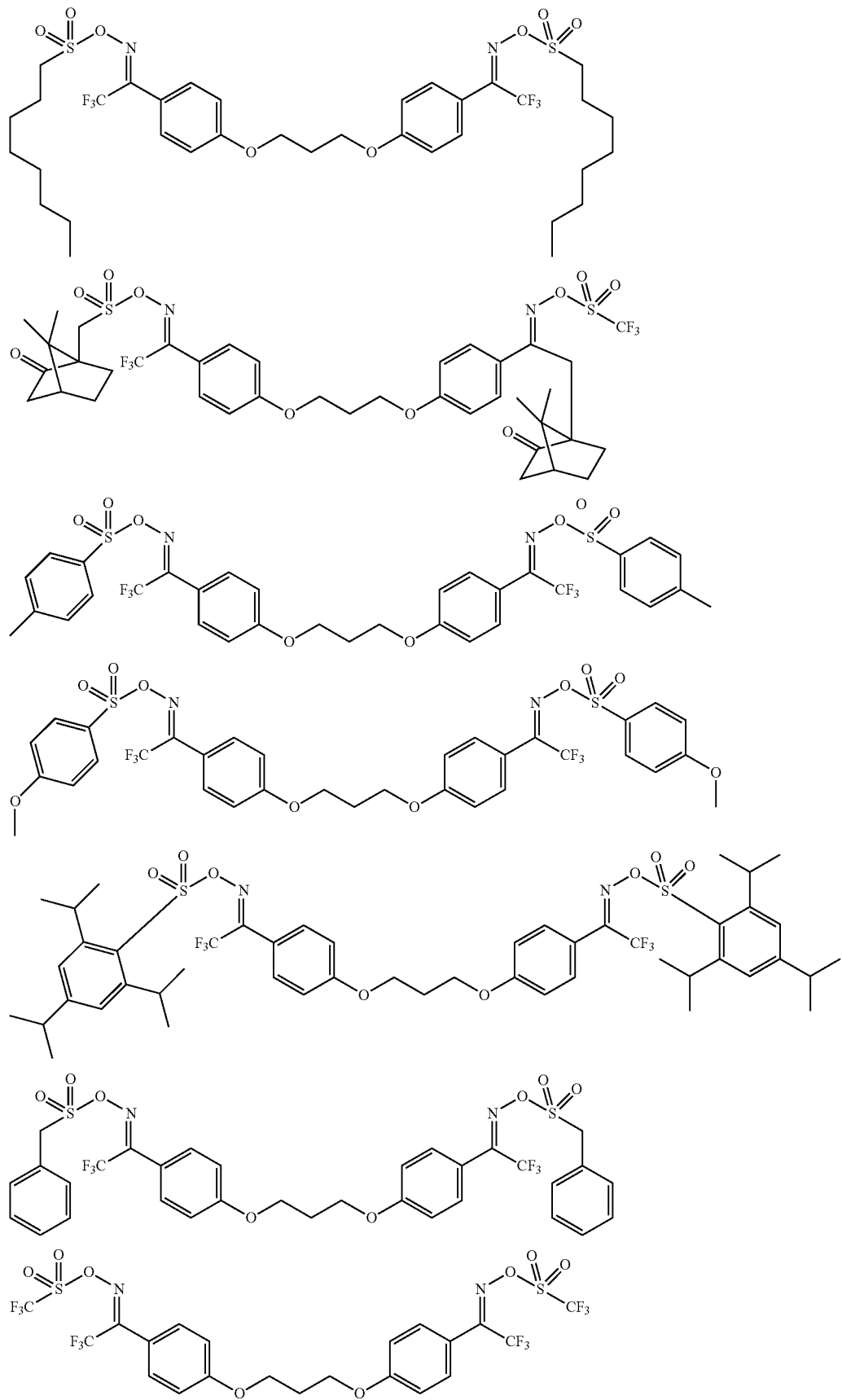

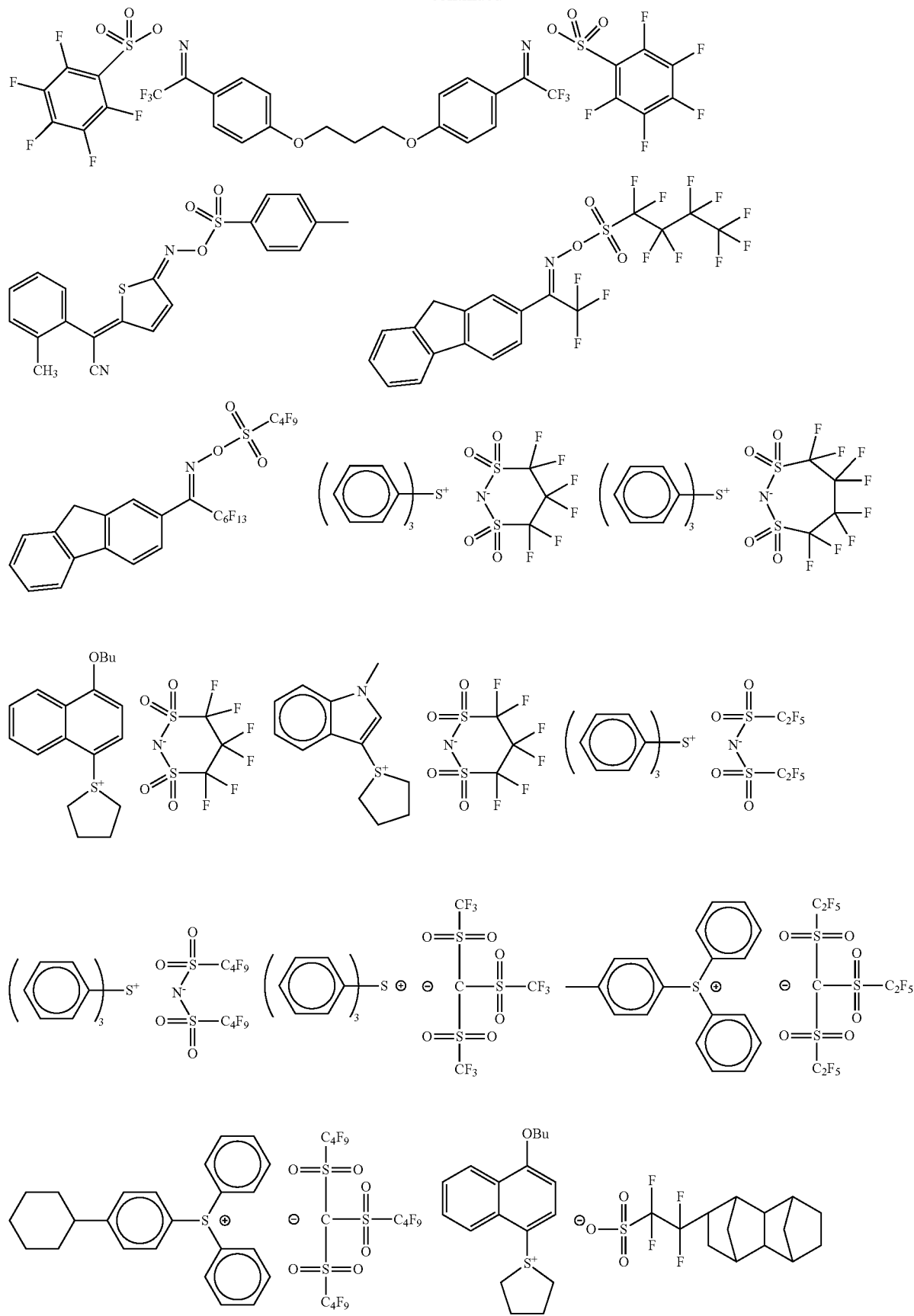

-continued
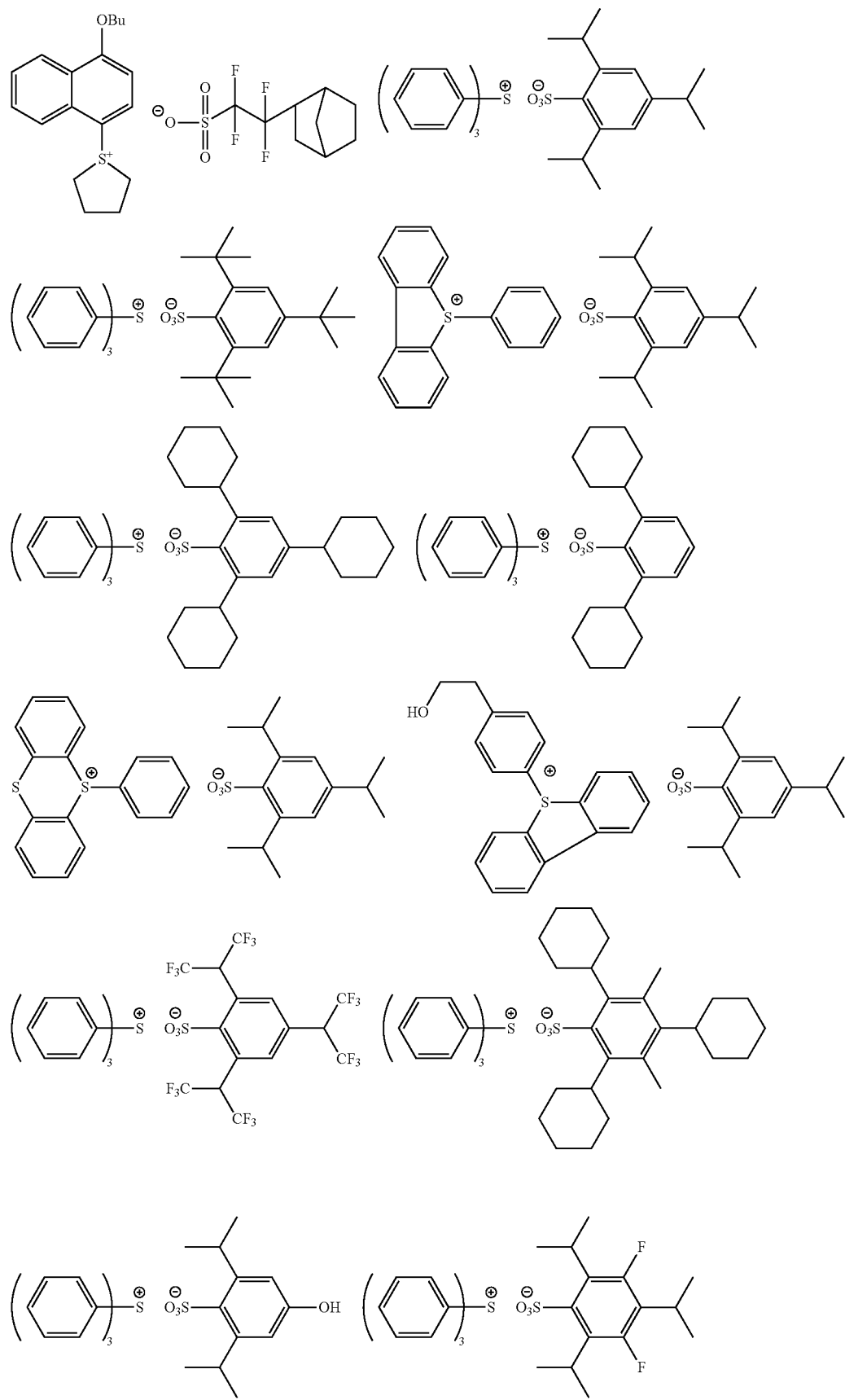

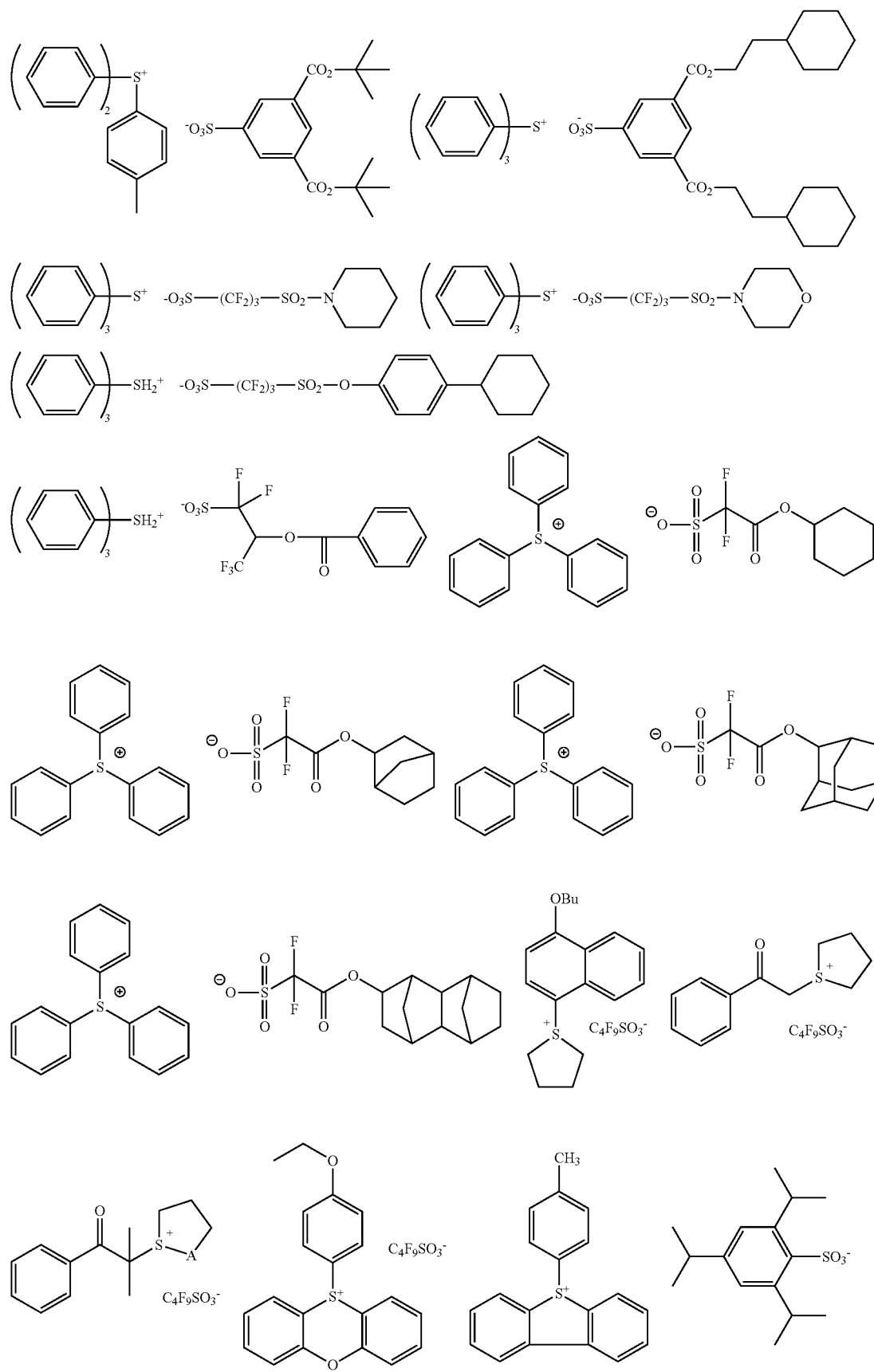

-continued

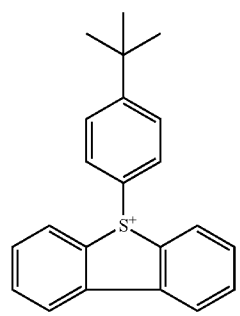 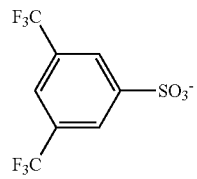 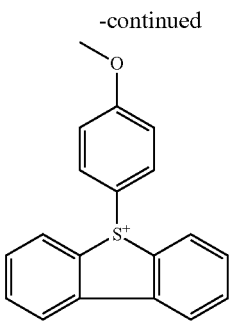 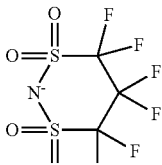

 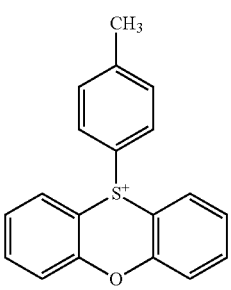 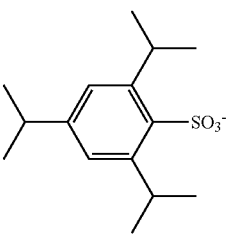

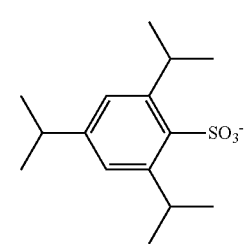 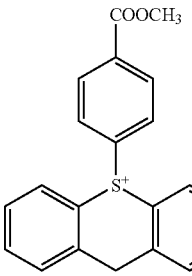 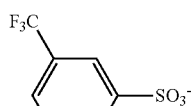

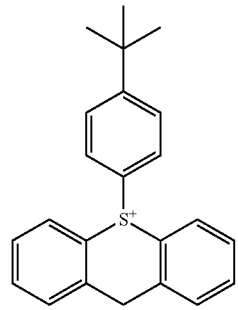 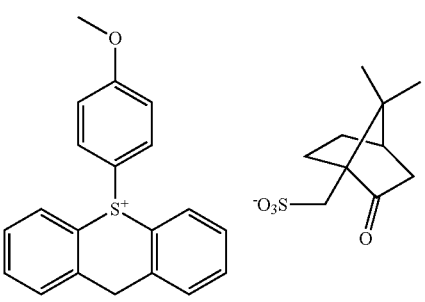

The acid generators can be used either individually or in combination of two or more kinds. When used in combination, compounds generating two kinds of organic acids that the number of atoms other than hydrogen atoms are different from each other and the difference of which is two or more.

The content of the photoacid generator based on the total solids of the composition is preferably in the range of 0.1 to 40 mass %, more preferably 0.5 to 30 mass % and further more preferably 1 to 20 mass %. The content of the photoacid generator based on the total solids of the composition is preferably in the range of 5 to 20 mass % when the composition is used for exposing to EB or EUV.

The volume of generated acid is preferably 200 Å$^3$ or greater, more preferably 300 Å$^3$ or greater and further more preferably 400 Å$^3$ or greater. Further, the volume is preferably up to 2000 Å$^3$, more preferably up to 1500 Å$^3$. An excess increase of the volume may lead to a deterioration of the sensitivity and/or coating solvent solubility. The method of calculating the volume is the same as mentioned hereinbefore.

[3] Resin that is Decomposed, to Thereby Increase its Solubility in an Alkaline Developer when Acted on by an Acid The Resin that is decomposed to thereby increase its solubility in an alkaline developer when acted on by an acid typically contain one or more groups that is decomposed by the action of an acid to thereby generate an alkali-soluble group (hereinafter also referred to as acid-decomposable groups). The resin may contain the acid-decomposable group in its principal chain, in its side chain, or in both thereof. Among them, a resin having an acid-decomposable group in its side chain is preferred.

The acid-decomposable group is preferably a group resulting from substitution of the hydrogen atom of an alkali-soluble group, such as a —COOH group or an —OH group, with an acid-eliminable group. The acid-decomposable group is preferably an acetal group or a tertiary ester group, most preferably an acetal group.

The matrix resin for bonding of the acid-decomposable group as a side chain is an alkali-soluble resin having, in its side chain, an —OH or —COOH group. For example, there can be mentioned the alkali-soluble resins to be described hereinafter.

The alkali dissolution rate of the alkali-soluble resin as measured in a 0.261 N tetramethylammonium hydroxide (TMAH) (23° C.) is preferably 17 nm/sec or greater. The alkali dissolution rate is especially preferably 33 nm/sec or greater.

The alkali-soluble resins especially preferred from this viewpoint include alkali-soluble resins having hydroxystyrene structural units, such as o-, m- or p-poly(hydroxystyrene) and copolymers thereof, hydrogenated poly(hydroxystyrene), halogenated or alkylated poly(hydroxystyrene), poly(hydroxystyrene) having its part O-alkylated or O-acylated, styrene-hydroxystyrene copolymer, α-methylstyrene-hydroxystyrene copolymer and hydrogenated novolak resin and include alkali-soluble resins having carboxylated repeating units, such as those of (meth)acrylic acid and norbornene carboxylic acid.

As repeating units having an acid-decomposable group preferred in the present invention, there can be mentioned, for example, repeating units derived from t-butoxycarbonyloxystyrene, a 1-alkoxyethoxystyrene and a (meth)acrylic acid tertiary alkyl ester. Repeating units derived from a 2-alkyl-2-adamantyl (meth)acrylate and a dialkyl(1-adamantyl)methyl (meth)acrylate are more preferred.

The resin for use in the present invention can be obtained by reaction of a precursor of a group that is eliminated by the action of an acid with an resin or by copolymerization of an alkali-soluble resin monomer having a group that is eliminated by the action of an acid with various monomers, as disclosed in, for example, EP 254853 and JP-A's 2-25850, 3-223860 and 4-251259.

When the composition according to the present invention is exposed to KrF excimer laser beams, electron beams, X-rays or high-energy light rays of 50 nm or less wavelength (EUV, etc.), it is preferred for the resin to have hydroxystyrene repeating units. More preferably, the resin is a copolymer of hydroxystyrene/hydroxystyrene protected by an acid-decomposable group or a modified hydroxystyrene a part of which is protected by a group that is eliminated by the action of an acid.

In particular, the resin is preferably, for example, the one having any of the repeating units of general formula (A) below.

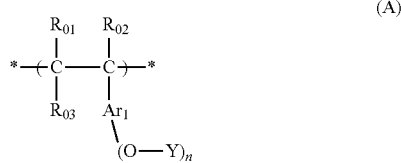

(A)

In the formula, each of $R_{01}$, $R_{02}$ and $R_{03}$ independently represents a hydrogen atom, an alkyl group, a cycloalkyl group, a halogen atom, a cyano group or an alkoxycarbonyl group. $Ar_1$ represents, for example, an aromatic ring group. Alternatively, $R_{03}$ and $Ar_1$ may be simultaneously alkylene groups and bonded to each other so as to form a 5-membered or 6-membered ring in cooperation with —C—C—.

Each of nY s independently represents a hydrogen atom or a group that is eliminated by the action of an acid, provided that at least one of the Ys is a group that is eliminated by the action of an acid.

In the formula, n is an integer of 1 to 4, preferably 1 or 2 and more preferably 1.

As preferred alkyl groups represented by $R_{01}$ to $R_{03}$ in the general formula, there can be mentioned alkyl groups having up to 20 carbon atoms, such as a methyl group, an ethyl group, a propyl group, an isopropyl group, an n-butyl group, a sec-butyl group, a hexyl group, a 2-ethylhexyl group, an octyl group and a dodecyl group. Alkyl groups having up to 8 carbon atoms are more preferred. These alkyl group may contain one or more substituents.

The alkyl groups contained in the alkoxycarbonyl groups are preferably the same as the above-mentioned alkyl groups represented by $R_{01}$ to $R_{03}$.

The cycloalkyl groups may be monocyclic or polycyclic. As preferred examples thereof, there can be mentioned monocyclic alkyl groups having 3 to 8 carbon atoms, such as a cyclopropyl group, a cyclopentyl group and a cyclohexyl group. These cycloalkyl groups may contain one or more substituents.

As the halogen atom, there can be mentioned a fluorine atom, a chlorine atom, a bromine atom or an iodine atom. A fluorine atom is preferred.

As preferred alkylene groups represented by $R_{03}$, there can be mentioned those having 1 to 8 carbon atoms, such as a methylene group, an ethylene group, a propylene group, a butylene group, a hexylene group and an octylene group.

The aromatic ring group represented by $Ar_1$ is preferably an aromatic ring group having 6 to 14 carbon atoms. In particular, there can be mentioned a benzene ring, a toluene ring, a naphthalene ring or the like. These aromatic ring groups may contain one or more substituents.

As the group Y that is eliminated by the action of an acid, there can be mentioned, for example, —C($R_{36}$)($R_{37}$)($R_{38}$), —C(=O)—O—C($R_{36}$) ($R_{37}$)($R_{38}$), —C($R_{01}$)($R_{02}$)(O$R_{39}$), —C($R_{01}$)($R_{02}$)—C(=O)—O—C($R_{36}$)($R_{37}$)($R_{38}$), —CH($R_{36}$)(Ar) or the like.

In the formulae, each of $R_{36}$ to $R_{39}$ independently represents an alkyl group, a cycloalkyl group, an aryl group, an aralkyl group or an alkenyl group. $R_{36}$ and $R_{37}$ may be bonded with each other to thereby form a ring structure.

Each of $R_{01}$ and $R_{02}$ independently represents a hydrogen atom, an alkyl group, a cycloalkyl group, an aryl group, an aralkyl group or an alkenyl group.

Ar represents an aryl group.

The alkyl groups represented by $R_{36}$ to $R_{39}$ and $R_{01}$ and $R_{02}$ each preferably have 1 to 8 carbon atoms. For example, there can be mentioned a methyl group, an ethyl group, a propyl group, an n-butyl group, a sec-butyl group, a hexyl group, an octyl group and the like.

The cycloalkyl groups represented by $R_{36}$ to $R_{39}$ and $R_{01}$ and $R_{02}$ may be monocyclic or polycyclic. The monocyclic alkyl groups are preferably cycloalkyl groups having 3 to 8 carbon atoms. As such, there can be mentioned, for example, a cyclopropyl group, a cyclobutyl group, a cyclopentyl group, a cyclohexyl group, a cyclooctyl group and the like. The polycyclic alkyl groups are preferably cycloalkyl groups having 6 to 20 carbon atoms. As such, there can be mentioned, for example, an adamantyl group, a norbornyl group, an isobornyl group, a camphonyl group, a dicyclopentyl group, an α-pinel group, a tricyclodecanyl group, a tetracyclododecyl group, an androstanyl group and the like. With respect to these, the carbon atoms of each of the cycloalkyl groups may be partially substituted with a heteroatom, such as an oxygen atom.

The aryl groups represented by $R_{36}$ to $R_{39}$, $R_{01}$ and $R_{02}$ and Ar each preferably have 6 to 10 carbon atoms. For example, there can be mentioned a phenyl group, a naphthyl group, an anthryl group and the like.

The aralkyl groups represented by $R_{36}$ to $R_{39}$, $R_{01}$ and $R_{02}$ each preferably have 7 to 12 carbon atoms. For example, there can be mentioned a benzyl group, a phenethyl group, a naphthylmethyl group and the like.

The alkenyl groups represented by $R_{36}$ to $R_{39}$, $R_{01}$ and $R_{02}$ each preferably have 2 to 8 carbon atoms. For example, there can be mentioned a vinyl group, an allyl group, a butenyl group, a cyclohexenyl group and the like.

The ring formed by mutual bonding of $R_{36}$ and $R_{37}$ may be monocyclic or polycyclic. The monocyclic structure is preferably a cycloalkane structure having 3 to 8 carbon atoms. As such, there can be mentioned, for example, a cyclopropane structure, a cyclobutane structure, a cyclopentane structure, a cyclohexane structure, a cycloheptane structure, a cyclooctane structure or the like. The polycyclic structure is preferably a cycloalkane structure having 6 to 20 carbon atoms. As such, there can be mentioned, for example, an adamantane structure, a norbornane structure, a dicyclopentane structure, a tricyclodecane structure, a tetracyclododecane structure or the like. With respect to these, the carbon atoms of each of the cycloalkane structure may be partially substituted with a heteroatom, such as an oxygen atom.

Each of the groups represented by $R_{36}$ to $R_{39}$, $R_{01}$, $R_{02}$, $R_{03}$, Ar and $Ar_1$ may have one or more substituents. As the substituent, there can be mentioned, for example, an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, a nitro group or the like. Preferably, the number of carbon atoms of each of the substituents is up to 8.

The group Y that is eliminated by the action of an acid more preferably has any of the structures of general formula (B) below.

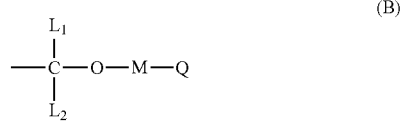

(B)

In the formula, each of $L_1$ and $L_2$ independently represents a hydrogen atom, an alkyl group, a cycloalkyl group, an aryl group or an aralkyl group.

M represents a single bond or a bivalent connecting group.

Q represents an alkyl group, a cycloalkyl group, an alicyclic group, an aromatic ring group, an amino group, an ammonium group, a mercapto group, a cyano group or an aldehyde group. Note that the alicyclic group or the aromatic ring group may contain one or more hetero-atoms.

At least two of Q, M and $L_1$ may be bonded to each other to thereby form a 5-membered or 6-membered ring.

The alkyl groups represented by $L_1$ and $L_2$ are, for example, alkyl groups having 1 to 8 carbon atoms. As preferred examples thereof, there can be mentioned a methyl group, an ethyl group, a propyl group, an n-butyl group, a sec-butyl group, a hexyl group and an octyl group.

The cycloalkyl groups represented by $L_1$ and $L_2$ are, for example, cycloalkyl groups having 3 to 15 carbon atoms. As preferred examples thereof, there can be mentioned a cyclopentyl group, a cyclohexyl group, a norbornyl group and an adamantyl group.

The aryl groups represented by $L_1$ and $L_2$ are, for example, aryl groups having 6 to 15 carbon atoms. As preferred examples thereof, there can be mentioned a phenyl group, a tolyl group, a naphthyl group, an anthryl group and the like.

The aralkyl groups represented by $L_1$ and $L_2$ are, for example, those having 6 to 20 carbon atoms. There can be mentioned a benzyl group, a phenethyl group and the like.

The bivalent connecting group represented by M is, for example, an alkylene group (e.g., a methylene group, an ethylene group, a propylene group, a butylene group, a hexylene group, an octylene group, etc.), a cycloalkylene group (e.g., a cyclopentylene group, a cyclohexylene group, etc.), an alkenylene group (e.g., an ethylene group, a propenylene group, a butenylene group, etc.), an arylene group (e.g., a phenylene group, a tolylene group, a naphthylene group, etc.), —S—, —O—, —CO—, —SO$_2$—, —N(R$_0$)— or a bivalent connecting group resulting from combination of these groups. $R_0$ represents a hydrogen atom or an alkyl group. The alkyl group is, for example, an alkyl group having 1 to 8 carbon atoms such as a methyl group, an ethyl group, a propyl group, an n-butyl group, a sec-butyl group, a hexyl group, an octyl group or the like.

The alkyl group and cycloalkyl group represented by Q are the same as those mentioned above as $L_1$ and $L_2$.

As the alicyclic group and aromatic ring group contained in the alicyclic group optionally containing a heteroatom and aromatic ring group optionally containing a heteroatom represented by Q, there can be mentioned, for example, the cycloalkyl group and aryl group mentioned above as $L_1$ and $L_2$. Preferably, each of the alicyclic group and aromatic ring group has 3 to 15 carbon atoms.

As the alicyclic group containing a heteroatom and aromatic ring group containing a heteroatom represented by Q, there can be mentioned, for example, groups having a heterocyclic structure, such as thiirane, cyclothiorane, thiophene, furan, pyrrole, benzothiophene, benzofuran, benzopyrrole, triazine, imidazole, benzimidazole, triazole, thiadiazole, thiazole and pyrrolidone. However, the alicyclic groups and aromatic ring groups are not limited to these as long as the ring is formed by carbon and a heteroatom or by heteroatoms.

As the ring that may be formed by mutual bonding of at least two of Q, M and $L_1$, there can be mentioned the 5-membered or 6-membered ring resulting from mutual bonding of at least two of Q, M and $L_1$ so as to form, for example, a propylene group or a butylene group. The 5-membered or 6-membered ring contains an oxygen atom.

In the general formula (2), each of the groups represented by $L_1$, $L_2$, M and Q may have one or more substituents. As the substituent, there can be mentioned, for example, an alkyl group, a cycloalkyl group, an aryl group, an amino group, an amido group, an ureido group, an urethane group, a hydroxy group, a carboxy group, a halogen atom, an alkoxy group, a thioether group, an acyl group, an acyloxy group, an alkoxycarbonyl group, a cyano group, and a nitro group. Preferably, the number of carbon atoms of each of the substituents is up to 8.

The groups of the formula -(M-Q) are preferably groups having 1 to 30 carbon atoms, more preferably groups having 5 to 20 carbon atoms. From the viewpoint of outgas suppression, it is especially preferred for the number of carbon atoms to be 6 or greater.

As other preferable resin, those containing repeating units represented by the following general formula (X) can be exemplified.

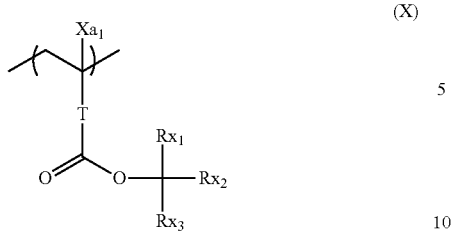
(X)

In general formula (X), $Xa_1$ represents a hydrogen atom, a methyl group, a trifluoromethyl group or a hydroxymethyl group, T represents a single bond or a bivalent connecting group, and each of $Rx_1$ to $Rx_3$ independently represents an alkyl group (linear or branched) or a cycloalkyl group (monocyclic or polycyclic), wherein at least two of $Rx_1$ to $Rx_3$ may be bonded to each other to form a monocyclic or polycyclic cycloalkyl group.

As the bivalent connecting group represented by T, an alkylene group, a group of the formula —COO-Rt-, and a group of the formula —(O-Rt)- can be exemplified. In the formulae, Rt represents an alkylene group or a cycloalkylene group.

T is preferably a single bond or a group of the formula —(COO-Rt)-. Rt is preferably an alkylene group having 1 to 5 carbon atoms, more preferably a —$CH_2$— group or —$(CH_2)_3$— group.

The alkyl group represented by each of $Rx_1$ to $Rx_3$ is preferably one having 1 to 4 carbon atoms, such as a methyl group, an ethyl group, an n-propyl group, an isopropyl group, an n-butyl group, an isobutyl group or a t-butyl group.

The cycloalkyl group represented by each of $Rx_1$ to $Rx_3$ is preferably a monocyclic cycloalkyl group such as a cyclopentyl group or a cyclohexyl group, or a polycyclic cycloalkyl group such as a norbornyl group, a tetracyclodecanyl group, a tetracyclododecanyl group or an adamantyl group.

The cycloalkyl group formed by bonding of at least two of $Rx_1$ to $Rx_3$ is preferably a monocyclic cycloalkyl group such as a cyclopentyl group or a cyclohexyl group, or a polycyclic cycloalkyl group such as a norbornyl group, a tetracyclodecanyl group, a tetracyclododecanyl group or an adamantyl group.

Particularly preferred is an embodiment in which $Rx_1$ is a methyl group or an ethyl group, and $Rx_2$ and $Rx_3$ are bonded to each other to form the above-mentioned cycloalkyl group.

Specific examples of the repeating units represented by the general formula (X) will be shown below, which however in no way limit the scope of the present invention.

In the formulae, Rx represents H, $CH_3$, $CF_3$, or $CH_2OH$. Each of Rxa and Rxb independently represents an alkyl group having 1 to 4 carbon atoms.

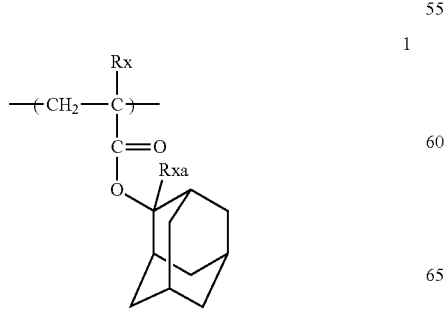

1

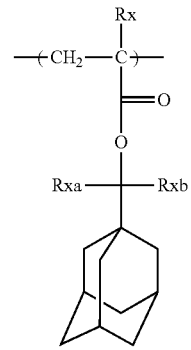

2

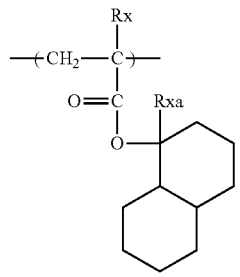

3

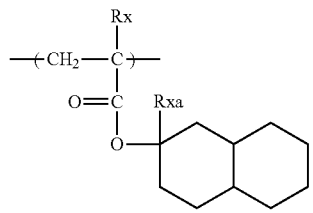

4

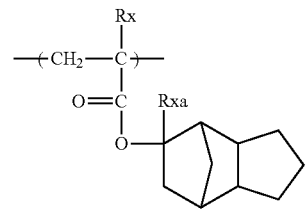

5

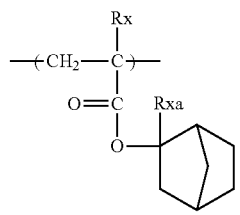

6

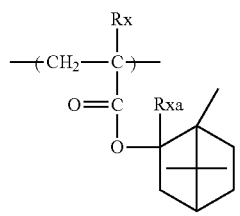

7

8
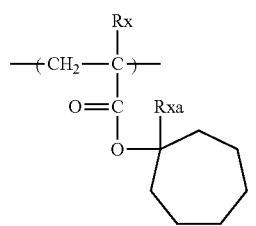
9
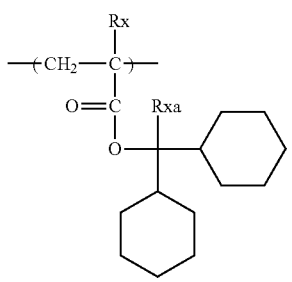
10
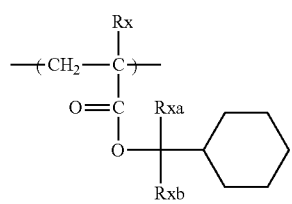
11
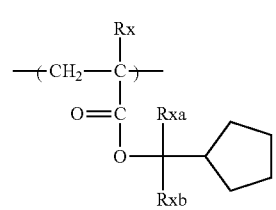
12
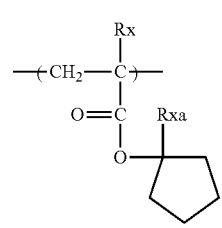
13
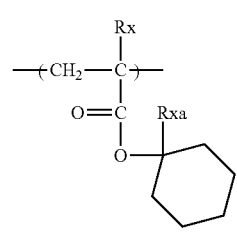
14
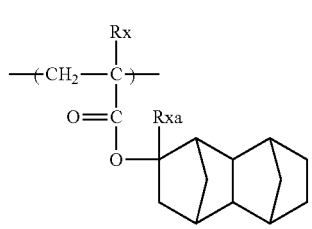
15
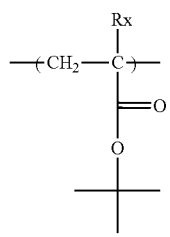
16
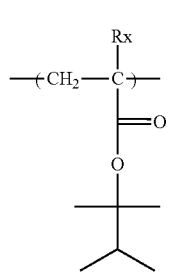
17
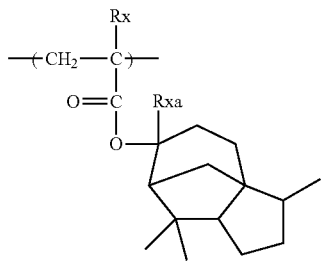
18
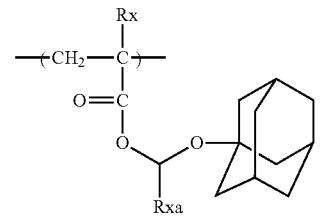
19
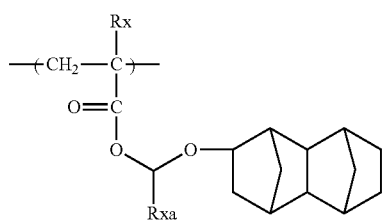
20
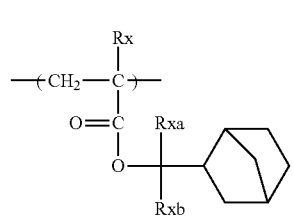

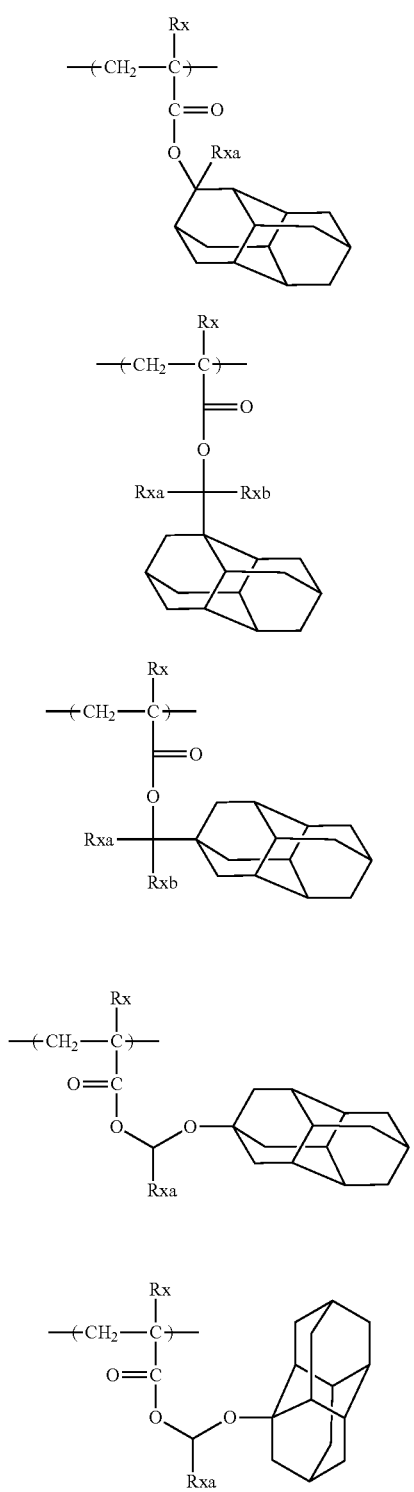
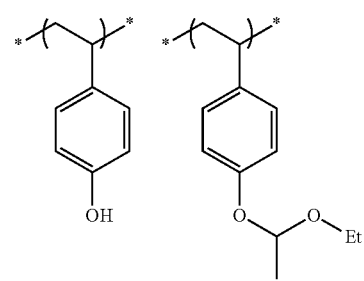
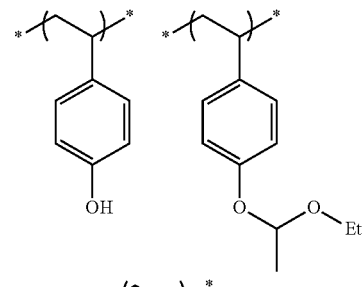
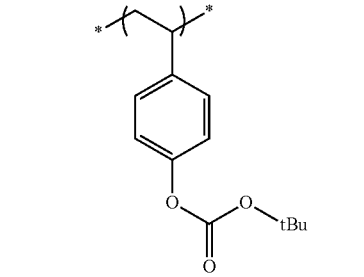
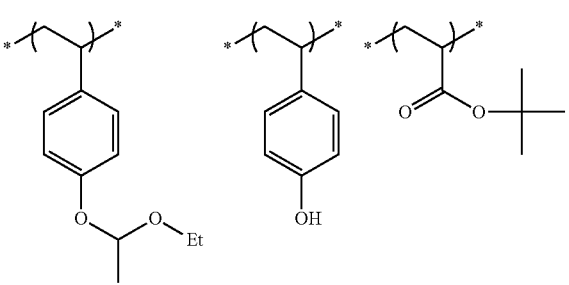
The content of repeating units represented by the general formula (X) based on all the repeating units of the resin is preferably in the range of 3 to 90 mol %, more preferably 5 to 80 mol % and still more preferably 7 to 70 mol %.
Specific examples of the resin explained above will be shown below, which however in no way limit the scope of the present invention.

R-5
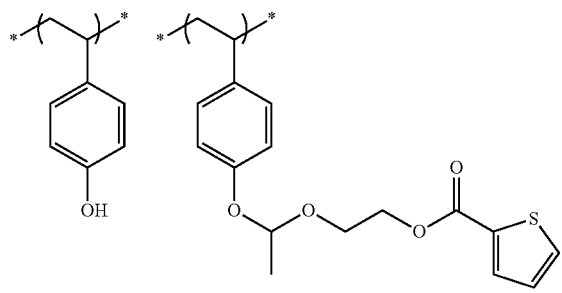
R-6
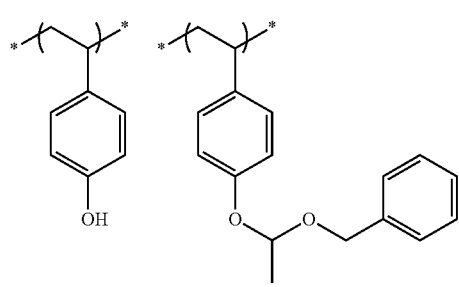
R-7
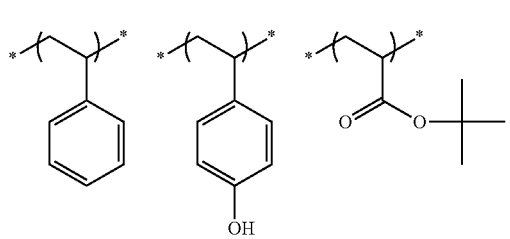
R-8
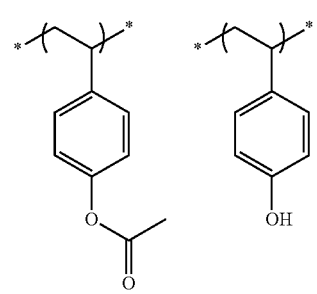
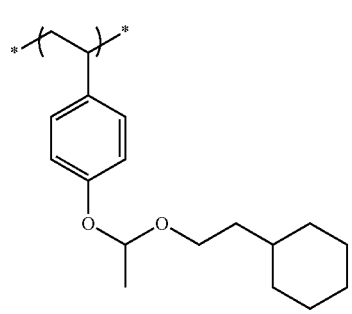
R-9
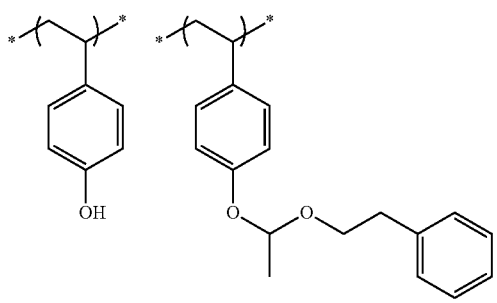
R-10
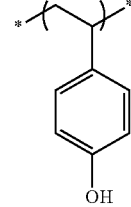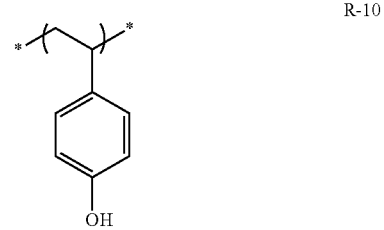
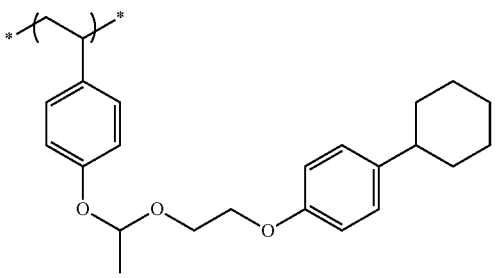
R-11
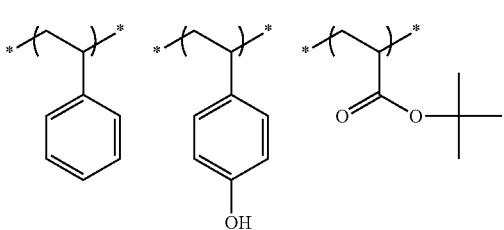

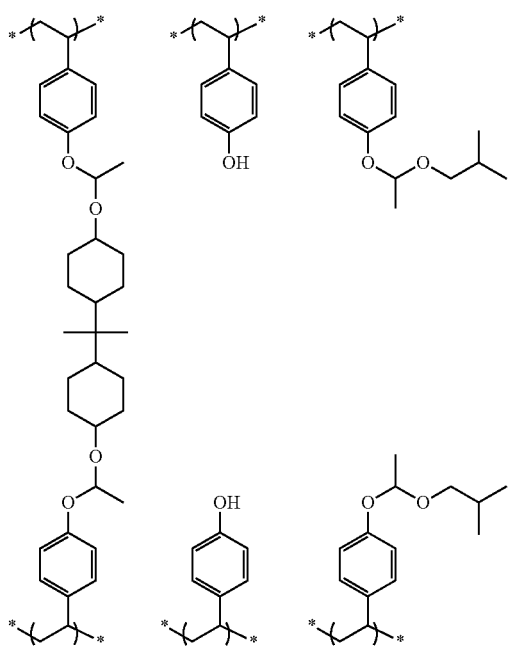
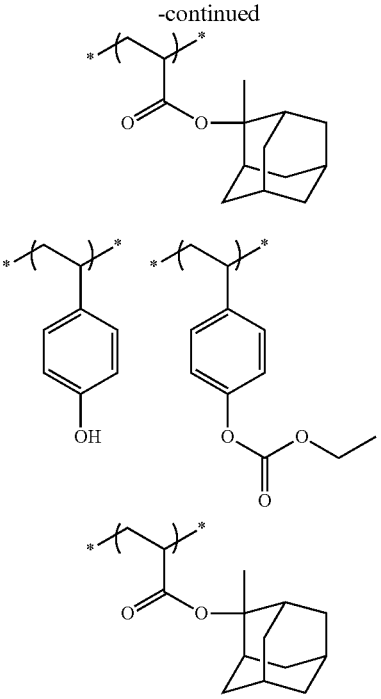
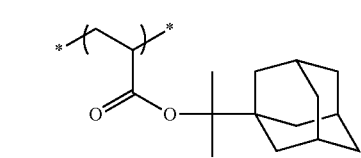
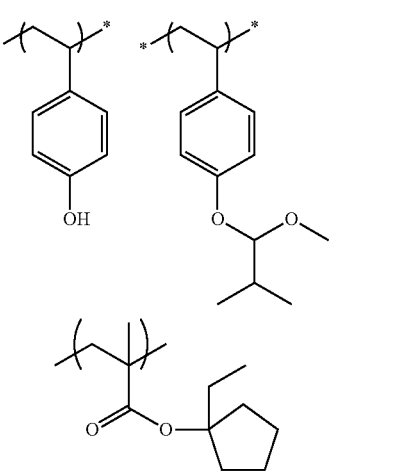

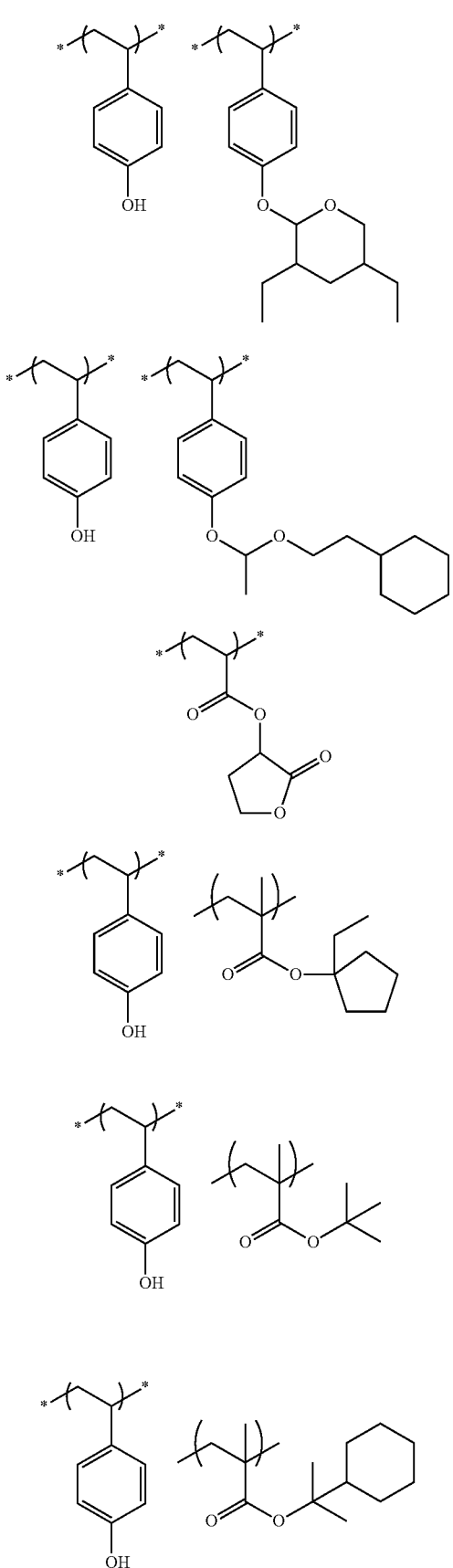

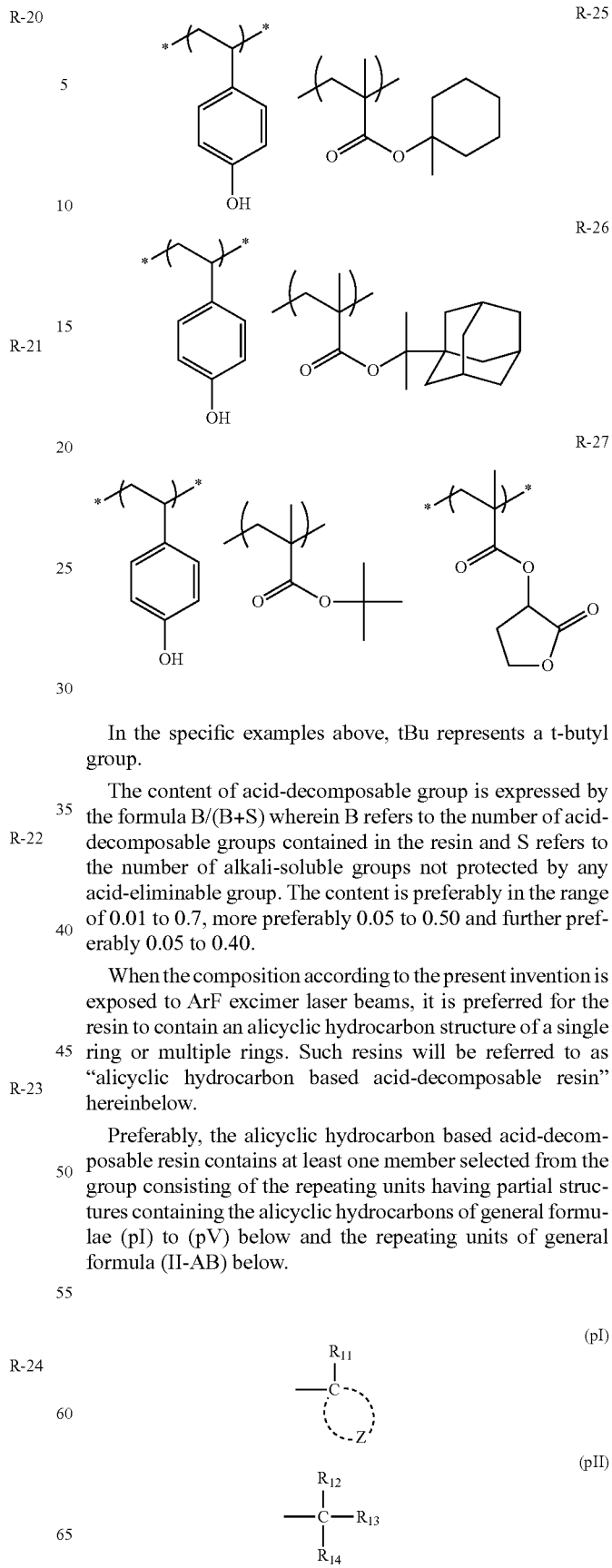

In the specific examples above, tBu represents a t-butyl group.

The content of acid-decomposable group is expressed by the formula B/(B+S) wherein B refers to the number of acid-decomposable groups contained in the resin and S refers to the number of alkali-soluble groups not protected by any acid-eliminable group. The content is preferably in the range of 0.01 to 0.7, more preferably 0.05 to 0.50 and further preferably 0.05 to 0.40.

When the composition according to the present invention is exposed to ArF excimer laser beams, it is preferred for the resin to contain an alicyclic hydrocarbon structure of a single ring or multiple rings. Such resins will be referred to as "alicyclic hydrocarbon based acid-decomposable resin" hereinbelow.

Preferably, the alicyclic hydrocarbon based acid-decomposable resin contains at least one member selected from the group consisting of the repeating units having partial structures containing the alicyclic hydrocarbons of general formulae (pI) to (pV) below and the repeating units of general formula (II-AB) below.

-continued

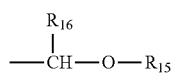
(pIII)

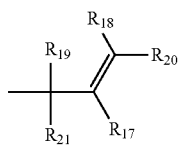
(pIV)

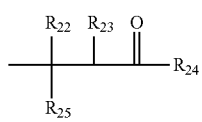
(pV)

In the general formulae (pI) to (pV), $R_{11}$ represents a methyl group, an ethyl group, an n-propyl group, an isopropyl group, an n-butyl group, an isobutyl group or a sec-butyl group, and Z represents anatomic group required for formation of a cycloalkyl group in cooperation with a carbon atom.

Each of $R_{12}$ to $R_{16}$ independently represents a cycloalkyl group or a linear or branched alkyl group having 1 to 4 carbon atoms, provided that at least one of $R_{12}$ to $R_{14}$ and either $R_{15}$ or $R_{16}$ represents a cycloalkyl group.

Each of $R_{17}$ to $R_{21}$ independently represents a hydrogen atom or a cycloalkyl group or a linear or branched alkyl group having 1 to 4 carbon atoms, provided that at least one of $R_{17}$ to $R_{21}$ represents a cycloalkyl group. Either $R_{19}$ or $R_{21}$ represents a cycloalkyl group or a linear or branched alkyl group having 1 to 4 carbon atoms.

Each of $R_{22}$ to $R_{25}$ independently represents a hydrogen atom or a cycloalkyl group or a linear or branched alkyl group having 1 to 4 carbon atoms, provided that at least one of $R_{22}$ to $R_{25}$ represents a cycloalkyl group. $R_{23}$ and $R_{24}$ may be bonded to each other to thereby form a ring.

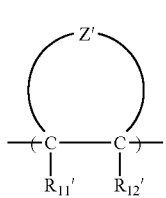
(II-AB)

In the general formula (II-AB), each of $R_{11}'$ and $R_{12}'$ independently represents a hydrogen atom, a cyano group, a halogen atom or an alkyl group.

Z' represents an atomic group for formation of an alicyclic structure wherein two bonded carbon atoms (C—C) are contained.

Further preferably, the general formula (II-AB) is either general formula (II-AB1) or general formula (II-AB2) below.

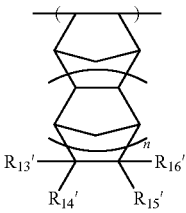
(II-AB1)

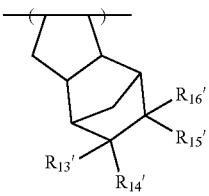
(II-AB2)

In the general formulae (II-AB1) and (II-AB2), each of $R_{13}'$ to $R_{16}'$ independently represents a hydrogen atom, a halogen atom, a cyano group, a hydroxyl group, —COOH, —COOR$_5$, a group that is decomposed by the action of an acid, —C(=O)—X-A'-R$_{17}'$, an alkyl group or a cycloalkyl group. In the above formula, $R_5$ represents an alkyl group, a cycloalkyl group or a group with a lactone structure. X represents an oxygen atom, a sulfur atom, —NH—, —NHSO$_2$— or —NHSO$_2$NH—. A' represents a single bond or a bivalent connecting group. $R_{17}'$ represents —COOH, —COOR$_5$, —CN, a hydroxyl group, an alkoxy group, —CO—NH—R$_6$, —CO—NH—SO$_2$—R$_6$ or a group with a lactone structure. $R_6$ represents an alkyl group or a cycloalkyl group. At least two of $R_{13}'$ to $R_{16}'$ may be bonded to each Other to thereby form a ring.

n represents 0 or 1.

In the general formulae (pI) to (pV), each of the alkyl groups represented by $R_{12}$ to $R_{25}$ is a linear or branched alkyl group having 1 to 4 carbon atoms. As such, there can be mentioned, for example, a methyl group, an ethyl group, a propyl group, an n-butyl group, a sec-butyl group, a t-butyl group or the like.

The cycloalkyl groups represented by $R_{12}$ to $R_{25}$ and the cycloalkyl group formed by Z and a carbon atom may be monocyclic or polycyclic. In particular, there can be mentioned groups of a monocyclo, bicyclo, tricyclo or tetracyclo structure or the like having 5 or more carbon atoms. The number of carbon atoms thereof is preferably in the range of 6 to 30, especially preferably 7 to 25.

As preferred cycloalkyl groups, there can be mentioned an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group and a cyclododecanyl group. As more preferred cycloalkyl groups, there can be mentioned an adamantyl group, a norbornyl group, a cyclohexyl group, a cyclopentyl group, a tetracyclododecanyl group and a tricyclodecanyl group.

These alkyl groups and cycloalkyl groups may further have substituents. As substituents that can be introduced in the alkyl groups and cycloalkyl groups, there can be mentioned an alkyl group (1 to 4 carbon atoms), a halogen atom, a hydroxyl group, an alkoxy group (1 to 4 carbon atoms), a carboxyl group and an alkoxycarbonyl group (2 to 6 carbon atoms). These substituents may further have substituents. As substituents that can be further introduced in the alkyl groups, alkoxy groups, alkoxycarbonyl groups, etc., there can be mentioned a hydroxyl group, a halogen atom and an alkoxy group.

The structures of the general formulae (pI) to (pV) employed in the above resin can be used for the protection of the alkali-soluble groups. As the alkali-soluble groups, there can be mentioned various groups generally known in this technical field.

In particular, there can be mentioned, for example, structures resulting from replacement of a hydrogen atom of a carboxylic acid, group, sulfonic acid group, phenol group or thiol group with any of the structures of the general formulae (pI) to (pV). Structures resulting from replacement of a hydrogen atom of a carboxylic acid group or sulfonic acid group with any of the structures of the general formulae (pI) to (pV) are preferred.

As preferred repeating units having any of the alkali-soluble groups protected by the structures of the general formulae (pI) to (pV), there can be mentioned those of general formula (pA) below.

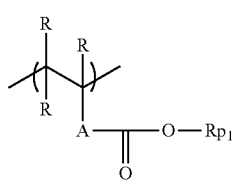

(pA)

In the general formula (pA), R represents a hydrogen atom, a halogen atom or a linear or branched alkyl group having 1 to 4 carbon atoms. Two or more Rs may be identical to or different from each other.

A represents any one or a combination of two or more groups selected from the group consisting of a single bond, an alkylene group, an ether group, a thioether group, a carbonyl group, an ester group, an amido group, a sulfonamido group, a urethane group and a urea group, and a combination thereof. A single bond is preferred.

$Rp_1$ represents any of the groups of the above general formulae (pI) to (pV).

The repeating units of the general formula (pA) are most preferably those derived from a 2-alkyl-2-adamantyl (meth)acrylate and a dialkyl(1-adamantyl)methyl (meth)acrylate.

Specific examples of the repeating units of the general formula (pA) will be shown below.

1

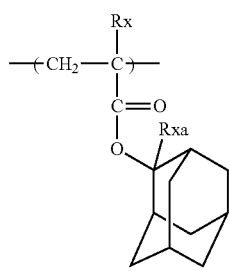

2

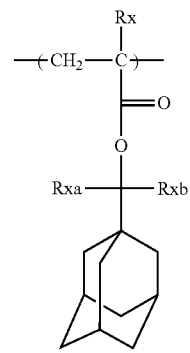

3

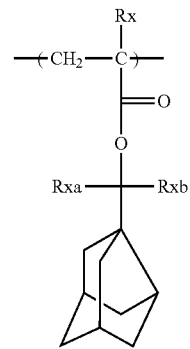

4

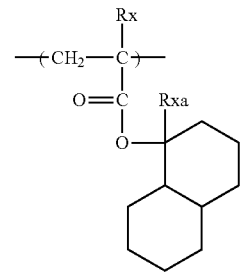

5

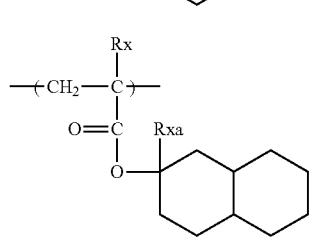

6

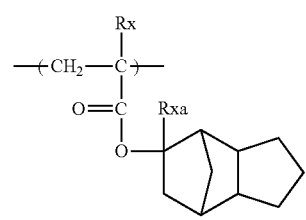

7

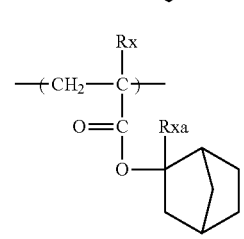

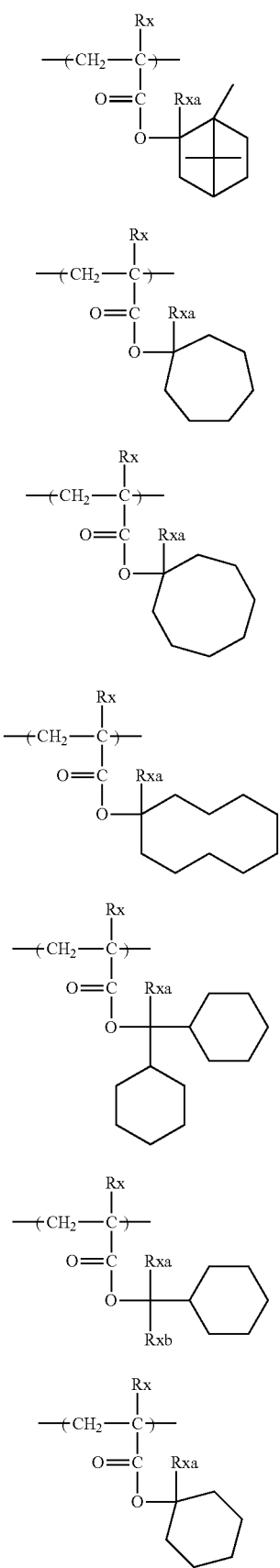

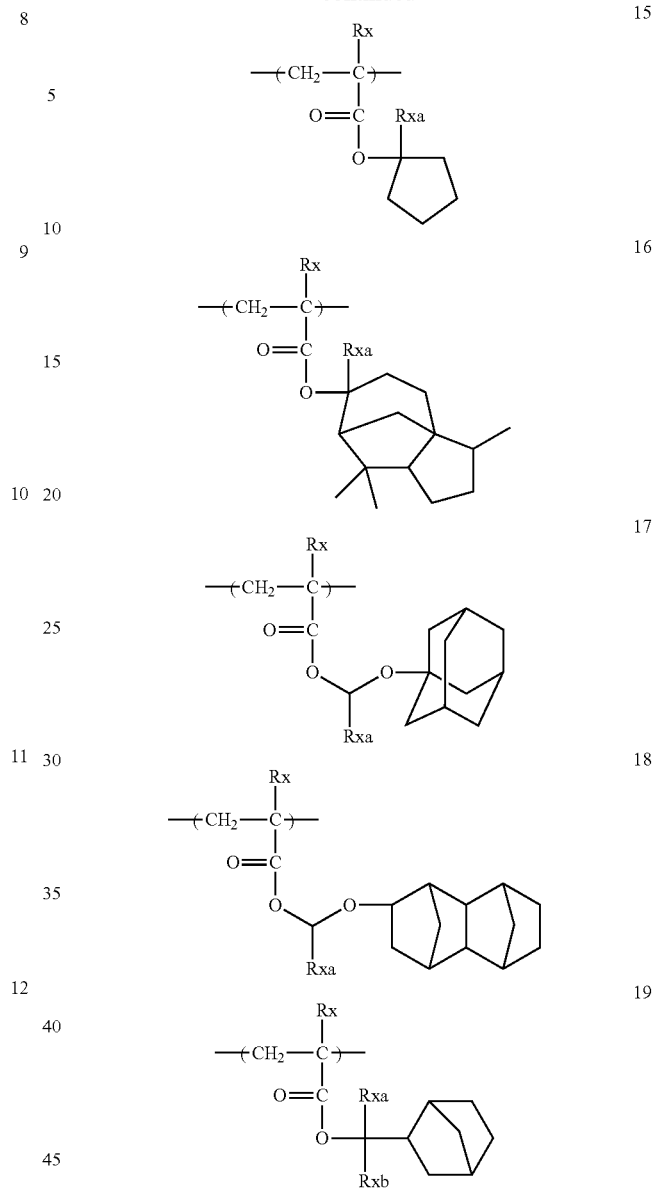

In the above structural formulae, Rx represents H, CH$_3$, CF$_3$ or CH$_2$OH. Each of Rxa and Rxb independently represents an alkyl group having 1 to 4 carbon atoms.

In the general formula (II-AB), the halogen atoms represented by R$_{11}$' and R$_{12}$' include a chlorine atom, a bromine atom, a fluorine atom, an iodine atom, etc.

The alkyl groups represented by R$_{11}$' and R$_{12}$' are preferably linear or branched alkyl groups each having 1 to 10 carbon atoms. For example, there can be mentioned a methyl group, an ethyl group, an n-propyl group, an isopropyl group, a linear or branched butyl, pentyl, hexyl or heptyl group, and the like.

The atomic group represented by Z' is an atomic group capable of providing the resin with a repeating unit of optionally substituted alicyclic hydrocarbon. The atomic group is especially preferably one capable of providing a bridged alicyclic structure for formation of a bridged alicyclic hydrocarbon repeating unit.

The provided alicyclic hydrocarbon skeleton can be the same as that of the cycloalkyl groups represented by $R_{12}$ to $R_{25}$ in the general formulae (pI) to (pV).

The alicyclic hydrocarbon skeleton may have one or more substituents. As the substituent, there can be mentioned any of the atoms or groups represented by $R_{13}'$ to $R_{16}'$ in the general formulae (II-AB1) and (II-AB2).

In the alicyclic hydrocarbon based acid-decomposable resin, the group that is decomposed by the action of an acid can be contained in at least one repeating unit selected from among the repeating units having partial structures containing the alicyclic hydrocarbons of the general formulae (pI) to (pV), the repeating units of general formula (II-AB) and the repeating units of copolymer components to be described below.

Any of the various substituents that can be introduced in $R_{13}'$ to $R_{16}'$ in the general formulae (II-AB1) and (II-AB2) can be a substituent for the atomic groups for formation of the alicyclic structures of the general formula (II-AB) or the atomic groups Z' for formation of the bridged alicyclic structures.

Specific examples of the repeating units of the above general formulae (II-AB1) and (II-AB2) will be shown below, which however in no way limit the scope of the present invention.

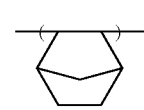
[II-1]

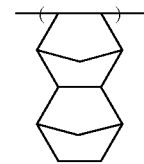
[II-2]

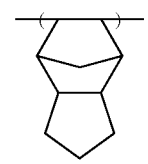
[II-3]

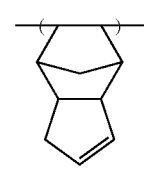
[II-4]

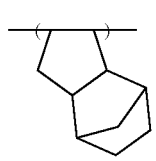
[II-5]

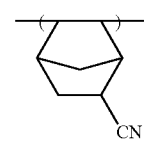
[II-6]

-continued

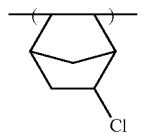
[II-7]

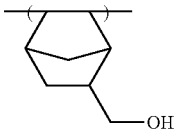
[II-8]

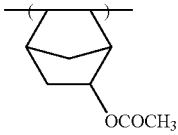
[II-9]

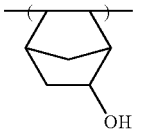
[II-10]

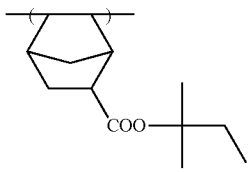
[II-11]

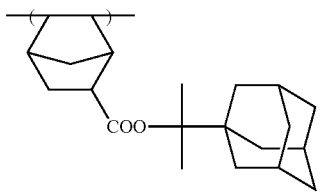
[II-12]

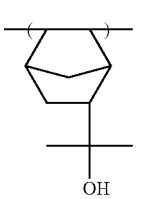
[II-13]

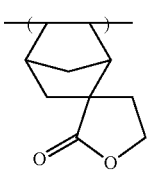
[II-14]

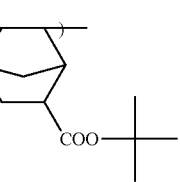
[II-15]

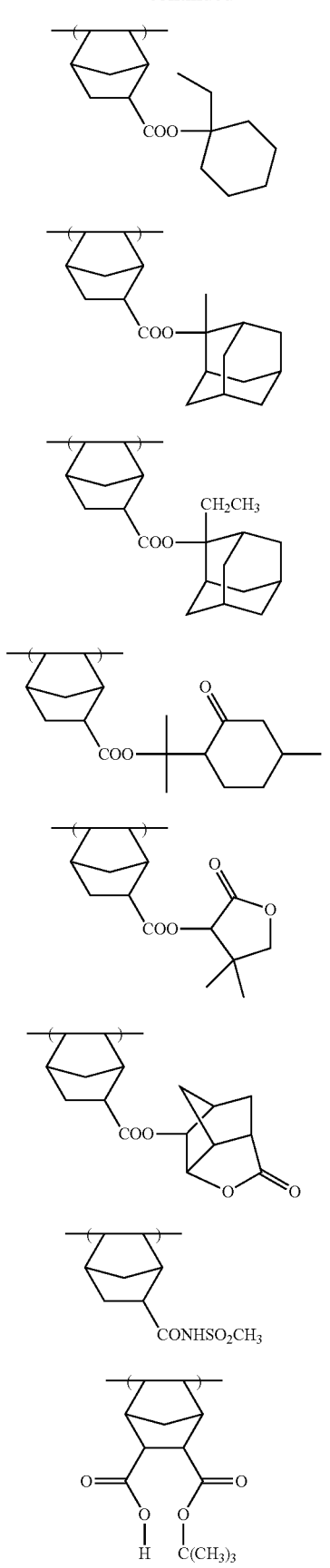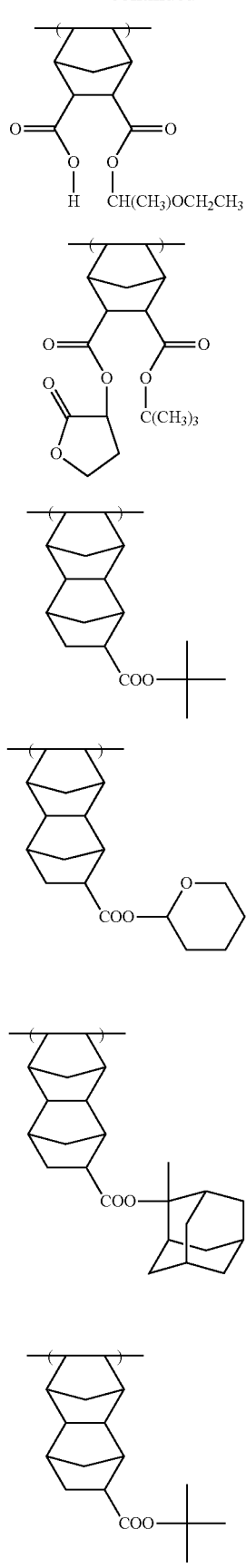

-continued

[II-30]

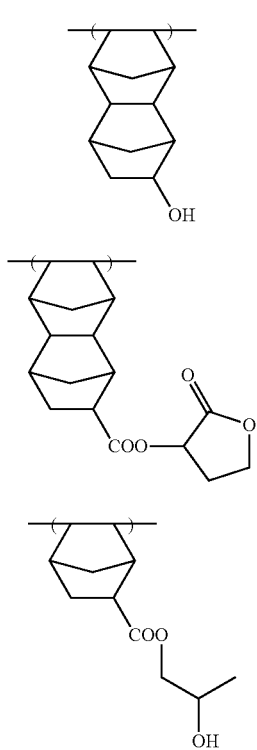

[II-31]

[II-32]

It is preferred for the alicyclic hydrocarbon based acid-decomposable resin to have a repeating unit having a lactone group. As a lactone group, a group with a 5 to 7-membered ring lactone structure is preferred, and a group resulting from condensation of lactone structures of a 5 to 7-membered ring with other cyclic structures effected in a fashion to form a bicyclo structure or spiro structure are especially preferred.

More preferably, the alicyclic hydrocarbon based acid-decomposable resin has a repeating unit having a lactone structure represented by any of general formulae (LC1-1) to (LC1-17) below. The groups with lactone structures may be directly bonded to the principal chain of the resin. Preferred lactone structures are those of the formulae (LC1-1), (LC1-4), (LC1-5), (LC1-6), (LC1-13), (LC1-14), and (LC1-17). The use of these specified lactone structures would realize improvement in the line edge roughness and development defect.

LC1-1

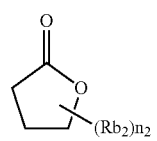

LC1-2

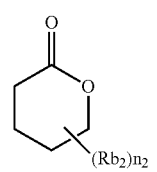

-continued

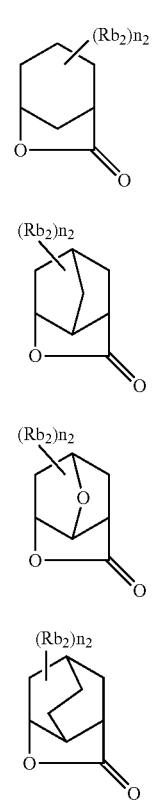

LC1-3

LC1-4

LC1-5

LC1-6

LC1-7

LC1-8

LC-9

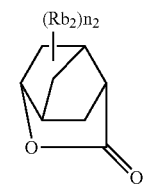

LC-10

LC1-11
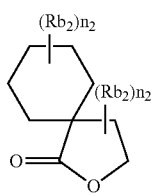

LC1-12
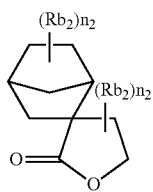

LC1-13
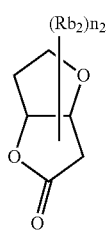

LC1-14
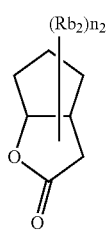

LC1-15

LC1-16
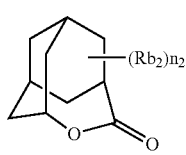

LC1-17
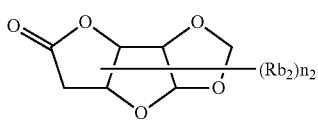

The presence of a substituent ($Rb_2$) on the portion of the lactone structure is optional. As preferred substituents ($Rb_2$), there can be mentioned an alkyl group having 1 to 8 carbon atoms, a cycloalkyl group having 3 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, an acid-decomposable group and the like.

In the formulae, $n_2$ is an integer of 0 to 4. When $n_2$ is an integer of 2 or greater, the plurality of present substituents ($Rb_2$) may be identical to or different from each other. Further, the plurality of present substituents ($Rb_2$) may be bonded to each other to thereby form a ring.

As the repeating units having the groups with lactone structures of any of the general formulae (LC1-1) to (LC1-17), there can be mentioned the repeating units of the general formulae (II-AB1) and (II-AB2) wherein at least one of R13' to R16' has any of the groups of the general formulae (LC1-1) to (LC1-17) as well as the repeating units of general formula (AI) below. Examples of the former include a structure in which the $R_5$ of —$COOR_5$ represents any of the groups of the general formulae (LC1-1) to (LC1-17).

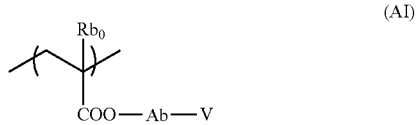
(AI)

In the general formula (AI), $Rb_0$ represents a hydrogen atom, a halogen atom or an alkyl group having 1 to 4 carbon atoms.

As the alkyl group represented by $Rb_0$, there can be mentioned, for example, a methyl group, an ethyl group, a propyl group, an n-butyl group, a sec-butyl group, a t-butyl group or the like. The alkyl group represented by $Rb_0$ may have one or more substituents. As preferred substituents that may be introduced in the alkyl group represented by $Rb_0$, there can be mentioned, for example, a hydroxyl group and a halogen atom.

As the halogen atom represented by $Rb_0$, there can be mentioned a fluorine atom, a chlorine atom, a bromine atom or an iodine atom.

The $Rb_0$ is preferably a hydrogen atom or a methyl group.

Ab represents an alkylene group, a bivalent connecting group with an alicyclic hydrocarbon structure of a single ring or multiple rings, a single bond, an ether group, an ester group, a carbonyl group, a carboxyl group or a bivalent connecting group resulting from combination of these. A single bond and a connecting group of the formula -$Ab_1$-$CO_2$— are preferred.

$Ab_1$ is a linear or branched alkylene group or a cycloalkylene group of a single ring or multiple rings, being preferably a methylene group, an ethylene group, a cyclohexylene group, an adamantylene group or a norbornylene group.

V represents any of the groups of the general formulae (LC1-1) to (LC1-17).

The repeating unit having a lactone structure is generally present in the form of optical isomers. Any of the optical isomers may be used. It is both appropriate to use a single type of optical isomer alone and to use a plurality of optical isomers in the form of a mixture. When a single type of optical isomer is mainly used, the optical purity thereof is preferably 90% ee or higher, more preferably 95% ee or higher.

Especially preferred repeating units containing lactone group, the followings can be exemplified. Selecting the best lactone group can improve a pattern profile and iso-dense dependense. In the formulae below, each of Rx and R independently represents H, $CH_3$, $CH_2OH$, or $CF_3$.

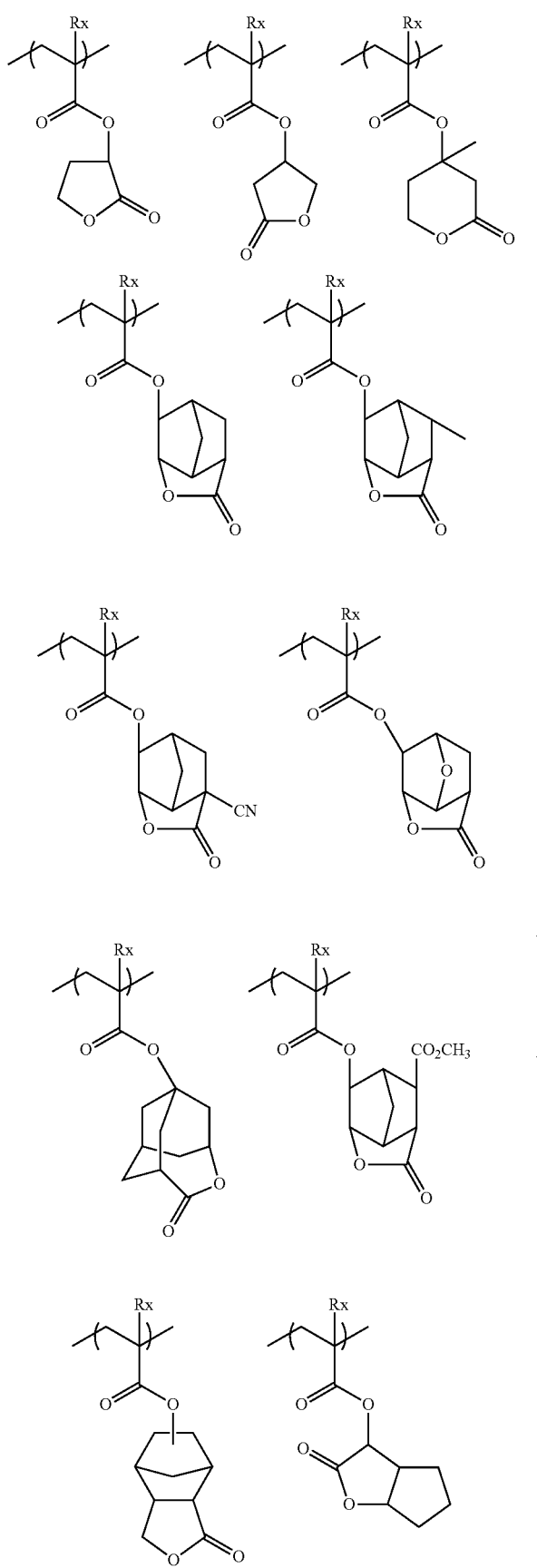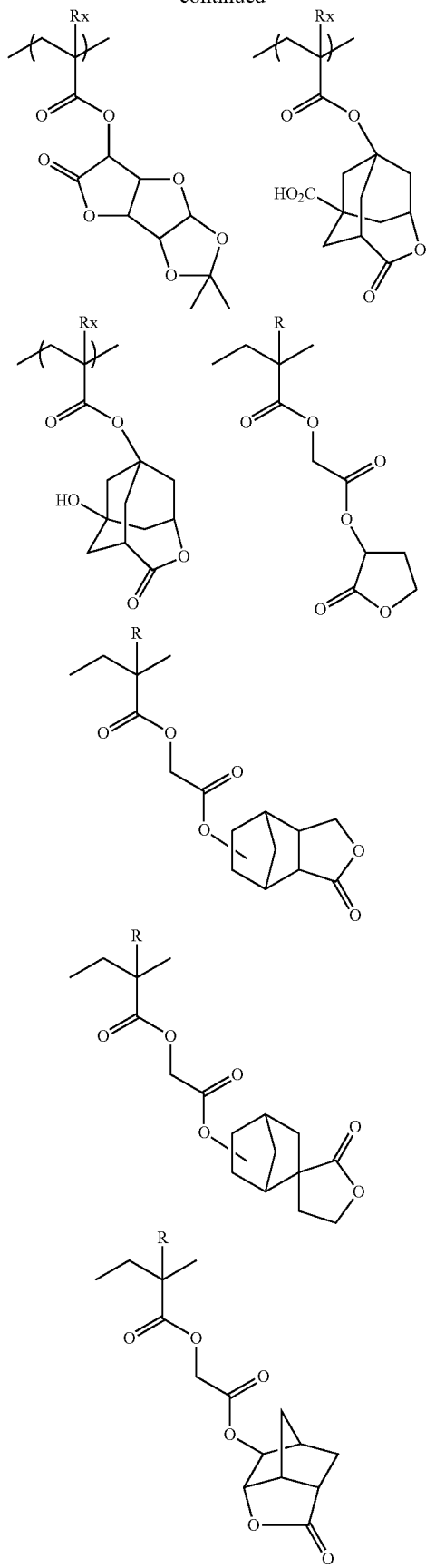

| 99 -continued | 100 -continued |
|---|---|
| 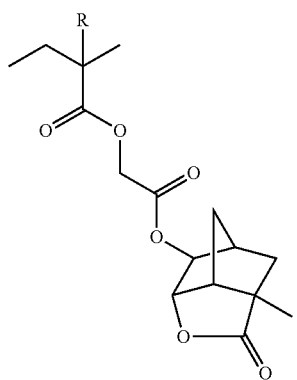 | 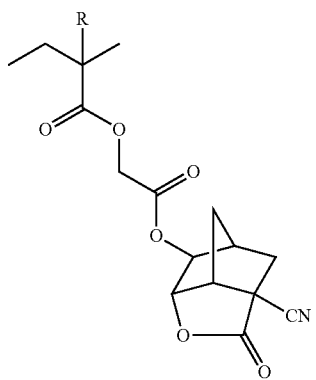 |
| 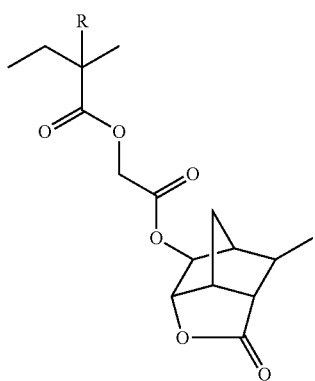 | 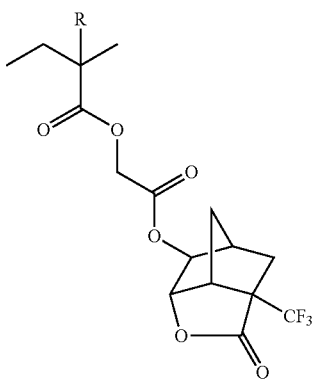 |
| 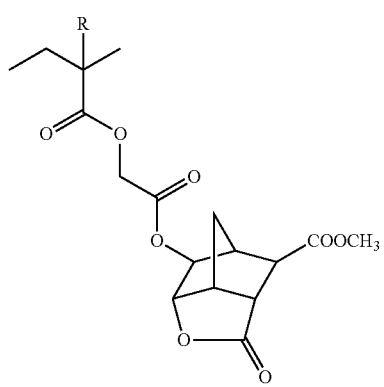 | 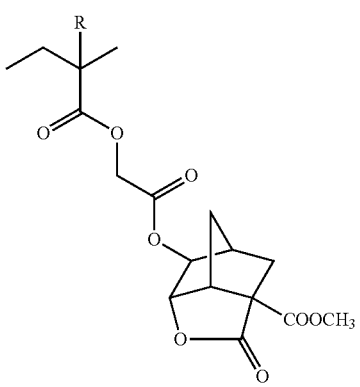 |
| 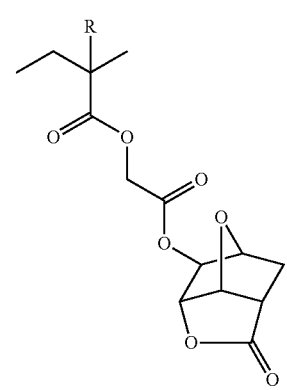 | 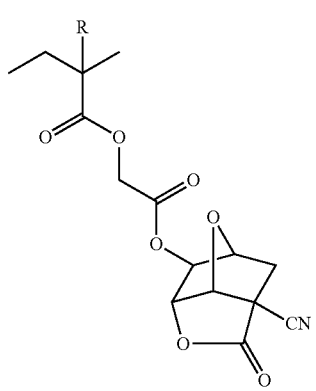 |

101
-continued
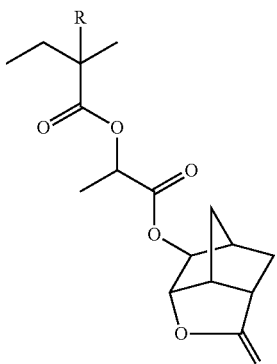
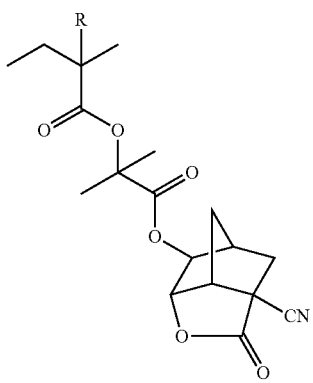
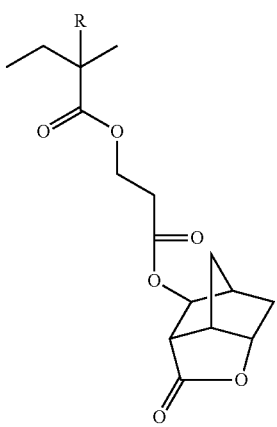
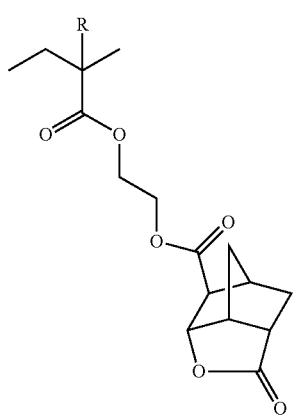
102
-continued
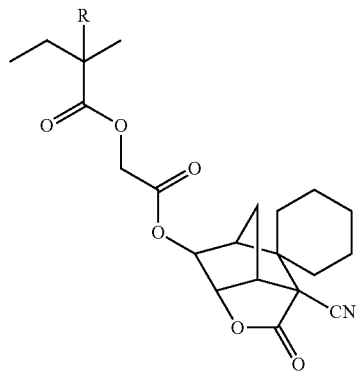
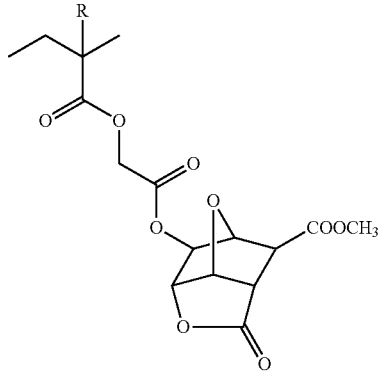
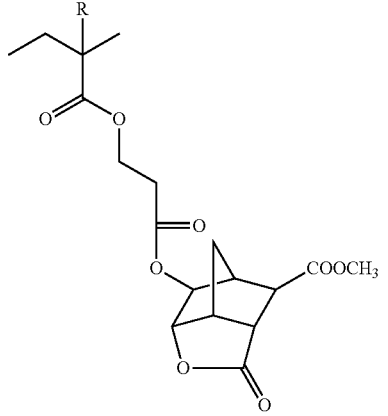
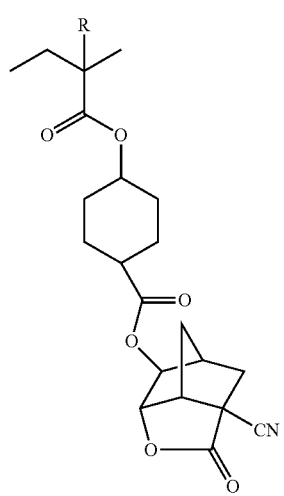

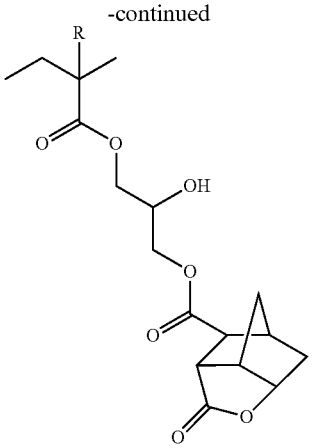

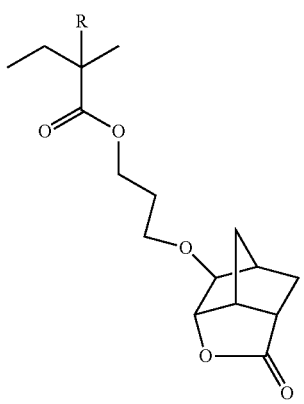

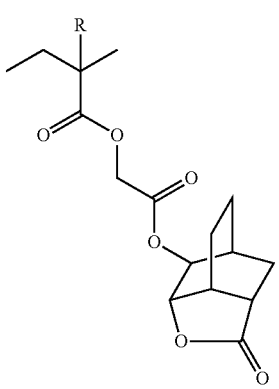

It is preferred for the alicyclic hydrocarbon based acid-decomposable resin to have a repeating unit having an alicyclic hydrocarbon structure substituted with a polar group. The containment of this repeating unit would realize enhancements of adhesion to substrate and developer affinity. The polar group is preferably a hydroxyl group or a cyano group. The hydroxyl group as the polar group constitutes an alcoholic hydroxyl group.

As the alicyclic hydrocarbon structure substituted with a polar group, there can be mentioned, for example, any of the structures of general formulae (VIIa) and (VIIb) below.

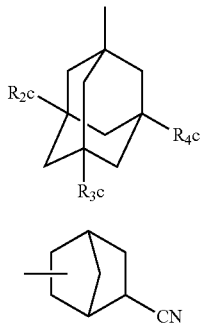

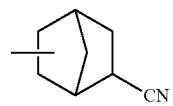

In the general formula (VIIa), each of $R_2c$ to $R_4c$ independently represents a hydrogen atom, a hydroxyl group or a cyano group, provided that at least one of the $R_2c$ to $R_4c$ represents a hydroxyl group or a cyano group. Preferably, one or two of the $R_2c$ to $R_4c$ are hydroxyl groups and the remainder is a hydrogen atom. More preferably, two of the $R_2c$ to $R_4c$ are hydroxyl groups and the remainder is a hydrogen atom.

The groups of the general formula (VIIa) preferably have a dihydroxy form or monohydroxy form, more preferably a dihydroxy form.

As the repeating units having the groups of the general formula (VIIa) or (VIIb), there can be mentioned the repeating units of the general formulae (II-AB1) and (II-AB2) wherein at least one of R13' to R16' has any of the groups of the general formula (VIIa) or (VIIb) as well as the repeating units of general formula (AIIa) or (AIIb) below. Examples of the former include a structure in which the $R_5$ of —COOR$_5$ represents any of the groups of the general formula (VIIa) or (VIIb).

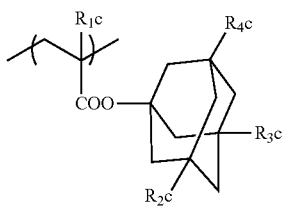

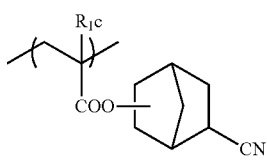

In the general formulae (AIIa) and (AIIb), $R_1c$ represents a hydrogen atom, a methyl group, a trifluoromethyl group or a hydroxymethyl group.

$R_2c$ to $R_4c$ have the same meaning as those of the general formula (VIIa).

Specific examples of the repeating units represented by the general formula (AIIa) or (AIIb) will be shown below, which however in no way limit the scope of the present invention.

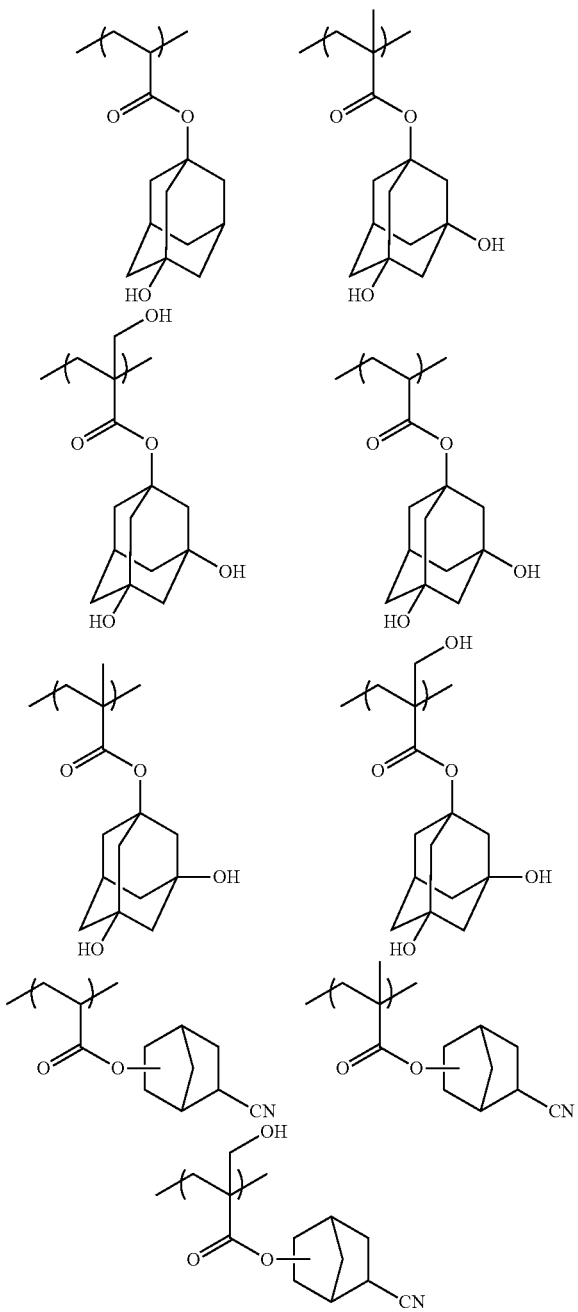

The alicyclic hydrocarbon based acid-decomposable resin according to the present invention may have any of the repeating units of general formula (VIII) below.

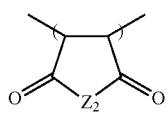

(VIII)

In the general formula (VIII), $Z_2$ represents —O— or —N($R_{41}$)—. $R_{41}$ represents a hydrogen atom, a hydroxyl group, an alkyl group or —OSO$_2$—$R_{42}$. $R_{42}$ represents an alkyl group, a cycloalkyl group or a camphor residue. The alkyl groups represented by $R_{41}$ and $R_{42}$ may be substituted with, for example, a halogen atom. As the halogen atom, a fluorine atom is preferable.

Specific examples of the repeating units of the general formula (VIII) will be shown below, which however in no way limit the scope of the present invention.

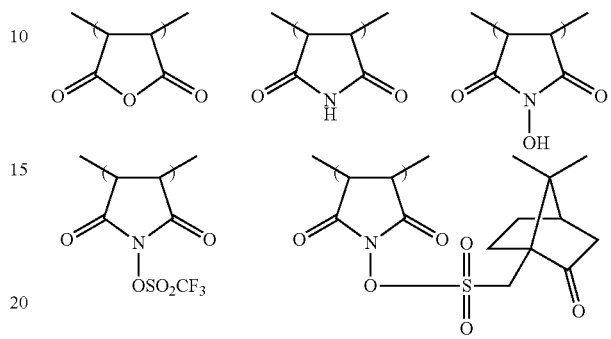

It is preferred for the alicyclic hydrocarbon based acid-decomposable resin to contain a repeating unit having an alkali-soluble group, especially a repeating unit having a carboxyl group. The introduction of the repeating unit having an alkali-soluble group would increase the resolving power in contact hole usage.

The repeating unit having a carboxyl group is preferably either a repeating unit wherein the carboxyl group is directly bonded to the principal chain of a resin or a repeating unit wherein the carboxyl group is bonded via a connecting group to the principal chain of a resin.

Examples of the former case include a repeating unit formed by acrylic acid or methacrylic acid. In the latter case, the connecting group may have a cyclohydrocarbon structure of a single ring or multiple rings.

As the repeating units having a carboxyl group, those formed by acrylic acid or methacrylic acid is most preferred.

The weight average molecular weight (Mw) of the resin that is decomposed to thereby increase its solubility in an alkaline developer when acted on by an acid is in the range of 2000 to 200,000. By making Mw higher than 2,000, the heat resistance and dry etching resistance can be enhanced. By making Mw lower than 200,000, developability can be enhanced, and the viscosity of the composition can be decreased leading to better film forming property.

More preferable Mw falls in between 2,500 to 50,000, and further more preferable Mw in between 3,000 to 25,000. In cases for pattern formation using an electron beam, X-ray, or high-energy beam whose wavelength is 50 nm or lower (for example, EUV), it is particularly preferable for Mw to fall within the range of 3,000 to 10,000. By adjusting the Mw, increase in the heat resistance, enhancement of the resolving power, and decrease of the development defect can simultaneously be realized.

The dispersity (Mw/Mn) of the resin is preferably in the range of 1.0 to 3.0, more preferably 1.2 to 2.5, and further preferably 1.2 to 1.6. By adjusting the dispersity, for example, line edge roughness characteristics can be enhanced.

The content of the resin is preferably in the range of 0 to 99.9 mass %, more preferably 50 to 95 mass %, and further preferably 60 to 93 mass % based on the total solids of the composition.

[4] Resin Soluble in an Alkaline Developer (Hereinafter, Also Referred to as Alkali-Soluble Resin)

The alkali dissolution rate of the alkali-soluble resin as measured in a 0.261 N tetramethylammonium hydroxide (TMAH) (23° C.) is preferably 2 nm/sec or higher, especially preferably 20 nm/sec or higher.

As the alkali-soluble resin for use in the present invention, there can be mentioned, for example, a novolak resin, a hydrogenated novolak resin, an acetone-pyrogallol resin, an o-polyhydroxystyrene, a m-polyhydroxystyrene, a p-polyhydroxystyrene, a hydrogenated polyhydroxystyrene, a halogenated or alkylated polyhydroxystyrene, a hydroxystyrene-N-substituted maleimide copolymer, an o/p- and m/p-hydroxystyrene copolymer, a partial O-alkylation product of hydroxyl of polyhydroxystyrene (for example, a 5 to 30 mol % O-methylation product, O-(1-methoxy)ethylation product, O-(1-ethoxy)ethylation product, O-2-tetrahydropyranylation product, O-(t-butoxycarbonyl)methylation product, etc.), an O-acylation product thereof (for example, a 5 to 30 mol % O-acetylation product, O-(t-butoxy)carbonylation product, etc.), a styrene-maleic anhydride copolymer, styrene-hydroxystyrene copolymer, an α-methylstyrene-hydroxystyrene copolymer, a carboxylated methacrylic resin or its derivative, or a polyvinyl alcohol derivative. However, the alkali-soluble resins are not limited to these.

Especially preferred alkali-soluble resins are a novolak resin, an o-polyhydroxystyrene, a m-polyhydroxystyrene, a p-polyhydroxystyrene, a copolymer of these polyhydroxystyrenes, an alkylated polyhydroxystyrene, a partial O-alkylation product or O-acylation product of polyhydroxystyrene, a styrene-hydroxystyrene copolymer and an α-methylstyrene-hydroxystyrene copolymer.

The resins containing one or more hydroxystyrene structures are particularly preferred. Of these, those containing one or more m-hydroxystyrene structures are especially preferred.

The above novolak resin can be obtained by addition condensation of a given monomer as a main component with an aldehyde conducted in the presence of an acid catalyst.

The weight average molecular weight of the alkali-soluble resin is 2000 or greater, preferably from 5000 to 200,000 and more preferably 5000 to 100,000. Herein, the weight average molecular weight is in terms of polystyrene molecular weight measured by gel permeation chromatography.

The alkali-soluble resins can be used individually or in combination.

The amount of alkali-soluble resin added, based on the solid contents of the whole composition, is preferably in the range of 40 to 97 mass %, and more preferably in the range of 60 to 90 mass %.

[5] Compound that is Decomposed to Thereby Increase its Solubility in an Alkaline Developer when Acted on by an Acid Having the Molecular Weight of 300 or More (Hereinafter, Also Referred to as Dissolution-Inhibiting Compound)

From the viewpoint of preventing any lowering of 220 nm or shorter transmission, the dissolution inhibiting compound is preferably an alicyclic or aliphatic compound containing an acid-decomposable group. As such, for example, cholic acid derivatives having an acid-decomposable group described in Proceeding of SPIE, 2724, 355 (1996) can be exemplified. The acid-decomposable group and alicyclic structure are the same as described above with respect to the alicyclic hydrocarbon based acid-decomposable resin.

When the composition according to the present invention is exposed to a KrF excimer laser or irradiated with electron beams, preferred use is made of a compound containing a structure resulting from substitution of the phenolic hydroxyl group of a phenol compound with an acid-decomposable group. The phenol compound preferably contains 1 to 9 phenol skeletons, more preferably 2 to 6 phenol skeletons.

Molecular weight of the dissolution-inhibiting compound is 3000 or less. The molecular weight is preferably in the range of 300 to 3000, and more preferably in the range of 500 to 2500.

The amount of dissolution inhibiting compound added is preferably in the range of 3 to 50 mass %, more preferably 5 to 40 mass % based on the solid contents of the composition.

Specific examples of the dissolution inhibiting compounds will be shown below, which however in no way limit the scope of the present invention.

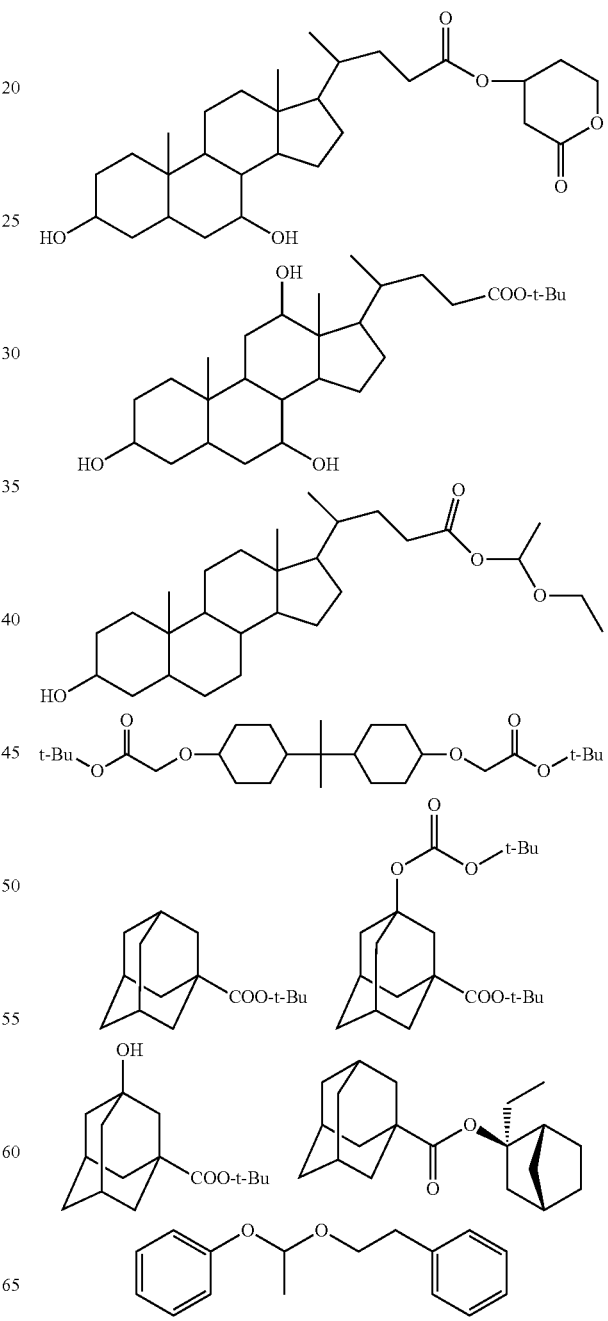

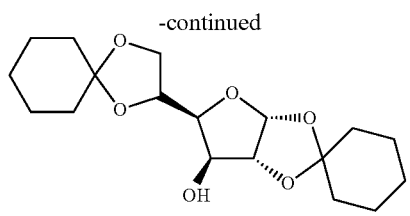

[6] Acid Crosslinking Agent Capable of Crosslinking with the Resin Under the Action of an Acid Any crosslinking agent can be used as long as it is a compound capable of crosslinking with the resin soluble in an alkaline developer by the action of an acid. However, compounds (1) to (3) below are preferred. Phenol derivative having alkoxymethyl group is especially preferred from the viewpoint of the sensitivity and the preservation stability.

(1) A hydroxymethylated form, alkoxymethylated or acyloxymethylated form of phenol derivative.

(2) A compound having an N-hydroxymethyl group, an N-alkoxymethyl group or an N-acyloxymethyl group.

(3) A compound having an epoxy group.

Especially, the acid crosslinking agent is preferably a compound having two or more hydroxymethyl groups or alkoxymethyl groups in the molecule.

The alkoxymethyl group preferably has 6 or less carbon atoms, and the acyloxymethyl group preferably has 6 or less carbon atoms.

Those especially preferred among these crosslinking agents will be shown below.

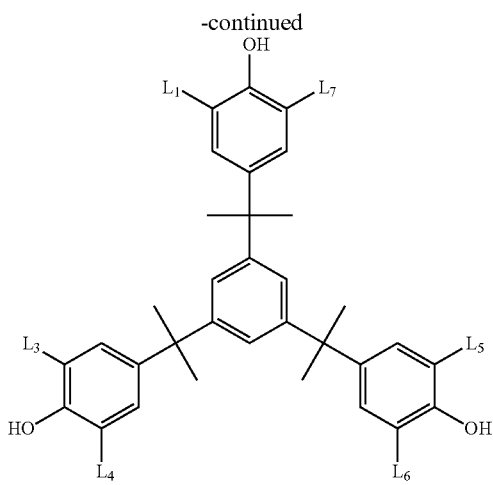

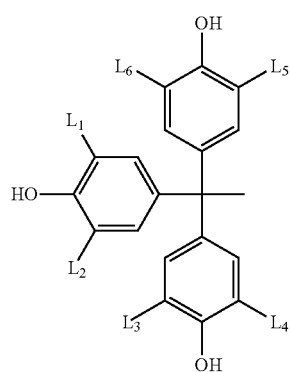

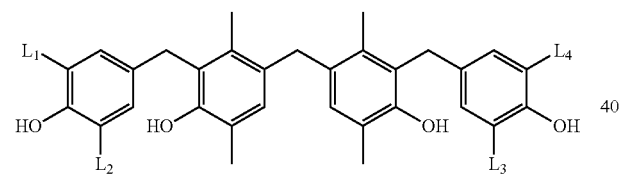

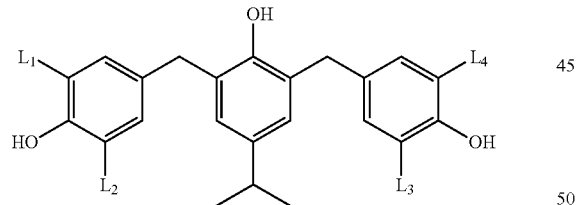

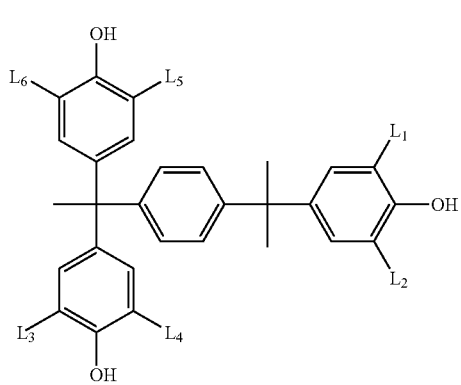

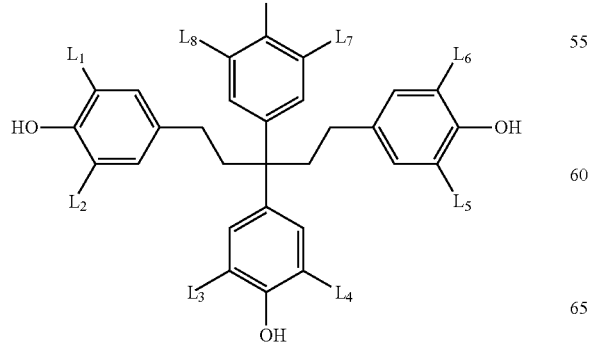

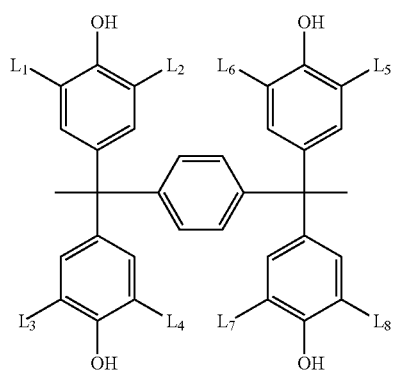

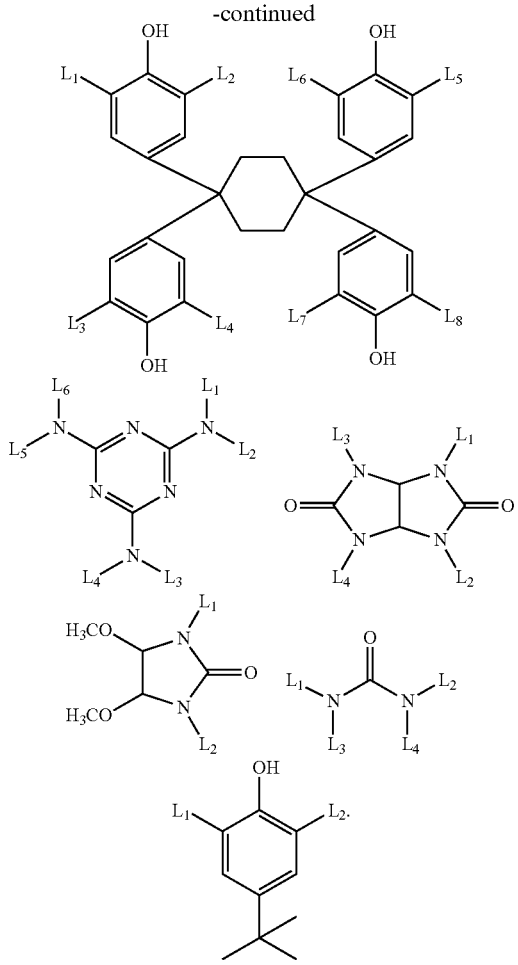

In the formulae, $L_1$ to $L_8$ may be identical to or different from each other, and each thereof represents a hydrogen atom, a hydroxymethyl group, a methoxymethyl group, an ethoxymethyl group or an alkyl group having 1 to 6 carbon atoms.

The crosslinking agent is generally added in an amount of 3 to 70 mass %, preferably 5 to 50 mass %, based on the solid content of the composition.

[7] Basic Compound

The composition of the present invention preferably contains a basic compound in order to reduce any performance change over time from exposure to bake. The role of the basic compound is to quench any deprotection reaction by the acid generated by exposure, and the diffusivity and basicity thereof would influence the substantial diffusivity of the acid.

As preferred structures, there can be mentioned an ammonium compound of formula (A) and basic compounds with the structures of formulae (B) to (E) below and ammonium salts.

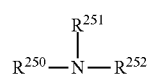 (A)

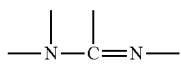 (B)

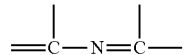 (C)

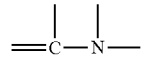 (D)

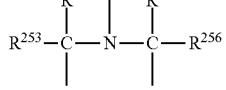 (E)

In the formula (A), each of $R^{250}$, $R^{251}$ and $R^{252}$ independently represents a hydrogen atom, an alkyl group (preferably having 1 to 20 carbon atoms), a cycloalkyl group (preferably having 3 to 20 carbon atoms) or an aryl group (preferably having 6 to 20 carbon atoms). $R^{250}$ and $R^{251}$ may be bonded to each other to thereby form a ring. These groups may contain one or more substituents.

The alkyl group and cycloalkyl group having substituents are preferably an aminoalkyl group having 1 to 20 carbon atoms, an aminocycloalkyl group having 3 to 20 carbon atoms, a hydroxyalkyl group having 1 to 20 carbon atoms and a hydroxycycloalkyl group having 3 to 20 carbon atoms.

These groups may contain an oxygen atom, a sulfur atom or a nitrogen atom in the alkyl chain thereof.

In the formula (E), each of $R^{253}$, $R^{254}$, $R^{255}$ and $R^{256}$ independently represents an alkyl group (preferably having 1 to 6 carbon atoms) or a cycloalkyl group (preferably having 3 to 6 carbon atoms). These groups may contain one or more substituents.

As preferred compounds, there can be mentioned guanidine, aminopyrrolidine, pyrazole, pyrazoline, piperazine, aminomorpholine, aminoalkylmorpholines, piperidine and the like. These may have substituents.

As further preferred compounds, there can be mentioned compounds with an imidazole structure, a diazabicyclo structure, an onium hydroxide structure, an onium carboxylate structure, a trialkylamine structure, an aniline structure or a pyridine structure, alkylamine derivatives having a hydroxyl group and/or an ether bond, aniline derivatives having a hydroxyl group and/or an ether bond and the like.

As the compounds with an imidazole structure, there can be mentioned imidazole, 2,4,5-triphenylimidazole, benzimidazole and the like.

As the compounds with a diazabicyclo structure, there can be mentioned 1,4-diazabicyclo[2,2,2]octane, 1,5-diazabicyclo[4,3,0]non-5-ene, 1,8-diazabicyclo[5,4,0]undec-7-ene and the like.

As the compounds with an onium hydroxide structure, there can be mentioned triarylsulfonium hydroxides, phenacylsulfonium hydroxide, and sulfonium hydroxides having a 2-oxoalkyl group such as triphenylsulfonium hydroxide, tris(t-butylphenyl)sulfonium hydroxide, bis(t-butylphenyl)iodonium hydroxide, phenacylthiophenium hydroxide, 2-oxopropylthiophenium hydroxide and the like.

As the compounds with an onium carboxylate structure, there can be mentioned those having a carboxylate at the anion moiety of the compounds with an onium hydroxide structure, for example, acetate, adamantane-1-carboxylate, perfluoroalkyl carboxylates and the like.

As the compounds with a trialkylamine structure, there can be mentioned tri(n-butyl)amine, tri(n-octyl)amine and the like.

As the aniline compounds, there can be mentioned 2,6-diisopropylaniline, N,N-dimethylaniline and the like.

As the alkylamine derivatives having a hydroxyl group and/or an ether bond, there can be mentioned ethanolamine, diethanolamine, triethanolamine, tris(methoxyethoxyethyl) amine and the like.

As the aniline derivatives having a hydroxyl group and/or an ether bond, there can be mentioned N,N-bis(hydroxyethyl) aniline and the like.

Further, as basic compounds, there can be mentioned at least one nitrogenous compound selected from among an amine compound having a phenoxy group, and an ammonium salt compound having a phenoxy group.

As the amine compound, use can be made of primary, secondary and tertiary amine compounds. An amine compound having at least one alkyl group bonded to the nitrogen atom thereof is preferred. Among the amine compounds, a tertiary amine compound is more preferred. In the amine compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom.

In the amine compounds, it is preferred for the alkyl chain thereof to contain an oxygen atom, thereby forming an oxyalkylene group. The number of oxyalkylene groups in each molecule is one or more, preferably 3 to 9, and more preferably 4 to 6. The oxyalkylene group is preferably an oxyethylene group (—CH$_2$CH$_2$O—) or an oxypropylene group (—CH(CH$_3$)CH$_2$O— or —CH$_2$CH$_2$CH$_2$O—), more preferably an oxyethylene group.

In the ammonium salt compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom.

In the ammonium salt compounds, it is preferred for the alkyl chain thereof to contain an oxygen atom, thereby forming an oxyalkylene group. The number of oxyalkylene groups in each molecule is one or more, preferably 3 to 9 and more preferably 4 to 6. The oxyalkylene group is preferably an oxyethylene group (—CH$_2$CH$_2$O—) or an oxypropylene group (—CH(CH$_3$)CH$_2$O— or —CH$_2$CH$_2$CH$_2$O—), more preferably an oxyethylene group.

As the anion of the ammonium salt compounds, there can be mentioned a halide, a sulfonate, a borate, a phosphate, a hydroxide or the like. Of these, a hydroxide is preferred.

Among halides, a chloride, a bromide and an iodide are especially preferred.

The amine compound having a phenoxy group can be obtained by first heating a primary or secondary amine having a phenoxy group and a haloalkyl ether so as to effect a reaction therebetween, subsequently adding an aqueous solution of a strong base, such as sodium hydroxide, potassium hydroxide or a tetraalkylammonium, and thereafter carrying out an extraction with an organic solvent, such as ethyl acetate or chloroform. Alternatively, the amine compound having a phenoxy group can be obtained by first heating a primary or secondary amine and a haloalkyl ether having a phenoxy group at its terminus so as to effect a reaction therebetween, subsequently adding an aqueous solution of a strong base, such as sodium hydroxide, potassium hydroxide or a tetraalkylammonium, and thereafter carrying out an extraction with an organic solvent, such as ethyl acetate or chloroform.

From the viewpoint of sensitivity, roughness and stability, an ammonium salt compound is preferred among the various basic compounds. A quaternary ammonium salt compound in its hydroxide form is most preferred.

These basic compounds may be used either individually or in combination.

The molecular weight of the basic compounds is preferably in the range of 250 to 1000, more preferably 250 to 800 and further preferably 400 to 800.

The amount of basic compound contained in the composition, based on the total solid content of the composition, is preferably in the range of 1.0 to 8.0 mass %, more preferably 1.5 to 5.0 mass % and further preferably 2.0 to 4.0 mass %.

[8] Fluorinated and/or Siliconized Surfactant

The composition according to the present invention may further contain one or more fluorinated and/or siliconized surfactants. As the fluorinated and/or siliconized surfactant, a fluorinated surfactant, a siliconized surfactant, a surfactant containing both fluorine and silicon atoms, and a mixture thereof can be exemplified.

The composition according to the present invention when containing the fluorinated and/or siliconized surfactant would, in the use of an exposure light source of 250 nm or below, especially 220 nm or below, realize favorable sensitivity and resolving power and produce a resist pattern of less adhesion and development defects.

As useful commercially available surfactants, there can be mentioned, for example, fluorinated or siliconized surfactants, such as Eftop EF301 and EF303 (produced by Shin-Akita Kasei Co., Ltd.), Florad FC 430 and 431 (produced by Sumitomo 3M Ltd.), Megafac F171, F173, F176, F189 and R08 (produced by Dainippon Ink Chemicals, Inc.), Surflon S-382, SC101, 102, 103, 104, 105 and 106 (produced by Asahi Glass Co., Ltd.) and Troy Sol S-366 (produced by Troy Chemical Co., Ltd.). Further, polysiloxane polymer KP-341 (produced by Shin-Etsu Chemical Co., Ltd.) can be employed as the siliconized surfactant.

As the surfactants, besides the above publicly known surfactants, use can be made of a surfactant based on a polymer having a fluorinated aliphatic group derived from a fluorinated aliphatic compound produced by a telomerization technique (also called a telomer process) or an oligomerization technique (also called an oligomer process). The fluorinated aliphatic compound can be synthesized by the process described in JP-A-2002-90991.

The polymer having a fluorinated aliphatic group is preferably a copolymer from a monomer having a fluorinated aliphatic group and a poly(oxyalkylene) acrylate and/or poly (oxyalkylene) methacrylate, which copolymer may have an irregular distribution or may result from block copolymerization.

As the poly(oxyalkylene) group, there can be mentioned a poly(oxyethylene) group, a poly(oxypropylene) group, a poly (oxybutylene) group or the like. Further, use can be made of a unit having alkylene groups of different chain lengths in a single chain, such as poly(oxyethylene-oxypropylene oxyethylene block concatenation) or poly(oxyethylene-oxypropylene block concatenation).

Moreover, the copolymer from a monomer having a fluorinated aliphatic group and a poly(oxyalkylene) acrylate (or methacrylate) is not limited to two-monomer copolymers and may be a three or more monomer copolymer obtained by simultaneous copolymerization of two or more different monomers having a fluorinated aliphatic group, two or more different poly(oxyalkylene) acrylates (or methacrylates), etc.

For example, as a commercially available surfactant, there can be mentioned Megafac F178, F-470, F-473, F-475, F-476 or F-472 (produced by Dainippon Ink & Chemicals, Inc.). Further, there can be mentioned a copolymer from an acrylate (or methacrylate) having a $C_6F_{13}$ group and a poly(oxyalkylene) acrylate (or methacrylate), a copolymer from an acrylate (or methacrylate) having a $C_6F_{13}$ group, poly(oxyethylene) acrylate (or methacrylate) and poly(oxypropylene) acrylate (or methacrylate), a copolymer from an acrylate (or methacrylate) having a $C_8F_{17}$ group and a poly(oxyalkylene) acrylate (or methacrylate), a copolymer from an acrylate (or methacrylate) having a $C_8F_{17}$ group, poly(oxyethylene) acrylate (or methacrylate) and poly(oxypropylene) acrylate (or methacrylate), or the like.

The amount of fluorinated and/or siliconized surfactant used is preferably in the range of 0.0001 to 2 mass %, more preferably 0.001 to 1 mass % based on the total solids of the composition.

[9] Organic Solvent

The composition according to the present invention in its typical form further contains a specified organic solvent capable of dissolving the above components.

As useful organic solvents, there can be mentioned, for example, ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone and tetrahydrofuran.

The solvents having a ketone structure include a linear ketone solvent and a cycloketone solvent. Compounds having 5 to 8 carbon atoms in total are preferred from the viewpoint of high coatability.

As the linear ketone solvent, there can be mentioned, for example, 2-heptanone, methyl ethyl ketone or methyl isobutyl ketone. Of these, 2-heptanone is most preferred.

As the cycloketone solvent, there can be mentioned, for example, cyclopentanone, 3-methyl-2-cyclopentanone, cyclohexanone, 2-methylcyclohexanone, 2,6-dimethylcyclohexanone, cycloheptanone, cyclooctanone or isophorone. Of these, cyclohexanone and cycloheptanone are most preferred.

As the organic solvent, it is preferred to use either, a single solvent having a ketone structure alone or a mixed solvent consisting of a solvent having a ketone structure and another solvent.

As another solvent to be mixed with the solvent having a ketone structure (joint solvent), there can be mentioned, for example, a propylene glycol monoalkyl ether carboxylate, an alkyl lactate, a propylene glycol monoalkyl ether, an alkyl alkoxypropionate or a lactone compound.

As the propylene glycol monoalkyl ether carboxylate, there can be mentioned, for example, propylene glycol monomethyl ether acetate, propylene glycol monomethyl ether propionate or propylene glycol monoethyl ether acetate.

As the alkyl lactate, there can be mentioned, for example, methyl lactate or ethyl lactate.

As the propylene glycol monoalkyl ether, there can be mentioned, for example, propylene glycol monomethyl ether or propylene glycol monoethyl ether.

As the alkyl alkoxypropionate, there can be mentioned, for example, methyl methoxypropionate, ethyl methoxypropionate, methyl ethoxypropionate or ethyl ethoxypropionate.

As the lactone compound, there can be mentioned, for example, γ-butyrolactone.

As preferred joint solvents, there can be mentioned a propylene glycol monoalkyl ether carboxylate, an alkyl lactate and a propylene glycol monoalkyl ether. A more preferred joint solvent is propylene glycol monomethyl ether acetate.

A solvent with a boiling point as high as 200° C. or above, such as ethylene carbonate or propylene carbonate, may be mixed into the solvent for use from the viewpoint of film thickness uniformity and development defect performance.

The amount of high-boiling-point solvent added, based on the total mass of solvents, is generally in the range of 0.1 to 15 mass %, preferably 0.5 to 10 mass % and more preferably 1 to 5 mass %.

In the present invention, an actinic ray- or radiation-sensitive resin composition is prepared using an organic solvent, preferably a mixed solvent consisting of two or more types of solvents.

The solid content of the composition is generally in the range of 1 to 25 mass %, preferably 2 to 20 mass % and more preferably 2.5 to 10 mass %. In particular, when the pattern formation is carried out using electron beams, EUV light or ArF light, it is preferred for the solid content to fall within the range of 2.5 to 4.5 mass %.

[10] Other Additives

The composition according to the present invention may further contain other additives, such as a dye, a plasticizer, a surfactant other than the above mentioned fluorized and/or siliconized surfactants, a photosensitizer, and a compound capable of increasing the solubility in a developer.

The compound capable of increasing the solubility in a developer (dissolution accelerating compound) is, for example, a low-molecular compound of 1000 or less molecular weight having two or more phenolic OH groups or one or more carboxyl groups. When a carboxyl group is contained, an alicyclic or aliphatic compound is preferred.

The amount of dissolution accelerating compound added, based on the mass of the resin, is preferably in the range of 2 to 50 mass %, more preferably 5 to 30 mass %. It is preferred for the amount to be up to 50 mass % from the viewpoint of suppression of any development residue and prevention of any pattern distortion at development.

The above phenolic compound of 1000 or less molecular weight can be easily synthesized by persons of ordinary skill in the art to which the present invention pertains while consulting the processes described in, for example, JP-A's 4-122938 and 2-28531, U.S. Pat. No. 4,916,210 and EP 219294.

As the carboxylated alicyclic or aliphatic compound, there can be mentioned, for example, a carboxylic acid derivative of steroid structure such as cholic acid, deoxycholic acid or lithocholic acid, an adamantanecarboxylic acid derivative, adamantanedicarboxylic acid, cyclohexanecarboxylic acid, cyclohexanedicarboxylic acid or the like. These are however nonlimiting.

Surfactants other than the above fluorinated and/or siliconized surfactants, there can be mentioned nonionic surfactants, such as a polyoxyethylene alkyl ether, a polyoxyethylene alkylallyl ether, a polyoxyethylene-polyoxypropylene block copolymer, a sorbitan aliphatic ester, a polyoxyethylene sorbitan aliphatic ester or the like. These surfactants may be added either individually or in combination.

[11] Method of Forming Pattern

The method of forming a pattern using the composition according to the present invention will be described below.

The composition according to the present invention is typically used in such a manner that the components are dissolved in a given organic solvent, preferably the above mixed solvent, and applied onto a given support. For example, the composition is applied to a substrate (e.g., silicon, silicon/silicon dioxide coating, silicon nitride, quartz with a Cr layer, or the like) for use in the production of precision integrated circuit elements, imprint mold structures, etc. by appropriate application means, such as a spinner or a coater. The thus applied composition is dried, thereby obtain an actinic ray- or radiation-sensitive film (hereinafter also referred to as a photosensitive film). The drying temperature is preferably in the range of 60 to 150° C., more preferably 80 to 130° C. In advance, the substrate may be provided with an antireflection film known in the art.

Subsequently, the photosensitive film is exposed to actinic rays or radiation, preferably baked (heated), and developed. It is preferred for the baking temperature to range from 80 to 150° C., especially from 90 to 130° C. from the viewpoint of sensitivity and stability. Accordingly, a desirable pattern can be obtained.

As the actinic rays or radiation, there can be mentioned, for example, infrared radiation, visible light, ultraviolet radiation, far ultraviolet radiation, X-rays or electron beams. As the actinic rays or radiation, preferred use is made of one with, for example, 250 nm or less, especially 220 nm or less wavelength. As the actinic rays or radiation, there can be mentioned, for example, a KrF excimer laser (248 nm), an ArF excimer laser (193 nm), an $F_2$ excimer laser (157 nm), X-rays or electron beams. As especially preferred actinic rays or radiation, there can be mentioned an ArF excimer laser, an $F_2$ excimer laser, EUV (13 nm) or electron beams.

In the stage of irradiation with actinic rays or radiation, exposure (liquid immersion exposure) may be carried out after filling the interstice between the photosensitive film and a lens with a liquid of refractive index higher than that of air. This would realize an enhancement of resolving power. For the prevention of direct contact of the resist film with the liquid for liquid immersion, a film that is highly insoluble in the liquid for liquid immersion (hereinafter also referred to as a "top coat") may be provided between the resist film formed by the composition of the present invention and the liquid for liquid immersion. As other means to prevent the contact between the resist film and the liquid for liquid immersion, a hydrophobic resin (HR) may be added to the composition. As the hydrophobic resin, in addition to those described above, the resins explained in paragraph 0172-0253 in US 2008/0305432 A1 can also be exemplified.

In the development step, an alkaline developer is generally used.

As the alkaline developer, use can be made of any of alkaline aqueous solutions containing, for example, an inorganic alkali compound such as sodium hydroxide, potassium hydroxide, sodium carbonate, sodium silicate, sodium metasilicate or aqueous ammonia; a primary amine such as ethylamine or n-propylamine; a secondary amine such as diethylamine or di-n-butylamine; a tertiary amine such as triethylamine or methyldiethylamine; an alcoholamine such as dimethylethanolamine or triethanolamine; a quaternary ammonium salt such as tetramethylammonium hydroxide or tetraethylammonium hydroxide; or a cycloamine such as pyrrole or piperidine.

Appropriate amounts of an alcohol and/or a surfactant may be added to the alkaline developer.

The concentration of alkaline developer is generally in the range of 0.1 to 20 mass %. The pH value of the alkaline developer is generally in the range of 10.0 to 15.0.

With respect to the particulars of the process for fabricating an imprint mold using the composition according to the present invention, reference can be made to, for example, Japanese Patent No. 4109085, JP-A-2008-162101, "Fundamentals of nanoimprint and its technology development/application deployment—technology of nanoimprint substrate and its latest technology deployment" edited by Yoshihiko Hirai, published by Frontier Publishing, etc.

The thickness of a resist film is preferably 50 nm to 200 nm, more preferably 60 nm to 150 nm from the view point of the resolution.

EXAMPLE

The present invention will be described in greater detail below by way of its examples. However, the gist of the present invention is in no way limited to these examples.

<Sulfonic Acid-Generating Compound>

[Synthesis]

Compounds 1 to 16 shown in Table 1 below were synthesized as sulfonic acid-generating compounds in the following manner. Further, for control, comparative compounds 1 to 5 were synthesized in the following manner.

TABLE 1

| Compd. | Structure of compd. | Vol. of generated acid (Å³) |
|---|---|---|
| 1 | | 303 |
| 2 | | 437 |

TABLE 1-continued

| Compd. | Structure of compd. | Vol. of generated acid (Å³) |
|---|---|---|
| 3 | | 244 |
| 4 | | 266 |
| 5 | | 380 |
| 6 | | 311 |
| 7 | | 244 |
| 8 | | 271 |

TABLE 1-continued

| Compd. | Structure of compd. | Vol. of generated acid (Å³) |
|---|---|---|
| 9 | | 303 |
| 10 | | 303 |
| 11 | | 303 |
| 12 | | 303 |
| 13 | | 303 |

TABLE 1-continued

| Compd. | Structure of compd. | Vol. of generated acid (Å$^3$) |
|---|---|---|
| 14 | | 303 |
| 15 | | 303 |
| 16 | | 303 |
| Comparative compound 1 | | 186 |
| Comparative compound 2 | | 216 |
| Comparative compound 3 | | 186 |

TABLE 1-continued

| Compd. | Structure of compd. | Vol. of generated acid (Å³) |
|---|---|---|
| Comparative compound 4 | | 186 |
| Comparative compound 5 | | 172 |

(Synthesis of Compound 1)

Alcohol of the formula below (3.9 g, 20.1 mmol), 30 ml of methylene chloride and triethylamine (7.8 g, 77.5 mmol) were mixed together.

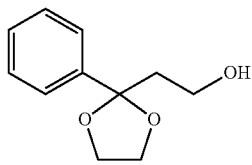 [SMILES: OCCC1(c2ccccc2)OCCO1]

Subsequently, triisopropylbenzenesulfonyl chloride (6.1 g, 20.2 mmol) and dimethylaminopyridine (98.1 g, 0.8 mmol) were added to the obtained mixed solution, and agitated at room temperature for two hours. Then, 50 ml of water was added, and the resultant organic phase was extracted with 100 ml of ethyl acetate. The organic phase was washed with 50 ml of water three times. Further, the organic phase was washed with 50 ml of a saturated aqueous solution of sodium hydrogen carbonate and 50 ml of a saturated aqueous solution of sodium chloride, dried over magnesium sulfate and distilled in vacuum. The thus obtained crystal was recrystallized from isopropyl alcohol, thereby obtaining 3.0 g of compound 1.

$^1$H-NMR (400 MHz, CDCl$_3$): δ1.22-1.26 (m, 18H), 2.32 (t, 2H, J=8.0 Hz), 2.90 (m, 1H), 3.73 (t, 2H, J=6.8 Hz), 3.96 (t, 2H, J=6.8 Hz), 4.12 (m, 2H), 4.18 (t, 2H, J=8.0 Hz), 7.16 (s, 2H), 7.30-7.40 (m, 5H)

(Synthesis of Compounds 2 to 13 and 16)

Compounds 2 to 13 and 16 were synthesized in the same manner as mentioned above with respect to compound 1. Namely, these compounds were synthesized by reacting corresponding alcohols with a sulfonic acid halide in basic condition.

(Synthesis of Compound 14)

First, 10 g of 3-methyl-1,3-butanediol was dissolved in 200 ml of acetonitrile. Then, 14.6 g of triethylamine and 235 mg of 4-dimethylaminopyridine were added to the solution. Thereafter, 29.1 g of 2,4,6-triisopropylbenzenesulfonyl chloride was added, and agitated at room temperature for four hours. The reaction liquid was loaded with 100 ml of ethyl acetate and 100 ml of distilled water, and transferred to a separatory funnel. The water layer was removed. Thereafter, the organic phase was washed with 200 ml of distilled water three times, and concentrated. The concentrate was purified by silica gel column chromatography (developing solvent: 10/1 ethyl acetate/hexane). The solvent was distilled off in vacuum, and the product was dried in vacuum, thereby obtaining 30.7 g of compound 14.

$^1$H-NMR (CDCl$_3$: ppm) δ: 1.33-1.22 (24H, m), 1.92 (2H, t, J=7.2 Hz), 2.97-2.85 (1H, m), 4.20-4.10 (2H, m), 4.23 (2H, t, J=7.2 Hz), 7.18 (2H, s)

(Synthesis of Compound 15)

First, 2.95 g of 3,3-dimethoxy-3-phenylpropan-1-ol was dissolved in 100 ml of acetonitrile. Then, 5.87 g of triethylamine and 74 mg of 4-dimethylaminopyridine were added to the solution. Thereafter, 4.56 g of 2,4,6-triisopropylbenzenesulfonyl chloride was added, and agitated at room temperature for four hours. The reaction liquid was loaded with 100 ml of ethyl acetate and 100 ml of distilled water, and transferred to a separatory funnel. The water layer was removed. Thereafter, the organic phase was washed with 200 ml of distilled water three times, and concentrated. The concentrate was purified by silica gel column chromatography (developing solvent: 10/1 ethyl acetate/hexane). The solvent was distilled off in vacuum, and the product was dried in vacuum, thereby obtaining 5.67 g of compound 15.

$^1$H-NMR (CDCl$_3$: ppm) δ: 1.27~1.18 (18H, m), 2.33 (2H, t, J=8.0 Hz), 2.92-2.85 (1H, m), 3.11 (6H, s), 3.72 (2H, t, J=8.0 Hz), 4.07-3.99 (2H, m), 7.12 (2H, 1H), 7.36-7.29 (5H, m)

[Calculation of Volume of Acid]

The volume of sulfonic acid that can be generated by each of the above compounds 1 to 16 and comparative compounds 1 to 5 was calculated in the following manner. Namely, the volume was determined by means of the software "WinMO-PAC" compiled by Fujitsu Limited in the following manner. First, the chemical structure of the acid generated by each of the compounds was inputted. Subsequently, while regarding this structure as an initial structure, the most stable conformation of the acid was determined by a molecular force field calculation using an MM3 method. Thereafter, a molecular orbital calculation using a PM3 method was carried out with respect to the most stable conformation. Thus, the "accessible volume" of each of the acids was determined.

The results are indicated in Table 1 above. As apparent from the results, the volume of sulfonic acid generated by each of the compounds 1 to 16 was greater than 240 Å$^3$. In contrast, the volume of sulfonic acid generated by each of the comparative compounds 1 to 5 was less than 240 Å$^3$.

<Photoacid Generator>

The following compounds A to G were used as photoacid generators.

A
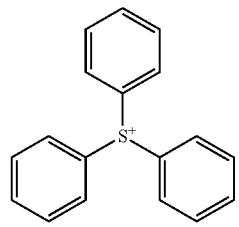 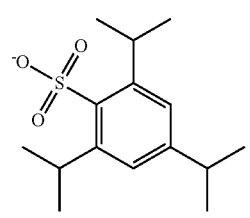

B
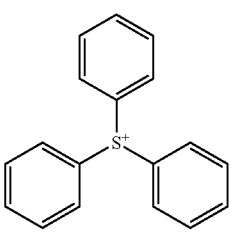 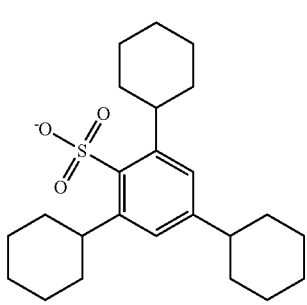

C
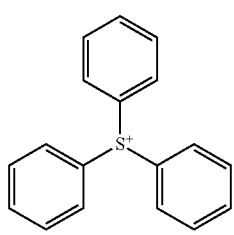 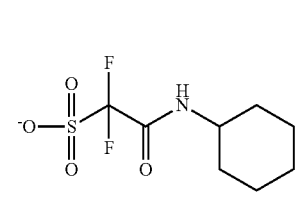

D
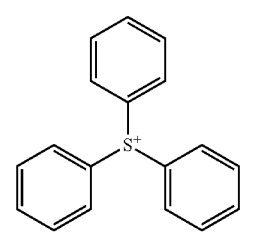 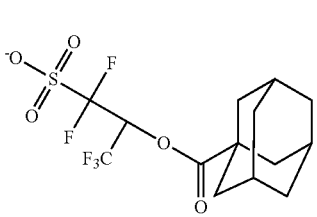

E
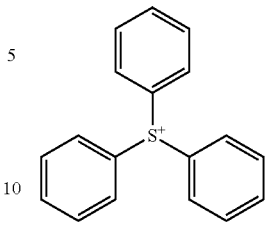 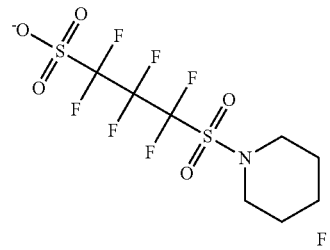

F
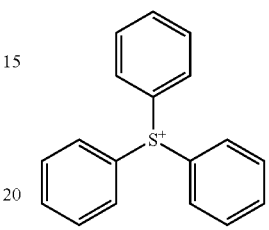 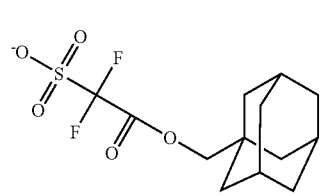

G
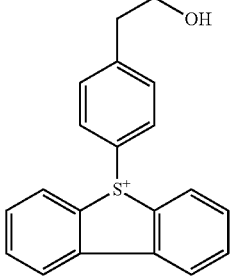 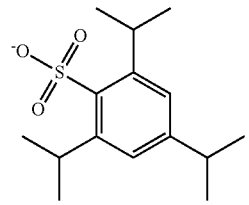 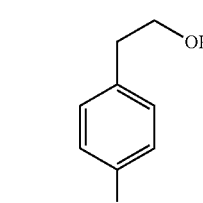

The volume of acid generated by each of the compounds A to G is as follows.

| | |
|---|---|
| A | 303 Å$^3$ |
| B | 437 Å$^3$ |
| C | 227 Å$^3$ |
| D | 266 Å$^3$ |
| E | 244 Å$^3$ |
| F | 271 Å$^3$ |
| G | 303 Å$^3$ |

The compound B was synthesized in, the following manner.

<Synthesis of Tricyclohexylbenzene>

First, 6.83 g of aluminum chloride was added to 20.0 g of benzene, and agitated while cooling at 3° C. Then, 40.4 g of cyclohexyl chloride was slowly dropped thereinto. After the completion of the dropping, the mixture was agitated at room temperature for five hours and poured into ice water. The organic phase was extracted with ethyl acetate, and the obtained, organic phase was subjected to vacuum distillation at 40° C. Further, vacuum distillation was performed at 170° C., and the product was cooled to room temperature. Thereafter, 50 ml of acetone was placed thereinto, and recrystallization was carried out. The resultant crystal was collected by filtration. Thus, 14 g of tricyclohexylbenzene was obtained.

<Synthesis of Sodium Tricyclohexylbenzenesulfonate>

Tricyclohexylbenzene amounting to 30 g was dissolved in 50 ml of methylene chloride and agitated while cooling at 3° C. Then, 15.2 g of chlorosulfonic acid was slowly dropped into the solution. After the completion of the dropping, the mixture was agitated at room temperature for five hours. Subsequently, 10 g of ice and then 40 g of 50% aqueous sodium hydroxide solution was poured into the mixture. Further, 20 g of ethanol was added and agitated at 50° C. for an hour. Any insoluble matter was removed by filtration, and the product was subjected to vacuum distillation at 40° C. The thus obtained crystal was collected by filtration, and washed with hexane, thereby obtaining 30 g of sodium 1,3,5-tricyclohexylbenzenesulfonate.

<Synthesis of Compound B>

Triphenylsulfonium bromide amounting to 4.0 g was dissolved in 20 ml of methanol, and 5.0 g of sodium 1,3,5-tricyclohexylbenzenesulfonate dissolved in 20 ml of methanol was added to the solution. The mixture was agitated at room temperature for two hours, and 50 ml of ion-exchanged water was added to the mixture and extracted with chloroform. The thus obtained organic phase was washed with water and subjected to vacuum distillation at 40° C. The thus obtained crystal was recrystallized from methanol/ethyl acetate, thereby obtaining 5.0 g of compound B.

$^1$H-NMR (400 MHz, $CDCl_3$) δ=7.85 (d, 6H), 7.68 (t, 3H), 7.59 (t, 6H), 6.97 (s, 2H), 4.36-4.27 (m, 2H), 2.48-2.38 (m, 1H), 1.97-1.16 (m, 30H)<

<Basic Compound>

The following compounds C-1 to C-3 were used as basic compounds.

C-1: 2,4,5-triphenylimidazole,
C-2: tetrabutylammonium hydroxide, and
C-3: 1,5-diazabicyclo[4.3.0]non-5-ene.

<Surfactant>

The following surfactants W-1 to W-4 were used.

W-1: Megafac F176 (produced by Dainippon Ink & Chemicals, Inc.; fluorinated),
W-2: Megafac R08 (produced by Dainippon Ink & Chemicals, Inc.; fluorinated and siliconized),
W-3: polysiloxane polymer KP-341 (produced by Shin-Etsu Chemical Co., Ltd.; siliconized), and
W-4: Troy Sol S-366 (produced by Troy Chemical Co., Ltd.; fluorinated).

<Solvent>

As the solvent, use was made of the following solvents A1 to A4, B1 and B2. These solvents were appropriately mixed together before use.

A1: propylene glycol monomethyl ether acetate,
A2: 2-heptanone,
A3: cyclohexanone,
A4: γ-butyrolactone,
B1: propylene glycol monomethyl ether, and
B2: ethyl lactate.

Example A

Examples 1A to 11A and Comparative Examples 1A to 6A (Preparation of Resist)

Referring to Table 2 below, individual components were dissolved in solvents, thereby obtaining solutions each of 4.0 mass % solid content. Each of the solutions was passed through a polytetrafluoroethylene filter of 0.1 μm pore size, thereby obtaining a positive resist solution.

(Evaluation of Resist)

An antireflection film DUV-42 produced by Brewer Science Inc. was uniformly applied at a thickness of 60 nm onto a silicon substrate having undergone a hexamethyldisilazane treatment by means of a spin coater, and dried on a hot plate at 100° C. for 90 seconds. Further drying was carried out by heating at 190° C. for 240 seconds. Thereafter, each of the positive resist solutions was applied thereonto by means of a spin coater and dried at 120° C. for 90 seconds, thereby obtaining a 0.12 μm-thick resist film.

The obtained resist film was exposed through a mask by means of an ArF excimer laser stepper (manufactured by ISI, NA=0.6). Immediately after the exposure, the resist film was baked on a hot plate at 120° C. for 90 seconds. Thereafter, the resist film was developed with a 2.38 mass % aqueous tetramethylammonium hydroxide solution at 23° C. for 60 seconds, rinsed with pure water for 30 seconds and dried. Thus, an intended line pattern was obtained.

[Sensitivity, Resolution (γ)]

Surface exposure was carried out while changing the exposure amount by 0.5 mJ at a time within the range of 10 to 40 mJ/$cm^2$, and the exposed film was baked at 110° C. for 90 seconds. Thereafter, using a 2.38 mass % aqueous tetramethylammonium hydroxide (TMAH) solution, the dissolution rate at each of the exposure amounts was measured, thereby obtaining a dissolution rate curve.

The sensitivity was defined as the exposure amount at which the dissolution rate of the resist was saturated on the dissolution rate curve. Resolution (γ value) was calculated from the gradient of the straight line portion of the dissolution rate curve. The larger the γ value, the more favorable the dissolution contrast.

[Shape of Pattern, Line Edge Roughness (LER)]

The optimum exposure amount was defined as the exposure amount that reproduced a line-and-space (L/S=1/1) mask pattern of 150 nm line width. The profile at the optimum exposure amount was observed by means of a scanning electron microscope (SEM). Further in that pattern, at arbitrary 30 points in a 50 μm region in the longitudinal direction thereof, the distances of actual edges from a reference line on which edges were to be present were measured by means of a scanning electron microscope (model S-9220, manufactured by Hitachi, Ltd.). The standard deviation of measured distances was determined, and 3a was computed.

[Aging Stability]

Each of the compositions was stored at room temperature for a month. The degree of change of sensitivity (sensitivity measured by the above surface exposure method) between before the storage and after the storage was evaluated. The evaluation was effected on the following judgment criteria.

(Judgment Criteria)

○ (Good): when the observed sensitivity change was less than 1 mJ/$cm^2$,

Δ (Fair): when the observed sensitivity change was in the range of 1 to 3 mJ/$cm^2$, and x (Insufficient): when the observed sensitivity change was greater than 3 mJ/$cm^2$.

The obtained evaluation results are given in Table 2 below.

TABLE 2

[ArF; positive]

| Example | Photoacid generator | Sulfonic acid generating compd. | Resin (9.6 g) | Basic compd. (0.02 g) | Surfactant (0.1 mass %) | Solvent (wt. ratio) | Sensitivity (mJ/$cm^2$) | γ | LER (nm) | Pattern shape | Aging stability |
|---|---|---|---|---|---|---|---|---|---|---|---|
| 1A | E (0.4 g) | 1 (0.4 g) | RA-20 | C-1 | W-1 | A1/B1(6/4) | 24.0 | 6.2 | 4.0 | Rectangle | ○ |
| 2A | E (0.4 g) | 4 (0.4 g) | RA-20 | C-1 | W-1 | A2/B2(6/4) | 24.0 | 6.2 | 4.5 | Rectangle | ○ |

TABLE 2-continued

[ArF; positive]

| Example | Photoacid generator | Sulfonic acid generating compd. | Resin (9.6 g) | Basic compd. (0.02 g) | Surfactant (0.1 mass %) | Solvent (wt. ratio) | Sensitivity (mJ/cm$^2$) | γ | LER (nm) | Pattern shape | Aging stability |
|---|---|---|---|---|---|---|---|---|---|---|---|
| 3A | E (0.4 g) | 6 (0.4 g) | RA-20 | C-1 | W-1 | A3/B1(6/4) | 24.0 | 5.5 | 4.9 | Rectangle | ○ |
| 4A | E (0.4 g) | 8 (0.4 g) | RA-20 | C-1 | W-1 | A4/B1(6/4) | 24.0 | 5.5 | 4.5 | Rectangle | ○ |
| 5A | C (0.4 g) | 6 (0.4 g) | RA-20 | C-1 | W-1 | A1/B1(6/4) | 24.0 | 6.1 | 4.2 | Rectangle | ○ |
| 6A | D (0.4 g) | 7 (0.4 g) | RA-20 | C-1 | W-1 | A1/B1(6/4) | 24.0 | 6.7 | 4.8 | Taper | ○ |
| 7A | F (0.4 g) | 6 (0.4 g) | RA-20 | C-3 | W-1 | A1/B1(6/4) | 23.0 | 6.2 | 4.0 | Rectangle | ○ |
| 8A | E (0.4 g) | 6 (0.4 g) | RA-23 | C-1 | W-2 | A1/B1(6/4) | 24.0 | 6.0 | 4.0 | Rectangle | ○ |
| 9A | E (0.4 g) | 6 (0.4 g) | RA-25 | C-1 | W-3 | A1/B1(6/4) | 25.0 | 6.0 | 4.0 | Rectangle | ○ |
| 10A | E (0.4 g) | 6 (0.4 g) | RA-20 | C-2 | W-1 | A1/B1(6/4) | 23.0 | 6.5 | 3.8 | Rectangle | ○ |
| 11A | E (0.6 g) | 6 (0.2 g) | RA-1 | C-1 | W-4 | A1/B1(6/4) | 25.0 | 6.5 | 4.2 | Rectangle | ○ |
| Comparative Example 1A | E (0.4 g) | Comparative compound 1 (0.4 g) | RA-20 | C-1 | W-1 | A1/B1(6/4) | 30.0 | 4.3 | 6.0 | Taper | Δ |
| Comparative Example 2A | E (0.4 g) | Comparative compound 2 (0.4 g) | RA-20 | C-1 | W-1 | A1/B1(6/4) | 30.0 | 5.2 | 5.5 | Taper | Δ |
| Comparative Example 3A | E (0.4 g) | Comparative compound 3 (0.4 g) | RA-20 | C-1 | W-1 | A1/B1(6/4) | 35.0 | 5.2 | 5.5 | Taper | X |
| Comparative Example 4A | E (0.4 g) | Comparative compound 4 (0.4 g) | RA-20 | C-1 | W-1 | A1/B1(6/4) | 35.0 | 5.2 | 5.5 | Taper | X |
| Comparative Example 5A | E (0.4 g) | Comparative compound 5 (0.4 g) | RA-20 | C-1 | W-1 | A1/B1(6/4) | 35.0 | 5.2 | 5.5 | Taper | X |
| Comparative Example 6A | E (0.4 g) | None | RA-20 | C-1 | W-1 | A1/B1(6/4) | 40.0 | 5.2 | 5.5 | Taper | ○ |

The used photoacid generator, sulfonic acid-generating compound, basic compound, surfactant and solvent were appropriately selected from among those set forth hereinbefore.

The used resin was selected from among the following resins (RA-1), (RA-20), (RA-23) and (RA-25). In the following formulae, the numeral appearing on the right side of each repeating unit is a molar ratio. Mw represents a weight average molecular weight, and Mw/Mn represents a molecular weight dispersity.

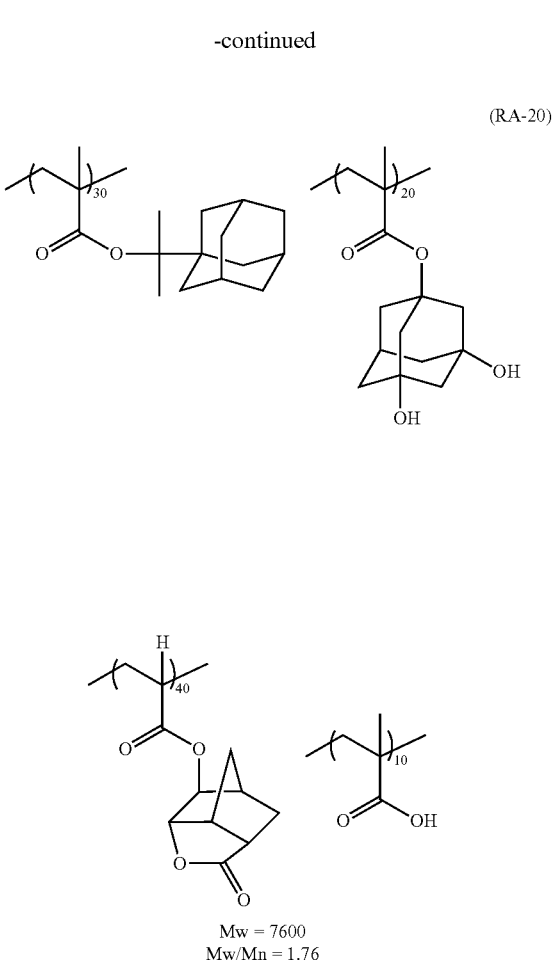

-continued

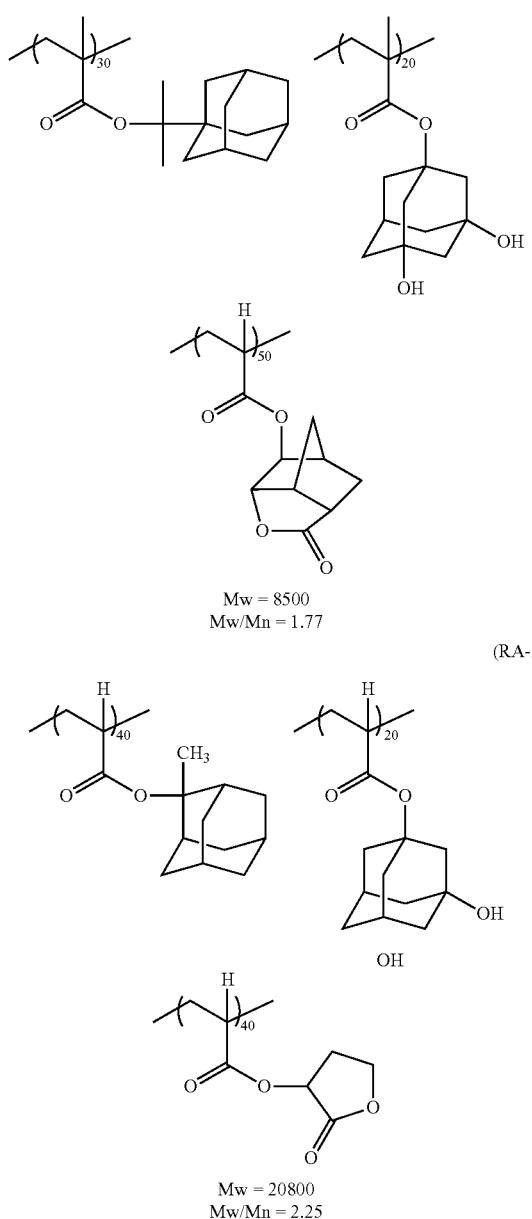

Mw = 8500
Mw/Mn = 1.77

(RA-23)

(RA-25)

Mw = 20800
Mw/Mn = 2.25

It is apparent from the results of Table 2 that in the application of ArF exposure, the composition of the present invention excels in the sensitivity, resolution, roughness characteristic and aging stability. That is, it is apparent that the photosensitive composition of the present invention can exhibit excellent performance as a positive resist composition exposed to an ArF excimer laser.

Example B

A resist solution was prepared according to the same procedure as in Example A except that 0.06 g of the polymer shown below was added to the composition of Example 1A. The resist solution was applied in the same manner, thereby obtaining a resist film. The obtained resist film was patternwise exposed through an immersion liquid (pure water) by means of an ArF excimer laser liquid-immersion scanner (manufactured by ASML, XT1250i, NA 0.85), and a pattern was formed in the same manner as in Example A. It was ascertained that in all of the sensitivity, resolution ($\gamma$), roughness characteristic, shape of pattern and aging stability, the same evaluation results were obtained on the obtained pattern.

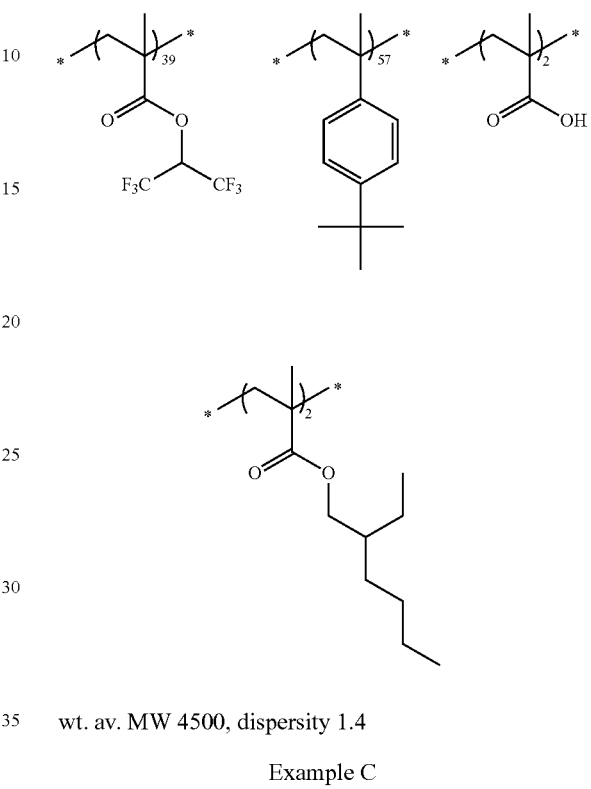

wt. av. MW 4500, dispersity 1.4

Example C

Examples 1C to 19C and Comparative Examples 10 to 6C (Preparation of Resist)
Referring to Table 3 below, individual components were dissolved in solvents and passed through a polytetrafluoroethylene filter of 0.1 μm pore size, thereby obtaining positive resist solutions each of 9.0 mass % solid content.

(Evaluation of Resist)
Each of the obtained positive resist solutions was uniformly applied onto a silicon substrate having undergone a hexamethyldisilazane treatment by means of a spin coater, and dried by heating on a hot plate at 100° C. for 90 seconds, thereby obtaining a 0.4 μm thick resist film.

The obtained resist film was patternwise exposed through a line-and-space mask by means of a KrF excimer laser stepper (NA=0.63). Immediately after the exposure, the resist film was baked on a hot plate at 110° C. for 90 seconds. Thereafter, the resist film was developed with a 2.38 mass % aqueous tetramethylammonium hydroxide solution at 23° C. for 60 seconds, rinsed with pure water for 30 seconds and dried. Thus, an intended line pattern was obtained.

[Sensitivity, Resolution ($\gamma$)]
The sensitivity and resolution ($\gamma$) were determined in the same manner as in Example A except that the above apparatus and process conditions were applied.

[Shape of Pattern, Line Edge Roughness (LER)]
The optimum exposure amount was defined as the exposure amount that reproduced a line-and-space (L/S=1/1)

mask pattern of 180 nm line width. The profile at the optimum exposure amount was observed by means of a scanning electron microscope (SEM). Further, at arbitrary 30 points in a 50 µm region in the longitudinal direction of the formed pattern, the distances of actual edges from a reference line on which edges were to be present were measured by means of a scanning electron microscope (model S-9220, manufactured by Hitachi, Ltd.). The standard deviation of measured distances was determined, and 3σ was computed.

[Aging Stability]

The aging stability was evaluated in the same manner as in Example A.

The obtained evaluation results are given in Table 3 below.

TABLE 3

[KrF; positive]

| Example | Photoacid generator | Sulfonic acid generating compd. | Resin (9.7 g) | Basic compd. (0.02 g) | Surfactant (0.1 mass %) | Solvent (wt. ratio) | Sensitivity (mJ/cm$^2$) | γ | LER (nm) | Pattern shape | Aging stability |
|---|---|---|---|---|---|---|---|---|---|---|---|
| 1C | A (0.3 g) | 1 (0.3 g) | R-18 | C-1 | W-1 | A1/B1(6/4) | 18.0 | 6.3 | 4.3 | Rectangle | ○ |
| 2C | A (0.3 g) | 2 (0.3 g) | R-18 | C-1 | W-1 | A2/B2(6/4) | 18.0 | 6.3 | 4.2 | Rectangle | ○ |
| 3C | A (0.3 g) | 3 (0.3 g) | R-18 | C-1 | W-2 | A3/B1(6/4) | 20.0 | 6.1 | 5.2 | Taper | ○ |
| 4C | A (0.3 g) | 5 (0.3 g) | R-18 | C-1 | W-3 | A4/B1(6/4) | 21.0 | 6.0 | 4.8 | Rectangle | ○ |
| 5C | A (0.3 g) | 6 (0.3 g) | R-18 | C-1 | W-1 | A1/B2(6/4) | 21.0 | 6.0 | 4.9 | Rectangle | ○ |
| 6C | A (0.3 g) | 9 (0.3 g) | R-18 | C-1 | W-1 | A1/B1(6/4) | 20.0 | 6.0 | 4.2 | Rectangle | ○ |
| 7C | A (0.3 g) | 10 (0.3 g) | R-18 | C-1 | W-4 | A1/B1(6/4) | 25.0 | 6.0 | 4.9 | Rectangle | ○ |
| 8C | A (0.3 g) | 11 (0.3 g) | R-18 | C-1 | W-4 | A1/B1(6/4) | 25.3 | 5.5 | 4.8 | Rectangle | ○ |
| 9C | A (0.3 g) | 12 (0.3 g) | R-18 | C-1 | W-1 | Ad/B1(6/4) | 25.0 | 5.0 | 4.8 | Rectangle | ○ |
| 10C | A (0.3 g) | 1 (0.3 g) | R-14 | C-1 | W-1 | A1/B1(6/4) | 20.0 | 6.0 | 4.5 | Rectangle | ○ |
| 11C | A (0.3 g) | 1 (0.3 g) | R-17 | C-1 | W-2 | A1/B1(6/4) | 20.0 | 6.0 | 4.5 | Rectangle | ○ |
| 12C | A (0.3 g) | 1 (0.3 g) | R-2 | C-1 | W-3 | A1/B1(6/4) | 18.0 | 6.5 | 4.3 | Rectangle | ○ |
| 13C | A (0.3 g) | 1 (0.3 g) | R-10 | C-1 | W-1 | A1/B1(6/4) | 20.4 | 6.5 | 4.0 | Rectangle | ○ |
| 14C | E (0.3 g) | 7 (0.3 g) | R-18 | C-1 | W-1 | A1/81(6/4) | 20.2 | 5.0 | 4.5 | Taper | ○ |
| 15C | A (0.5 g) | 1 (0.1 g) | R-18 | C-1 | W-1 | A1/B1(6/4) | 20.2 | 5.0 | 4.5 | Rectangle | ○ |
| 16C | A (0.3 g) | 1 (0.3 g) | R-18 | C-1 | W-1 | A1/B1(6/4) | 18.0 | 6.3 | 3.5 | Rectangle | ○ |
| 17C | A (0.3 g) | 14 (0.3 g) | R-18 | C-1 | W-1 | A1/B1(6/4) | 25.0 | 6.0 | 4.9 | Rectangle | ○ |
| 18C | A (0.3 g) | 15 (0.3 g) | R-18 | C-1 | W-1 | A1/B1(6/4) | 23.0 | 6.0 | 4.5 | Rectangle | ○ |
| 19C | A (0.3 g) | 16 (0.3 g) | R-18 | C-1 | W-1 | A1/B1(6/4) | 23.0 | 6.0 | 4.5 | Rectangle | ○ |
| Comparative Example 1C | A (0.3 g) | Comparative compound 1 (0.3 g) | R-2 | C-1 | W-1 | A1/B1(6/4) | 30.5 | 4.5 | 6.5 | Taper | Δ |
| Comparative Example 2C | A (0.3 g) | Comparative compound 2 (0.3 g) | R-2 | C-1 | W-1 | A1/B1(6/4) | 30.0 | 4.5 | 7.5 | Taper | Δ |
| Comparative Example 3C | A (0.3 g) | Comparative compound 3 (0.4 g) | R-2 | C-1 | W-1 | A1/B1(6/4) | 33.2 | 4.2 | 7.2 | Taper | X |
| Comparative Example 4C | A (0.3 g) | Comparative compound 4 (0.4 g) | R-2 | C-1 | W-1 | A1/B1(6/4) | 33.2 | 4.2 | 7.2 | Taper | X |
| Comparative Example 5C | A (0.3 g) | Comparative compound 5 (0.4 g) | R-2 | C-1 | W-1 | A1/B1(6/4) | 33.0 | 4.2 | 7.2 | Taper | X |
| Comparative Example 6C | A (0.3 g) | None | R-2 | C-1 | W-1 | A1/B1(6/4) | 35.0 | 4.2 | 7.2 | Taper | ○ |

The used photoacid generator, sulfonic acid-generating compound, basic compound, surfactant and solvent were appropriately selected from among those set forth hereinbefore.

The used resin was appropriately selected from among the resins (R-1) to (R-27) set forth hereinbefore by way of example. With respect to each of the resins (R-2), (R-10), (R-14), (R-17), (R-18), (R-18(H)), (R-18(L)), (R-22), (R-23) and (R-27) appearing in Table 3 and the following tables, the molar ratio of individual repeating units and the weight average molecular weight are given in Table 4 below.

TABLE 4

| Resin | Molar ratio of repeating unit (corr. in order fm. left) | Wt. av. mol. wt. (Mw) | Dispersity |
|---|---|---|---|
| R-2 | 60/20/20 | 12000 | 1.7 |
| R-10 | 70/30 | 11000 | 1.6 |
| R-14 | 60/15/25 | 12000 | 1.5 |
| R-17 | 80/20 | 15000 | 1.8 |
| R-18 | 65/35 | 9000 | 1.7 |
| R-18(H) | 60/40 | 10000 | 1.9 |
| R-18(L) | 60/40 | 4000 | 1.2 |
| R-22 | 70/30 | 10000 | 1.9 |

TABLE 4-continued

| Resin | Molar ratio of repeating unit (corr. in order fm. left) | Wt. av. mol. wt. (Mw) | Dispersity |
|---|---|---|---|
| R-23 | 65/35 | 11000 | 1.6 |
| R-27 | 50/40/10 | 12000 | 1.8 |

It is apparent from the results of Table 3 that in the application of KrF exposure, the composition of the present invention excels in the sensitivity, resolution, roughness characteristic and aging stability. That is, it is apparent that the photosensitive composition of the present invention can also exhibit excellent performance as a positive resist composition exposed to an KrF excimer laser.

Example D

Examples 1D to 25D and Comparative Examples 1D to 6D (Preparation of Resist)

Referring to Table 5 below, individual components were dissolved in solvents and passed through a polytetrafluoroethylene filter of 0.1 µm pore size, thereby obtaining positive resist solutions each of 4.0 mass % solid content.

(Evaluation of Resist)

Each of the prepared positive resist solutions was uniformly applied onto a silicon substrate having undergone a hexamethyldisilazane treatment by means of a spin coater, and dried by heating on a hot plate at 100° C. for 60 seconds, thereby obtaining a 0.12 µm-thick resist film.

Each of the resist films was irradiated with electron beams by means of an electron beam projection lithography system (acceleration voltage 100 KeV) manufactured by Nikon Corporation. Immediately after the irradiation, the film was baked on a hot plate at 110° C. for 90 seconds. Thereafter, the baked film was developed with a 2.38 mass % aqueous tetramethylammonium hydroxide solution at 23° C. for 60 seconds. After the development, the film was rinsed with pure•water for 30 seconds and dried. Thus, a line-and-space pattern was formed.

[Sensitivity]

The sensitivity was defined as the electron beam irradiation amount in which a line and space (L/S=i/1) of 0.10 µm line width was resolved.

[Shape of Pattern, Line Edge Roughness (LER)]

The optimum exposure amount was defined as the exposure amount that reproduced a line-and-space (L/S=1/1) pattern of 50 nm line width. The profile at the optimum exposure amount was observed by means of a scanning electron microscope (SEM). LER was determined in the same manner as in Example A.

[Outgassing Performance: Ratio of Change in Film Thickness by Exposure]

Exposure to electron beams was carried out in the exposure amount equal to 2.0 times the exposure amount realizing the above sensitivity (sensitivity determined by the above surface exposure). The film thickness after the exposure but before postbake was measured, and the ratio of change from the film thickness before the exposure was calculated by the following formula.

Ratio of change in film thickness (%)=[(film thickness before exposure−film thickness after exposure)/ (film thickness before exposure)]×100.

[Aging Stability]

Each of the compositions was stored at room temperature for a month. The degree of change of sensitivity (sensitivity measured by the above surface exposure) between before the storage and after the storage was evaluated. The evaluation was effected on the following judgment criteria.

(Judgment Criteria)

○ (Good): when the sensitivity change was less than 1 µC/cm$^2$,

Δ (Fair): when the sensitivity change was in the range of 1 to 3 µC/cm$^2$, and x (Insufficient): when the sensitivity change was greater than 3 µC/cm$^2$.

The obtained evaluation results are given in Table 5 below.

TABLE 5

[Exposure to electron beam; positive]

| Example | Photoacid generator | Sulfonic acid generating compd. | Resin (9.7 g) | Basic compd. (0.02 g) | Surfactant (0.1 mass %) | Solvent (wt. ratio) | Sensitivity (µC/cm$^2$) | Pattern shape | LER (nm) | Ratio of film thickness change (%) | Aging stability |
|---|---|---|---|---|---|---|---|---|---|---|---|
| 1D | A (0.3 g) | 1 (0.3 g) | R-18(H) | C-2 | W-1 | A1/B1(6/4) | 10.3 | Rectangle | 4.3 | 1.8 | ○ |
| 2D | A (0.3 g) | 2 (0.3 g) | R-18(H) | C-2 | W-1 | A1/B1(6/4) | 10.5 | Rectangle | 4.1 | 1.3 | ○ |
| 3D | A (0.3 g) | 3 (0.3 g) | R-18(H) | C-2 | W-1 | A1/B1(6/4) | 12.5 | Taper | 5.2 | 1.5 | ○ |
| 4D | A (0.3 g) | 4 (0.3 g) | R-18(H) | C-1 | W-1 | A1/B1(6/4) | 10.0 | Rectangle | 4.8 | 1.7 | Δ |
| 5D | A (0.3 g) | 5 (0.3 g) | R-18(H) | C-2 | W-1 | A1/B1(6/4) | 10.1 | Rectangle | 4.9 | 1.5 | ○ |
| 6D | A (0.3 g) | 6 (0.3 g) | R-18(H) | C-2 | W-1 | A1/B1(6/4) | 10.2 | Rectangle | 4.9 | 1.5 | ○ |
| 7D | A (0.3 g) | 7 (0.3 g) | R-18(H) | C-2 | W-1 | A1/B1(6/4) | 10.1 | Taper | 5.5 | 1.5 | ○ |
| 8D | A (0.3 g) | 8 (0.3 g) | R-18(H) | C-2 | W-1 | A1/B1(6/4) | 10.3 | Rectangle | 4.9 | 1.4 | Δ |
| 9D | A (0.3 g) | 9 (0.3 g) | R-18(H) | C-2 | W-1 | A1/B1(6/4) | 10.2 | Rectangle | 4.3 | 1.6 | ○ |
| 10D | A (0.3 g) | 10 (0.3 g) | R-18(H) | C-2 | W-1 | A1/B1(6/4) | 14.3 | Rectangle | 4.9 | 1.7 | ○ |
| 11D | A (0.3 g) | 11 (0.3 g) | R-18(H) | C-2 | W-1 | A1/B1(6/4) | 15.5 | Rectangle | 4.8 | 1.8 | ○ |
| 12D | A (0.3 g) | 12 (0.3 g) | R-18(H) | C-2 | W-1 | A1/B1(6/4) | 14.2 | Rectangle | 4.9 | 1.6 | ○ |
| 13D | A (0.3 g) | 13 (0.3 g) | R-18(H) | C-2 | W-1 | A1/B1(6/4) | 10.5 | Rectangle | 4.0 | 1.0 | ○ |
| 14D | A (0.3 g) | 1 (0.3 g) | R-14 | C-2 | W-1 | A1/B1(6/4) | 10.2 | Rectangle | 4.1 | 1.5 | ○ |
| 15D | A (0.3 g) | 1 (0.3 g) | R-17 | C-2 | W-1 | A1/B1(6/4) | 10.5 | Rectangle | 4.2 | 1.7 | ○ |
| 16D | A (0.3 g) | 1 (0.3 g) | R-18(L) | C-2 | W-1 | A1/B1(6/4) | 10.4 | Rectangle | 3.5 | 1.6 | ○ |
| 17D | A (0.3 g) | 1 (0.3 g) | R-2 | C-2 | W-1 | A1/B1(6/4) | 10.2 | Rectangle | 4.0 | 1.6 | ○ |
| 18D | A (0.3 g) | 1 (0.3 g) | R-22 | C-2 | W-1 | A1/B1(6/4) | 10.5 | Rectangle | 4.2 | 1.6 | ○ |
| 19D | E (0.3 g) | 6 (0.3 g) | R-23 | C-2 | W-1 | A1/B1(6/4) | 10.3 | Rectangle | 4.9 | 1.5 | ○ |
| 20D | E (0.3 g) | 6 (0.3 g) | R-27 | C-2 | W-1 | A1/B1(6/4) | 10.2 | Rectangle | 4.9 | 1.5 | ○ |
| 21D | F (0.3 g) | 8 (0.3 g) | R-27 | C-2 | W-1 | A1/B1(6/4) | 10.2 | Rectangle | 4.8 | 1.5 | ○ |
| 22D | A (0.5 g) | 1 (0.1 g) | R-18(H) | C-2 | W-1 | A1/B1(6/4) | 13.3 | Rectangle | 4.4 | 1.8 | ○ |
| 23D | A (0.3 g) | 14 (0.3 g) | R-18(H) | C-2 | W-1 | A1/B1(6/4) | 15.6 | Rectangle | 4.8 | 1.8 | ○ |
| 24D | A (0.3 g) | 15 (0.3 g) | R-18(H) | C-2 | W-1 | A1/B1(6/4) | 14.6 | Rectangle | 4.8 | 3.8 | ○ |
| 25D | A (0.3 g) | 16 (0.3 g) | R-18(H) | C-2 | W-1 | A1/B1(6/4) | 14.3 | Rectangle | 4.8 | 1.8 | ○ |
| Comparative Example 1D | A (0.3 g) | Comparative compound 1 (0.3 g) | R-2 | C-1 | W-1 | A1/B1(6/4) | 20.8 | Taper | 7.0 | 1.5 | Δ |
| Comparative Example 2D | A (0.3 g) | Comparative compound 2 (0.3 g) | R-2 | C-1 | W-1 | A1/B1(6/4) | 20.9 | Taper | 7.0 | 1.5 | Δ |

TABLE 5-continued

[Exposure to electron beam; positive]

| Example | Photoacid generator | Sulfonic acid generating compd. | Resin (9.7 g) | Basic compd. (0.02 g) | Surfactant (0.1 mass %) | Solvent (wt. ratio) | Sensitivity ($\mu$C/cm$^2$) | Pattern shape | LER (nm) | Ratio of film thickness change (%) | Aging stability |
|---|---|---|---|---|---|---|---|---|---|---|---|
| Comparative Example 3D | A (0.3 g) | Comparative compound 3 (0.3 g) | R-2 | C-1 | W-1 | A1/B1(6/4) | 25.2 | Taper | 7.0 | 1.5 | X |
| Comparative Example 4D | A (0.3 g) | Comparative compound 4 (0.3 g) | R-2 | C-1 | W-1 | A1/B1(6/4) | 25.1 | Taper | 6.9 | 1.5 | X |
| Comparative Example 5D | A (0.3 g) | Comparative compound 5 (0.3 g) | R-2 | C-1 | W-1 | A1/B1(6/4) | 26.0 | Taper | 6.8 | 1.5 | X |
| Comparative Example 6D | A (0.3 g) | None | R-2 | C-1 | W-1 | A1/B1(6/4) | 30.1 | Taper | 7.2 | 1.5 | ○ |

It is apparent from the results of Table 5 that in the exposure to electron beams, the composition of the present invention excels in the sensitivity, roughness characteristic, outgassing performance and aging stability. That is, it is apparent that the photosensitive composition of the present invention can also exhibit excellent performance as a positive resist composition exposed to electron beams.

Example E

Examples 1E to 14E and Comparative Examples 1E to 6E (Preparation of Resist)

Referring to Table 6 below, individual components were dissolved in solvents and passed through a polytetrafluoroethylene filter of 0.1 μm pore size, thereby obtaining negative resist solutions each of 4.0 mass % solid content.

(Evaluation of Resist)

Each of the prepared negative resist solutions was uniformly applied onto a silicon substrate having undergone a hexamethyldisilazane treatment by means of a spin coater, and dried by heating on a hot plate at 120° C. for 60 seconds, thereby obtaining a 0.12 μm-thick resist film.

Each of the resist films was irradiated with electron beams by means of an electron beam projection lithography system (acceleration voltage 100 KeV) manufactured by Nikon Corporation. Immediately after the irradiation, the film was baked on a hot plate at 110° C. for 90 seconds. Thereafter, the baked film was developed with a 2.38 mass % aqueous tetramethylammonium hydroxide solution at 23° C. for 60 seconds. After the development, the film was rinsed with pure water for 30 seconds and dried. Thus, a line-and-space pattern was formed.

Evaluation was conducted in the same manner as in Example D. The evaluation results are given in Table 6.

TABLE 6

[Exposure to electron beam; negative]

| Example | Photoacid generator | Sulfonic acid generating compd. | Resin (9.7 g) | Cross-linking agent (3.0 g) | Basic compd. (0.02 g) | Surfactant (0.1 mass %) | Solvent (wt. ratio) | Sensitivity ($\mu$C/cm$^2$) | Pattern shape | LER (nm) | Ratio of film thickness change (%) | Aging stability |
|---|---|---|---|---|---|---|---|---|---|---|---|---|
| 1E | A (0.3 g) | 1 (0.3 g) | P-3 | CL-1 | C-1 | W-1 | A1/B1(6/4) | 13.8 | Rectangle | 4.5 | 1.8 | ○ |
| 2E | A (0.3 g) | 2 (0.3 g) | P-3 | CL-1 | C-1 | W-2 | A2/B2(6/4) | 13.8 | Rectangle | 4.6 | 1.8 | ○ |
| 3E | A (0.3 g) | 3 (0.3 g) | P-3 | CL-1 | C-1 | W-3 | A3/B1(6/4) | 13.5 | Taper | 5.4 | 1.5 | ○ |
| 4E | A (0.3 g) | 4 (0.3 g) | P-3 | CL-1 | C-1 | W-1 | A4/B1(6/4) | 13.8 | Rectangle | 4.9 | 1.5 | ○ |
| 5E | A (0.3 g) | 9 (0.3 g) | P-3 | CL-1 | C-1 | W-3 | A1/B2(6/4) | 13.8 | Rectangle | 4.2 | 1.7 | ○ |
| 6E | A (0.3 g) | 10 (0.3 g) | P-3 | CL-1 | C-1 | W-2 | A1/B1(6/4) | 16.8 | Rectangle | 4.9 | 1.7 | ○ |
| 7E | A (0.3 g) | 11 (0.3 g) | P-3 | CL-1 | C-1 | W-4 | A1/B1(6/4) | 17.8 | Rectangle | 4.9 | 1.5 | ○ |
| 8E | A (0.3 g) | 12 (0.3 g) | P-3 | CL-1 | C-1 | W-4 | A1/B1(6/4) | 16.8 | Rectangle | 4.8 | 1.5 | ○ |
| 9E | A (0.3 g) | 13 (0.3 g) | P-2 | CL-1 | C-1 | W-1 | A1/B1(6/4) | 14.0 | Rectangle | 4.5 | 1.8 | ○ |
| 10E | A (0.3 g) | 1 (0.3 g) | P-1 | CL-1 | C-1 | W-1 | A1/B1(6/4) | 14.2 | Rectangle | 4.5 | 1.5 | ○ |
| 11E | A (0.3 g) | 1 (0.3 g) | P-3 | CL-2 | C-1 | W-1 | A1/B1(6/4) | 13.5 | Rectangle | 4.4 | 1.5 | ○ |
| 12E | A (0.3 g) | 1 (0.3 g) | P-3 | CL-3 | C-1 | W-1 | A1/B1(6/4) | 13.5 | Rectangle | 4.5 | 1.5 | ○ |
| 13E | A (0.3 g) | 1 (0.3 g) | P-3 | CL-1 | C-2 | W-1 | A1/B1(6/4) | 3.0 | Rectangle | 4.4 | 1.5 | ○ |
| 14E | A (0.3 g) | 1 (0.15 g) | P-3 | CL-1 | C-2 | W-2 | A1/B1(6/4) | 13.8 | Rectangle | 4.7 | 1.7 | ○ |
| Comparative Example 1E | A (0.3 g) | Comparative compound 1 (0.3 g) | P-1 | CL-1 | C-1 | W-1 | A1/B1(6/4) | 29.8 | Taper | 8.8 | 1.6 | Δ |
| Comparative Example 2E | A (0.3 g) | Comparative compound 2 (0.3 g) | P-1 | CL-1 | C-1 | W-1 | A1/B1(6/4) | 29.8 | Taper | 8.9 | 1.6 | Δ |
| Comparative Example 3E | A (0.3 g) | Comparative compound 3 (0.3 g) | P-1 | CL-1 | C-1 | W-1 | A1/B1(6/4) | 30.2 | Taper | 8.9 | 1.7 | X |
| Comparative Example 4E | A (0.3 g) | Comparative compound 4 (0.3 g) | P-1 | CL-1 | C-1 | W-1 | A1/B1(6/4) | 29.8 | Taper | 8.0 | 1.5 | X |

TABLE 6-continued

[Exposure to electron beam; negative]

| Example | Photoacid generator | Sulfonic acid generating compd. | Resin (9.7 g) | Cross-linking agent (3.0 g) | Basic compd. (0.02 g) | Surfactant (0.1 mass %) | Solvent (wt. ratio) | Sensitivity ($\mu C/cm^2$) | Pattern shape | LER (nm) | Ratio of film thickness change (%) | Aging stability |
|---|---|---|---|---|---|---|---|---|---|---|---|---|
| Comparative Example 5E | A (0.3 g) | Comparative compound 5 (0.3 g) | P-1 | CL-1 | C-1 | W-1 | A1/B1(6/4) | 29.8 | Taper | 8.0 | 1.5 | X |
| Comparative Example 6E | A (0.3 g) | None | P-1 | CL-1 | C-1 | W-1 | A1/B1(6/4) | 33.8 | Taper | 8.1 | 1.5 | ○ |

The structures, molecular weights and molecular weight distributions of employed alkali-soluble resins are shown below. Also, the structures of employed acid crosslinking agents are shown below.

| | | Mw | Mw/Mn |
|---|---|---|---|
| P-1 | 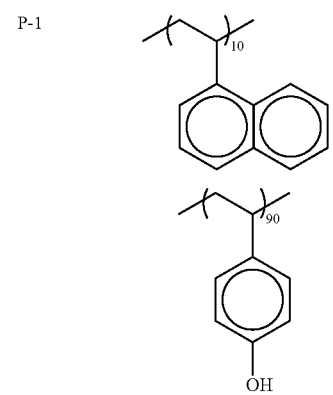 | 16000 | 2.30 |
| P-2 | 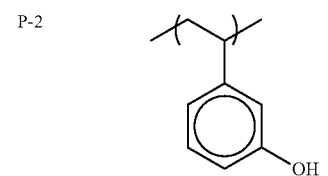 | 12000 | 1.2 |
| P-3 | 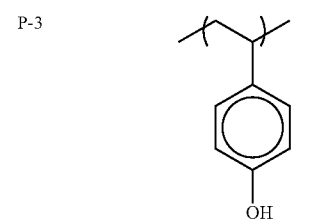 | 6000 | 1.2 |

VP-5000 produced by Nippon Soda Co., Ltd.

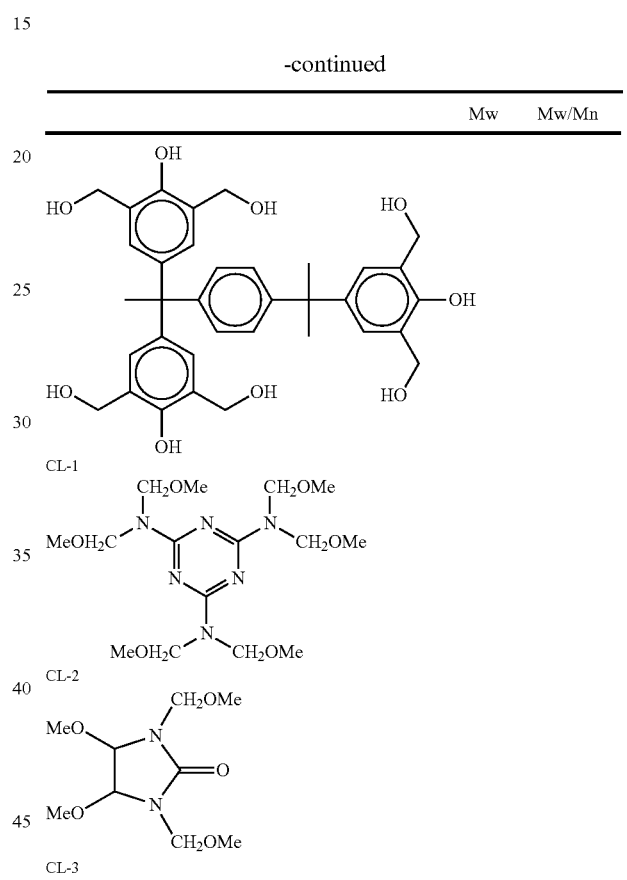

It is apparent from the results of Table 6 that in the exposure to electron beams, the composition of the present invention excels in the sensitivity, roughness characteristic, outgassing performance and aging stability. That is, it is apparent that the photosensitive composition of the present invention can also exhibit excellent performance as a negative resist composition exposed to electron beams.

Example F

Examples 1F to 25F and Comparative Examples 1F to 6E'

(Preparation of Resist)

Referring to Table 7 below, individual components were dissolved in solvents and passed through a polytetrafluoroethylene filter of 0.1 μm pore size, thereby obtaining positive resist solutions each of 4.0 mass % solid content.

(Evaluation of Resist)

Each of the prepared positive resist solutions was uniformly applied onto a silicon substrate having undergone a hexamethyldisilazane treatment by means of a spin coater, and dried by heating on a hot plate at 100° C. for 60 seconds, thereby obtaining a 0.12 μm-thick resist film.

[Sensitivity]

The surface exposure of each of the obtained resist films was carried out using EUV light (wavelength 13 nm) while changing the exposure amount by 0.5 mJ/cm² at a time within the range of 0 to 35.0 mJ/cm². The exposed film was baked at 110° C. for 90 seconds. Thereafter, using a 2.38 mass % aqueous tetramethylammonium hydroxide (TMAH) solution, the dissolution rate at each exposure amount was measured, thereby obtaining a dissolution rate curve. The sensitivity was defined as the exposure amount at which the dissolution rate of the resist was saturated on the dissolution rate curve.

[Shape of Pattern, Line Edge Roughness (LER)]

The optimum exposure amount was defined as the exposure amount that reproduced a line-and-space (L/S=1/1) mask pattern of 50 nm line width. The profile at the optimum exposure amount was observed by means of a scanning electron microscope (SEM). Further, at arbitrary 30 points in a 50 μm region in the longitudinal direction of the pattern, the distances of actual edges from a reference line on which edges were to be present were measured by means of a scanning electron microscope (model S-9220, manufactured by Hitachi, Ltd.). The standard deviation of measured distances was determined, and 3σ was computed.

[Outgassing Performance: Ratio of Change in Film Thickness by Exposure]

The ratio of change in film thickness by exposure to EUV light was determined in the same manner as in Example D.

The aging stability was evaluated in the same manner as in Example A.

The obtained evaluation results are given in Table 7 below.

TABLE 7

[EUV exposure; positive]

| Example | Photoacid generator | Sulfonic acid generating compd. | Resin (9.7 g) | Basic compd. (0.02 g) | Surfactant (0.1 mass %) | Solvent (wt. ratio) | Sensitivity (mJ/cm²) | Pattern shape | LER (nm) | Ratio of film thickness change (%) | Aging stability |
|---|---|---|---|---|---|---|---|---|---|---|---|
| 1F | A (0.3 g) | 1 (0.3 g) | R-18(H) | C-2 | W-1 | A1/B1(6/4) | 12.3 | Rectangle | 5.0 | 1.8 | ○ |
| 2F | A (0.3 g) | 2 (0.3 g) | R-18(H) | C-2 | W-1 | A1/B1(6/4) | 12.5 | Rectangle | 4.8 | 1.3 | ○ |
| 3F | A (0.3 g) | 3 (0.3 g) | R-18(H) | C-2 | W-1 | A1/B1(6/4) | 12.5 | Taper | 6.0 | 1.5 | ○ |
| 4F | A (0.3 g) | 4 (0.3 g) | R-18(H) | C-1 | W-1 | A1/B1(6/4) | 12.0 | Rectangle | 5.1 | 1.5 | Δ |
| 5F | A (0.3 g) | 5 (0.3 g) | R-18(H) | C-2 | W-1 | A1/B1(6/4) | 13.1 | Rectangle | 5.9 | 3.5 | ○ |
| 6F | A (0.3 g) | 6 (0.3 g) | R-18(H) | C-2 | W-1 | A1/B1(6/4) | 12.2 | Rectangle | 5.9 | 1.5 | ○ |
| 7F | A (0.3 g) | 7 (0.3 g) | R-18(H) | C-2 | W-1 | A1/B1(6/4) | 12.1 | Taper | 6.2 | 1.5 | ○ |
| 8F | A (0.3 g) | 8 (0.3 g) | R-18(H) | C-2 | W-1 | A1/B1(6/4) | 12.3 | Rectangle | 5.9 | 1.4 | Δ |
| 9F | A (0.3 g) | 9 (0.3 g) | R-18(H) | C-2 | W-1 | A1/B1(6/4) | 12.2 | Rectangle | 5.0 | 1.6 | ○ |
| 10F | A (0.3 g) | 10 (0.3 g) | R-18(H) | C-2 | W-1 | A1/B1(6/4) | 15.3 | Rectangle | 4.8 | 1.5 | ○ |
| 11F | A (0.3 g) | 11 (0.3 g) | R-18(H) | C-2 | W-1 | A1/B1(6/4) | 15.5 | Rectangle | 4.9 | 1.8 | ○ |
| 12F | A (0.3 g) | 12 (0.3 g) | R-18(H) | C-2 | W-1 | A1/B1(6/4) | 15.2 | Rectangle | 4.8 | 1.5 | ○ |
| 13F | A (0.3 g) | 13 (0.3 g) | R-18(H) | C-2 | W-1 | A1/B1(6/4) | 12.2 | Rectangle | 5.0 | 1.5 | ○ |
| 14F | A (0.3 g) | 1 (0.3 g) | R-14 | C-2 | W-1 | A1/B1(6/4) | 13.2 | Rectangle | 5.1 | 1.5 | ○ |
| 15F | A (0.3 g) | 1 (0.3 g) | R-17 | C-2 | W-1 | A1/B1(6/4) | 13.4 | Rectangle | 5.2 | 1.5 | ○ |
| 16F | A (0.3 g) | 1 (0.3 g) | R-18(L) | C-2 | W-1 | A1/B1(6/4) | 11.4 | Rectangle | 4.5 | 1.6 | ○ |
| 17F | A (0.3 g) | 1 (0.3 g) | R-2 | C-2 | W-1 | A1/B1(6/4) | 12.2 | Rectangle | 5.0 | 4.0 | ○ |
| 18F | A (0.3 g) | 1 (0.3 g) | R-22 | C-2 | W-1 | A1/B1(6/4) | 13.2 | Rectangle | 6.2 | 2.5 | ○ |
| 19F | E (0.3 g) | 7 (0.3 g) | R-23 | C-2 | W-1 | A1/B1(6/4) | 13.2 | Taper | 6.1 | 3.5 | ○ |
| 20F | E (0.3 g) | 7 (0.3 g) | R-27 | C-2 | W-1 | A1/B1(6/4) | 13.2 | Taper | 6.0 | 1.5 | ○ |
| 21F | F (0.3 g) | 8 (0.3 g) | R-27 | C-2 | W-1 | A1/B1(6/4) | 13.2 | Rectangle | 6.0 | 1.5 | ○ |
| 22F | A (0.5 g) | 1 (0.1 g) | R-18(H) | C-2 | W-1 | A1/B1(6/4) | 14.3 | Rectangle | 5.0 | 1.8 | ○ |
| 23F | A (0.3 g) | 14 (0.3 g) | R-18(H) | C-2 | W-1 | A1/B1(6/4) | 15.5 | Rectangle | 4.8 | 1.5 | ○ |
| 24F | A (0.3 g) | 15 (0.3 g) | R-18(H) | C-2 | W-1 | A1/B1(6/4) | 14.6 | Rectangle | 4.8 | 3.8 | ○ |
| 25F | A (0.3 g) | 16 (0.3 g) | R-18(H) | C-2 | W-1 | A1/B1(6/4) | 14.3 | Rectangle | 4.8 | 1.8 | ○ |
| Comparative Example 1F | A (0.3 g) | Comparative compound 1 (0.3 g) | R-2 | C-1 | W-1 | A1/B1(6/4) | 22.0 | Taper | 8.0 | 1.5 | Δ |
| Comparative Example 2F | A (0.3 g) | Comparative compound 2 (0.3 g) | R-2 | C-1 | W-1 | A1/B1(6/4) | 22.0 | Taper | 8.0 | 1.5 | Δ |
| Comparative Example 3F | A (0.3 g) | Comparative compound 3 (0.3 g) | R-2 | C-1 | W-1 | A1/B1(6/4) | 24.0 | Taper | 7.0 | 1.5 | X |
| Comparative Example 4F | A (0.3 g) | Comparative compound 4 (0.3 g) | R-2 | C-1 | W-1 | A1/B1(6/4) | 24.0 | Taper | 7.0 | 1.5 | X |
| Comparative Example 5F | A (0.3 g) | Comparative compound 5 (0.3 g) | R-2 | C-1 | W-1 | A1/B1(6/4) | 24.0 | Taper | 7.0 | 1.5 | X |
| Comparative Example 6F | A (0.3 g) | None | R-2 | C-1 | W-1 | A1/B1(6/4) | 30.0 | Taper | 7.5 | 1.5 | ○ |

It is apparent from the results of Table 7 that in the exposure to EUV, the composition of the present invention excels in the sensitivity, roughness characteristic, outgassing performance and aging stability. That is, it is apparent that the photosensitive composition of the present invention can also exhibit excellent performance as a positive resist composition exposed to EUV.

Example G

Examples 1G to 8G and Comparative Examples 1G to 6G (Preparation of Resist)

Referring to Table 8 below, individual components were dissolved in solvents and passed through a polytetrafluoroethylene filter of 0.1 μm pore size, thereby obtaining negative resist solutions each of 4.0 mass % solid content. The negative resist solutions were evaluated in the following manner.

<Evaluation of Resist>

Each of the prepared negative resist solutions was uniformly applied onto a silicon substrate having undergone a hexamethyldisilazane treatment by means of a spin coater, and dried by heating on a hot plate at 120° C. for 60 seconds, thereby obtaining a 0.12 μm-thick resist film.

The resist films were evaluated in the same manner as in Example F. The results are given in Table 8 below.

It is apparent from the results of Table 8 that in the exposure to EUV, the composition of the present invention excels in the sensitivity, roughness characteristic, outgassing performance and aging stability. That is, it is apparent that the photosensitive composition of the present invention can also exhibit excellent performance as a negative resist composition exposed to EUV.

The present invention has made it feasible to provide an actinic ray- or radiation-sensitive resin composition excelling in the sensitivity, roughness characteristic and aging stability and to provide a method of forming a pattern using the composition.

What is claimed is:

1. An actinic ray- or radiation-sensitive resin composition comprising:
   a sulfonic acid-generating compound that is decomposed by an action of an acid to generate a sulfonic acid having a volume of 240 Å$^3$ or more;
   a compound that generates the acid when exposed to actinic rays or radiation; and
   further comprising a resin that is decomposed by an action of the acid to increase its solubility in an alkaline developer,
   wherein
   the sulfonic acid-generating compound is any of compounds of general formulae (1) to (5) below and the sulfonic acid is represented by a formula A-SO$_3$H,

TABLE 8

[EUV exposure; negative]

| Example | Photoacid generator | Sulfonic acid generating compd. | Resin (10 g) | Cross-linking agent (3.0 g) | Basic compd. (0.02 g) | Surfactant (0.1 mass %) | Solvent (wt. ratio) | Sensitivity (mJ/cm$^2$) | Pattern shape | LER (nm) | Ratio of film thickness change (%) | Aging stability |
|---|---|---|---|---|---|---|---|---|---|---|---|---|
| 1G | A (0.3 g) | 1 (0.3 g) | P-3 | CL-1 | C-2 | W-1 | A1/B1(6/4) | 10.3 | Rectangle | 6.2 | 1.8 | ○ |
| 2G | A (0.3 g) | 2 (0.3 g) | P-3 | CL-1 | C-2 | W-2 | A1/B1(6/4) | 10.8 | Rectangle | 6.0 | 4.5 | ○ |
| 3G | A (0.3 g) | 3 (0.3 g) | P-3 | CL-1 | C-2 | W-3 | A1/B1(6/4) | 10.0 | Taper | 7.0 | 1.8 | ○ |
| 4G | A (0.3 g) | 4 (0.3 g) | P-3 | CL-2 | C-2 | W-1 | A1/B1(6/4) | 12.3 | Rectangle | 6.5 | 1.9 | ○ |
| 5G | A (0.3 g) | 13 (0.3 g) | P-3 | CL-3 | C-2 | W-1 | A1/B1(6/4) | 10.3 | Rectangle | 6.2 | 1.0 | ○ |
| 6G | A (0.3 g) | 10 (0.3 g) | P-3 | CL-3 | C-2 | W-1 | A1/B1(6/4) | 15.3 | Rectangle | 6.5 | 1.9 | ○ |
| 7G | A (0.3 g) | 11 (0.3 g) | P-3 | CL-3 | C-2 | W-1 | A1/B1(6/4) | 15.5 | Rectangle | 6.6 | 1.9 | ○ |
| 8G | A (0.3 g) | 12 (0.3 g) | P-3 | CL-3 | C-2 | W-1 | A1/B1(6/4) | 15.3 | Rectangle | 6.7 | 1.9 | ○ |
| Comparative Example 1G | A (0.3 g) | Comparative compound 1 (0.3 g) | P-1 | CL-1 | C-1 | W-1 | A1/B1(6/4) | 22.0 | Taper | 10.1 | 1.2 | Δ |
| Comparative Example 2G | A (0.3 g) | Comparative compound 2 (0.3 g) | P-1 | CL-1 | C-1 | W-1 | A1/B1(6/4) | 22.5 | Taper | 11.3 | 1.2 | Δ |
| Comparative Example 3G | A (0.3 g) | Comparative compound 3 (0.3 g) | P-1 | CL-1 | C-1 | W-1 | A1/B1(6/4) | 26.0 | Taper | 11.1 | 1.2 | X |
| Comparative Example 4G | A (0.3 g) | Comparative compound 4 (0.3 g) | P-1 | CL-1 | C-1 | W-1 | A1/B1(6/4) | 27.0 | Taper | 11.1 | 1.5 | X |
| Comparative Example 5G | A (0.3 g) | Comparative compound 5 (0.3 g) | P-1 | CL-1 | C-1 | W-1 | A1/B1(6/4) | 28.0 | Taper | 10.0 | 1.5 | X |
| Comparative Example 6G | A (0.3 g) | None | P-1 | CL-1 | C-1 | W-1 | A1/B1(6/4) | 35.0 | Taper | 10.1 | 1.5 | ○ |

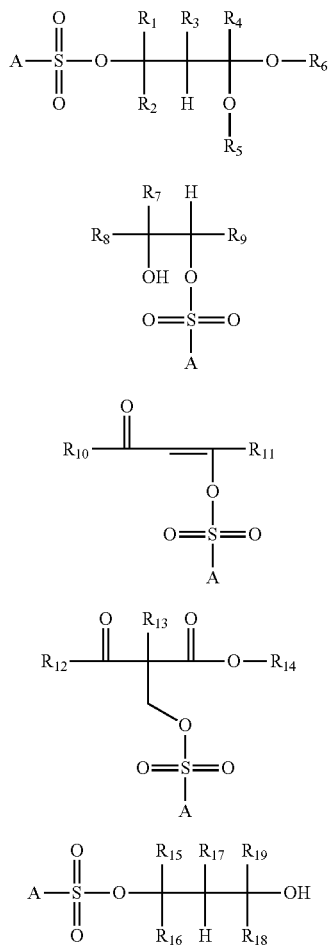

where
each of $R_1$ to $R_4$, $R_7$ to $R_{13}$ and $R_{15}$ to $R_{19}$ represents a hydrogen atom or a monovalent substituent,
each of $R_5$, $R_6$ and $R_{14}$ represents a monovalent substituent, and
A in the formula $A\text{-}SO_3H$ represents a residue of the sulfonic acid,
and wherein,
the sulfonic acid represented by the formula $A\text{-}SO_3H$ is a compound of the following general formula (6),

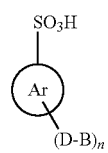

(6)

in which
Ar represents an aryl group, in which a substituent other than the -(D-B) group may further be introduced,
n is an integer of 1 or greater,
D represents a single bond or a bivalent connecting group, and
B represents a hydrocarbon group.

2. The actinic ray- or radiation-sensitive resin composition according to claim 1, wherein the resin that is decomposed by an action of the acid to increase its solubility in the alkaline developer is a resin comprising a repeating units represented by a general formula (A) below,

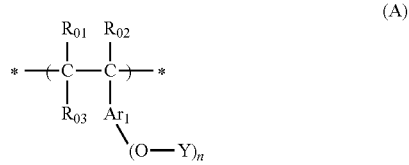

(A)

where
each of $R_{01}$, $R_{02}$ and $R_{03}$ independently represents a hydrogen atom, an alkyl group, a cycloalkyl group, a halogen atom, a cyano group or an alkoxycarbonyl group,
$Ar_1$ represents an aromatic ring group, provided that $Ar_1$ and $R_{03}$ may be bonded to each other so as to form a ring together with a —C—C— chain,
nY s, each independently, represents a hydrogen atom or a group that is eliminated by an action of the acid, provided that at least one of Ys is a group that is eliminated by the action of the acid, and
n is an integer of 1 to 4.

3. The actinic ray- or radiation-sensitive resin composition according to claim 1 to be exposed to electron beams, X-rays or EUV light.

4. A method of forming a pattern, comprising:
forming a film using the composition according to claim 1,
subjecting the film to exposure, and
developing the exposed film.

5. An actinic ray- or radiation-sensitive resin composition comprising:
a sulfonic acid-generating compound that is decomposed by an action of an acid to generate a sulfonic acid having a volume of 240 Å$^3$ or more;
a compound that generates the acid when exposed to actinic rays or radiation; and
further comprising a resin soluble in an alkaline developer and an acid crosslinking agent capable of crosslinking with the resin by an action of the acid,
wherein
the sulfonic acid-generating compound is any of compounds of general formulae (1) to (5) below and the sulfonic acid is represented by a formula $A\text{-}SO_3H$,

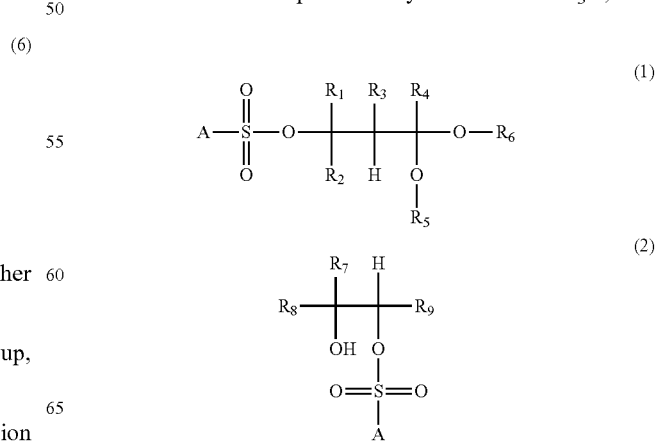

-continued

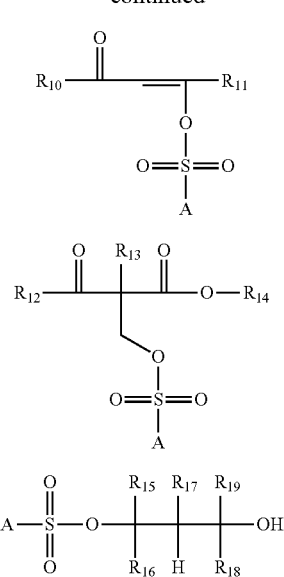

where
each of $R_1$ to $R_4$, $R_7$ to $R_{13}$ and $R_{15}$ to $R_{19}$ represents a hydrogen atom or a monovalent substituent,
each of $R_5$, $R_6$ and $R_{14}$ represents a monovalent substituent, and
A in the formula $A\text{-SO}_3H$ represents a residue of the sulfonic acid,
and wherein
the sulfonic acid represented by the formula $A\text{-SO}_3H$ is a compound of the following general formula (6),

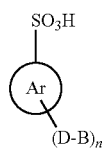

(6)

in which
Ar represents an aryl group, in which a substituent other than the -(D-B) group may further be introduced,
n is an integer of 1 or greater,
D represents a single bond or a bivalent connecting group, and
B represents a hydrocarbon group.

6. The actinic ray- or radiation-sensitive resin composition according to claim 5, characterized in that the acid crosslinking agent is a compound containing two or more hydroxymethyl groups or alkoxymethyl groups in each molecule thereof.

7. A method of forming a pattern, comprising:
forming a film using the composition according to claim 5,
subjecting the film to exposure, and
developing the exposed film.

8. The actinic ray- or radiation-sensitive resin composition according to claim 1, wherein B in the general formula (6) represents a branched alkyl group.

9. The actinic ray- or radiation-sensitive resin composition according to claim 1, wherein B in the general formula (6) represents a monocycloalkyl group.

10. An actinic ray- or radiation-sensitive resin composition comprising:
a sulfonic acid-generating compound that is decomposed by an action of an acid to generate a sulfonic acid having a volume of 240 Å$^3$ or more;
a compound that generates the acid when exposed to actinic rays or radiation; and
further comprising a resin that is decomposed by an action of the acid to increase its solubility in an alkaline developer,
wherein
the sulfonic acid-generating compound is any of compounds of general formulae (1) to (5) below and the sulfonic acid is represented by a formula $A\text{-SO}_3H$

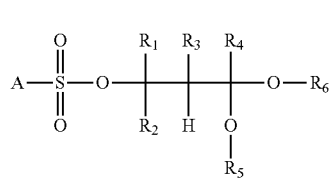

(1)

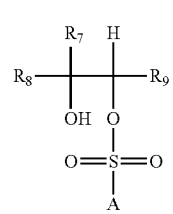

(2)

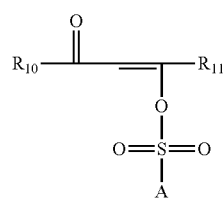

(3)

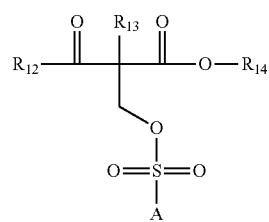

(4)

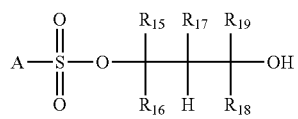

(5)

where
each of $R_1$ to $R_4$, $R_7$ to $R_{13}$ and $R_{15}$ to $R_{19}$ represents a hydrogen atom or a monovalent substituent,
each of $R_5$, $R_6$ and $R_{14}$ represents a monovalent substituent, and
A in the formula $A\text{-SO}_3H$ represents a residue of the sulfonic acid, and wherein
the sulfonic acid represented by the formula A-SO$_3$H is a compound of the following general formula (7),

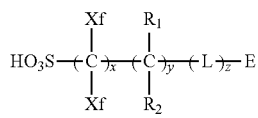
(7)

in which
each of Xf's independently represents a fluorine atom or an alkyl group substituted with at least one fluorine atom,
each of R$_1$ and R$_2$ independently represents a group selected from the group consisting of a hydrogen atom, a fluorine atom, an alkyl group and an alkyl group substituted with at least one fluorine atom, provided that a plurality of R$_1$s or R$_2$s may be identical to or different from each other,
L represents a single bond or a bivalent connecting group, provided that a plurality of L's may be identical to or different from each other,
E represents a group with a cyclic structure,
x is an integer of 1 to 20,
y is an integer of 0 to 10, and
z is an integer of 0 to 10.

11. The actinic ray- or radiation-sensitive resin composition according to claim 10, wherein E in the general formula (7) represents a cycloaliphatic group having a polycyclic structure.

12. The actinic ray- or radiation-sensitive resin composition according to claim 5, wherein B in the general formula (6) represents a branched alkyl group.

13. The actinic ray- or radiation-sensitive resin composition according to claim 5, wherein B in the general formula (6) represents a monocycloalkyl group.

14. An actinic ray- or radiation-sensitive resin composition comprising:
a sulfonic acid-generating compound that is decomposed by an action of an acid to generate a sulfonic acid having a volume of 240 Å$^3$ or more;
a compound that generates the acid when exposed to actinic rays or radiation; and
further comprising a resin soluble in an alkaline developer and an acid crosslinking agent capable of crosslinking with the resin by an action of the acid,
wherein
the sulfonic acid-generating compound is any of compounds of general formulae (1) to (5) below and the sulfonic acid is represented by a formula A-SO$_3$H

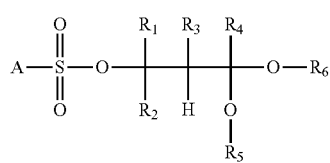
(1)

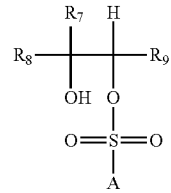
(2)

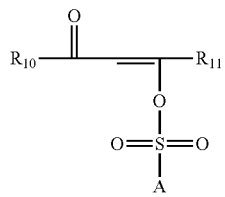
(3)

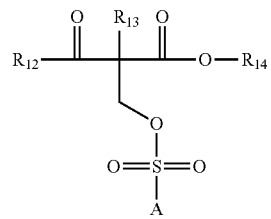
(4)

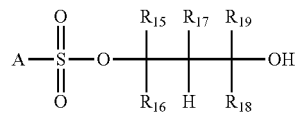
(5)

where
each of R$_1$ to R$_4$, R$_7$ to R$_{13}$ and R$_{15}$ to R$_{19}$ represents a hydrogen atom or a monovalent substituent,
each of R$_5$, R$_6$ and R$_{14}$ represents a monovalent substituent, and
A in the formula A-SO$_3$H represents a residue of the sulfonic acid,
and wherein
the sulfonic acid represented by the formula A-SO$_3$H is a compound of the following general formula (7),

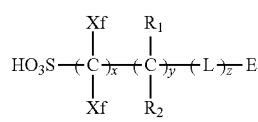
(7)

in which
each of Xf's independently represents a fluorine atom or an alkyl group substituted with at least one fluorine atom,
each of R$_1$ and R$_2$ independently represents a group selected from the group consisting of a hydrogen atom, a fluorine atom, an alkyl group and an alkyl group substituted with at least one fluorine atom, provided that a plurality of R$_1$s or R$_2$s may be identical to or different from each other,
L represents a single bond or a bivalent connecting group, provided that a plurality of L's may be identical to or different from each other,
E represents a group with a cyclic structure,
x is an integer of 1 to 20,
y is an integer of 0 to 10, and
z is an integer of 0 to 10.

15. The actinic ray- or radiation-sensitive resin composition according to claim 14, wherein E in the general formula (7) represents a cycloaliphatic group having a polycyclic structure.

* * * * *